(12) United States Patent
Hwang et al.

(10) Patent No.: US 11,192,878 B2
(45) Date of Patent: Dec. 7, 2021

(54) PIPERIDINE-2,6-DIONE DERIVATIVE AND USE THEREOF

(71) Applicant: KOREA RESEARCH INSTITUTE OF CHEMICAL TECHNOLOGY, Daejeon (KR)

(72) Inventors: Jong Yeon Hwang, Jeollabuk-do (KR); Jae Du Ha, Daejeon (KR); Sung Yun Cho, Daejeon (KR); Pil Ho Kim, Daejeon (KR); Chang Soo Yun, Daejeon (KR); Chi Hoon Park, Daejeon (KR); Chong Ock Lee, Seoul (KR); Sang Un Choi, Daejeon (KR); Joo Youn Lee, Daejeon (KR); Sunjoo Ahn, Daejeon (KR)

(73) Assignee: KOREA RESEARCH INSTITUTE OF CHEMICAL TECHNOLOGY, Daejeon (KR)

( * ) Notice: Subject to any disclaimer, the term of this patent is extended or adjusted under 35 U.S.C. 154(b) by 77 days.

(21) Appl. No.: 16/609,805

(22) PCT Filed: May 11, 2018

(86) PCT No.: PCT/KR2018/005444
§ 371 (c)(1),
(2) Date: Oct. 31, 2019

(87) PCT Pub. No.: WO2018/208123
PCT Pub. Date: Nov. 15, 2018

(65) Prior Publication Data
US 2020/0062730 A1    Feb. 27, 2020

(30) Foreign Application Priority Data

May 12, 2017   (KR) .......................... 10-2017-0059620
Dec. 29, 2017   (KR) .......................... 10-2017-0184761

(51) Int. Cl.
*C07D 401/04*   (2006.01)
*A61P 35/00*    (2006.01)
*C07D 401/14*   (2006.01)

(52) U.S. Cl.
CPC ............ *C07D 401/04* (2013.01); *A61P 35/00* (2018.01); *C07D 401/14* (2013.01)

(58) Field of Classification Search
CPC .. C07D 401/04; C07D 401/14; C07D 253/08; A61K 31/53; A61P 35/00

USPC ........................................................ 514/243
See application file for complete search history.

(56) References Cited

U.S. PATENT DOCUMENTS 5,643,915 A       7/1997   Andrulis, Jr. et al.
2011/0201657 A1   8/2011   Boueres et al.

FOREIGN PATENT DOCUMENTS

| AU | 2017202864 A1 | 9/2019 |
|---|---|---|
| KR | 10-2010-0080540 A | 7/2010 |
| WO | WO-2008/039489 A2 | 4/2008 |
| WO | WO-2009/042177 A1 | 4/2009 |
| WO | WO-2009/075795 A1 | 6/2009 |
| WO | WO-2014/110558 A1 | 7/2014 |
| WO | WO-2014/152833 A1 | 9/2014 |
| WO | WO-2017/067530 A2 | 4/2017 |
| WO | WO-2017/197051 A1 | 11/2017 |

OTHER PUBLICATIONS

Wang, G., et al.; "Synthesis and Nematicidal Activities of 1,2,3-Benzotriazin-4-one Derivatives against Meloidogyne incognita", J. Agric. Food Chem. 2015, 63, 6883?6889.
Singhal, S., et al.; "Antitumor Activity of Thalidomide in Refractory Multiple Myeloma", The New England Journal of Medicine, vol. 341 No. 21, 1999, pp. 1565-1571.
Chamberlain, P. P., et al.; "Structure of the human Cereblon-DDB1-lenalidomide complex reveals basis for responsiveness to thalidomide analogs", nature structural & molecular biology vol. 21 No. 9 Sep. 2014, pp. 803-810.
Matyskiela, M. E., et al.; "A novel cereblon modulator recruits GSPT1 to the CRL4CRBN ubiquitin ligase", Nature, 2016, pp. 1-24.
International Search Report from corresponding PCT Application No. PCT/KR2018/005444, dated Aug. 28, 2018.

*Primary Examiner* — Kahsay Habte
(74) *Attorney, Agent, or Firm* — Harness, Dickey & Pierce, P.L.C.

(57) ABSTRACT

The present disclosure relates to a novel piperidine-2,6-dione derivative and a use thereof and, more specifically, to a piperidine-2,6-dione derivative compound having a structure of a thalidomide analog. A compound of chemical formula 1 according to the present disclosure specifically binds with CRBN protein, and is involved in functions thereof. Therefore, the compound of the present disclosure can be favorably used in the prevention or treatment of leprosy, chronic graft versus host disease, an inflammatory disease, or cancer, which are caused by actions of CRBN protein.

5 Claims, 1 Drawing Sheet

PIPERIDINE-2,6-DIONE DERIVATIVE AND USE THEREOF

CROSS-REFERENCE TO RELATED APPLICATIONS

This application is a national phase application of PCT Application No. PCT/KR2018/005444, filed on May 11, 2018, which claims the benefit and priority to Korean Patent Application Nos. 10-2017-0059620, filed on May 12, 2017 and 10-2017-0184761, filed on Dec. 29, 2017. The entire disclosures of the applications identified in this paragraph are incorporated herein by references.

FIELD

The present disclosure relates to a novel piperidine-2,6-dione derivative and a use thereof, and more specifically, to a piperidine-2,6-dione derivative compound showing an effect of preventing or treating leprosy, chronic graft versus host disease, an inflammatory disease, or cancer.

BACKGROUND

Thalidomide is a racemic compound sold under the trademark name of THALOMID (registered trademark) and the chemical name of α-(N-phthalimido)glutarimide or 2-(2,6-dioxo-3-piperidinyl)-1H-isoindole-1,3(2H)-dione. Thalidomide was originally developed to treat morning sickness, but its use was discontinued due to the teratogenic effect. Thalidomide is currently approved in treatment of human erythema nodosum leprosum in U.S. (Physician's Desk Reference (registered trademark), 1081-1085 (55th ed., 2001)).

In addition, thalidomide has been reported to be used for patients of leprosy, chronic graft versus host disease, rheumatoid arthritis, sarcoidosis, some inflammatory skin diseases and inflammatory intestinal diseases, and thalidomide has been reported to be combined with other drugs to treat heart and cerebral artery occlusion-related ischemia/reperfusion (U.S. Pat. No. 5,643,915).

More recently, thalidomide has been used to treat certain types of cancer. This includes refractory multiple myeloma, brain, melanoma, breast, colon, mesothelioma and renal cell carcinoma (see Singhal, S., et al., 341 (21) New England J. Med., 1565-1571 (1999); and Marx, G. M., et al., 18 Proc. Am. Soc. Clin. Oncology, 454a (1999)). Thalidomide has been further reported to be used for preventing the expression of chronic cardiomyopathy caused by doxorubicin in rats (Costa, P. T., et al., 92 (10: suppl. 1) Blood, 235b (1998)). Another report relating to the use of thalidomide in treatment of certain cancer includes use in combination with carboplatin when treating glioblastoma multiforme (McCann, J., Drug Topics 41-42 (Jun. 21, 1999)). Thalidomide has been also reported to be used as an antiemeticum when treating astrocytoma (Zwart, D., 16 (12) Arzneim.-Forsch., 1688-1689 (1966)).

In addition, thalidomide is utilized in various ways for a purpose of preventing or treating lupus nephritis, fibromyalgia, schizophrenia, central nervous system diseases, diabetes, inflammatory diseases and the like, but it has a history of withdrawal from the market at the end of 1961 due to deadly side effects which cause malformations in pregnant women taking it.

Studies have been actively conducted to develop a derivative in which the problem of severe side effects is solved while retaining various physiological usefulness of thalidomide.

SUMMARY

Technical Problem

The present inventors have tried to develop a novel derivative compound which retains the physiological activity of thalidomide itself and has no side effects of thalidomide, and in particular, have developed a novel thalidomide derivative based on piperidine-2,6-dione and have evaluated its activity, thereby completing the present disclosure.

Thus, an object of the present disclosure is to provide a compound represented by the following Chemical formula 1 or its pharmaceutically acceptable salt.

[Chemical formula 1]

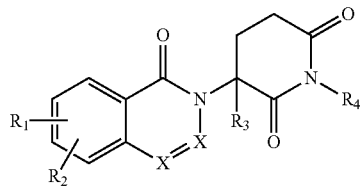

In the Chemical formula 1,

X is nitrogen (N) or carbon (C), and $R_1$ or $R_2$ is each independently substituted by one or more kinds of substituents selected from the group consisting of hydrogen, hydroxy, halogen, cyano, amino, nitro, —$NR_5R_6$, —$N(SO_2)R_7$, —$CONR_5R_6$, —$OR_5$, —$SR_5$, —$SO_2R_5$, —$SO_2NR_5R_6$, —$CR_5R_6$, —$CR_5NR_6R_7$, —$P(O)(OR_5)R_6$, —$P(O)R_5R_6$, —$OP(O)(OR_5)R_6$, —$OP(O)R_5R_6$, —$CF_3$, —$NR_5SO_2NR_5R_6$, —$CONR_5COR_6$, —$NR_5C(=N-CN)NR_5R_6$, —$C(=N-CN)NR_5R_6$, —$NR_5C(=N-CN)R_6$, —$NR_5C(=C-NO_2)NR_5R_6$, —$SO_2NR_5COR_6$, —$CO_2R_5$, —$C(C=N-OR_5)R_6$, —$CR_5=CR_5R_6$, —$CCR_5$, —$S(C=O)(C=N-R_5)R_6$, —$SF_5$, —$OCF_3$, —$NHCOR_5$, unsubstituted or substituted $C_1$-$C_{10}$ linear or branched alkyl, unsubstituted or substituted $C_1$-$C_{10}$ linear or branched alkenyl, unsubstituted or substituted $C_1$-$C_{10}$ linear or branched alkynyl, unsubstituted or substituted $C_1$-$C_{10}$ linear or branched alkoxy, unsubstituted or substituted $C_3$-$C_{10}$ cycloalkyl, unsubstituted or substituted $C_3$-$C_{10}$ heterocycloalkyl comprising one or more heteroatoms selected from the group consisting of N, O and S, unsubstituted or substituted $C_3$-$C_{10}$ cycloalkenyl, unsubstituted or substituted $C_3$-$C_{10}$ heterocycloalkenyl comprising one or more heteroatoms selected from the group consisting of N, O and S, unsubstituted or substituted $C_6$-$C_{14}$ aryl, unsubstituted or substituted $C_6$-$C_{24}$ arylalkyl, unsubstituted or substituted $C_6$-$C_{14}$ heteroaryl comprising one or more heteroatoms selected from the group consisting of N, O and S, and $R_3$ is substituted by one or more kinds of substituents selected from the group consisting of hydrogen, deuterium or unsubstituted or substituted $C_1$-$C_{10}$ linear or branched alkyl, and $R_4$ is substituted by one or more kinds of substituents selected from the group consisting of hydrogen, —$(CH_2)_nOCOR_8$ or unsubstituted or substituted $C_1$-$C_{10}$ linear or branched alkyl, and $R_5$ to $R_8$ are each independently substituted by one or more kinds of substituents selected from the group consisting of hydrogen, unsubstituted or substituted amino, unsubstituted or substituted $C_1$-$C_{10}$ linear or branched alkyl, unsubstituted or substituted $C_1$-$C_{10}$ linear or branched alkenyl, unsubstituted or substituted $C_1$-$C_{10}$ linear or branched alkynyl unsubstituted or substituted $C_3$-$C_{10}$ cycloalkyl, unsubstituted or substituted $C_3$-$C_{10}$ heterocycloalkyl comprising one or more heteroatoms selected from the group consisting of N, O and S, unsubstituted or substituted $C_6$-$C_{14}$ aryl or unsubstituted or substituted $C_6$-$C_{14}$ heteroaryl comprising one or more heteroatoms selected from the group consisting of N, O and S, and n is an integer of 1 to 5.

In addition, another object of the present disclosure is to provide a method comprising (a) reacting a compound represented by the following Chemical formula 2 with a compound represented by the following Chemical formula 3 to prepare a compound represented by the following Chemical formula 4; and (b) reacting the compound represented by the following Chemical formula 4 with $NaNO_2$ to prepare a compound represented by the following Chemical formula 5.

[Chemical formula 2]

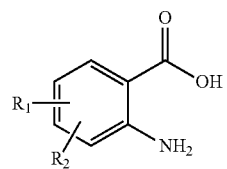

[Chemical formula 3]

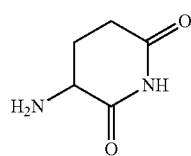

[Chemical formula 4]

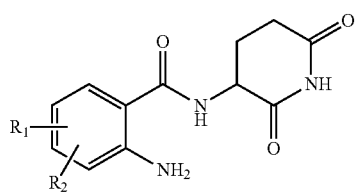

[Chemical formula 5]

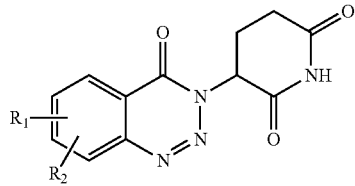

Other object of the present disclosure is to provide a pharmaceutical composition for preventing or treating leprosy, chronic graft versus host disease, an inflammatory disease, or cancer, comprising the compound or its pharmaceutically acceptable salt as an active ingredient.

Technical Solution

In order to achieve the afore-mentioned objects of the present disclosure, the present disclosure provides a compound represented by the following Chemical formula 1 or its pharmaceutically acceptable salt.

[Chemical formula 1]

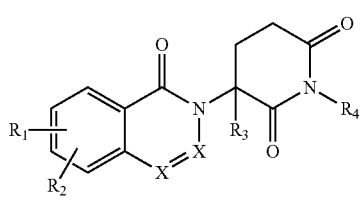

In the Chemical formula 1,

X is nitrogen (N) or carbon (C), and $R_1$ or $R_2$ is each independently substituted by one or more kinds of substituents selected from the group consisting of hydrogen, hydroxy, halogen, cyano, amino, nitro, —$NR_5R_6$, —$N(SO_2)R_7$, —$CONR_5R_6$, —$OR_5$, —$SR_5$, —$SO_2R_5$, —$SO_2NR_5R_6$, —$CR_5R_6$, —$CR_5NR_6R_7$, —$P(O)(OR_5)R_6$, —$P(O)R_5R_6$, —$OP(O)(OR_5)R_6$, —$OP(O)R_5R_6$, —$CF_3$, —$NR_5SO_2NR_5R_6$, —$CONR_5COR_6$, —$NR_5C(=N-CN)NR_5R_6$, —$C(=N-CN)NR_5R_6$, —$NR_5C(=N-CN)R_6$, —$NR_5C(=C-NO_2)NR_5R_6$, —$SO_2NR_5COR_6$, —$CO_2R_5$, —$C(C=N-OR_5)R_6$, —$CR_5=CR_5R_6$, —$CCR_5$, —$S(C=O)(C=N-R_5)R_6$, —$SF_5$, —$OCF_3$, —$NHCOR_5$, unsubstituted or substituted $C_1$-$C_{10}$ linear or branched alkyl, unsubstituted or substituted $C_1$-$C_{10}$ linear or branched alkenyl, unsubstituted or substituted $C_1$-$C_{10}$ linear or branched alkynyl, unsubstituted or substituted $C_1$-$C_{10}$ linear or branched alkoxy, unsubstituted or substituted $C_3$-$C_{10}$ cycloalkyl, unsubstituted or substituted $C_3$-$C_{10}$ heterocycloalkyl comprising one or more heteroatoms selected from the group consisting of N, O and S, unsubstituted or substituted $C_3$-$C_{10}$ cycloalkenyl, unsubstituted or substituted $C_3$-$C_{10}$ heterocycloalkenyl comprising one or more heteroatoms selected from the group consisting of N, O and S, unsubstituted or substituted $C_6$-$C_{14}$ aryl, unsubstituted or substituted $C_6$-$C_{24}$ arylalkyl, unsubstituted or substituted $C_6$-$C_{14}$ heteroaryl comprising one or more heteroatoms selected from the group consisting of N, O and S, and $R_3$ is substituted by one or more kinds of substituents selected from the group consisting of hydrogen, deuterium or unsubstituted or substituted $C_1$-$C_{10}$ linear or branched alkyl, and $R_4$ is substituted by one or more kinds of substituents selected from the group consisting of hydrogen, —$(CH_2)_nOCOR_8$ or unsubstituted or substituted $C_1$-$C_{10}$ linear or branched alkyl, and $R_5$ to $R_8$ are each independently substituted by one or more kinds of substituents selected from the group consisting of hydrogen, unsubstituted or substituted amino, unsubstituted or substituted $C_1$-$C_{10}$ linear or branched alkyl, unsubstituted or substituted $C_1$-$C_{10}$ linear or branched alkenyl, unsubstituted or substituted $C_1$-$C_{10}$ linear or branched alkynyl unsubstituted or substituted $C_3$-$C_{10}$ cycloalkyl, unsubstituted or substituted $C_3$-$C_{10}$ heterocycloalkyl comprising one or more heteroatoms selected from the group consisting of N, O and S, unsubstituted or substituted $C_6$-$C_{14}$ aryl or unsubstituted or substituted $C_6$-$C_{14}$ heteroaryl comprising one or more heteroatoms selected from the group consisting of N, O and S, and n is an integer of 1 to 5.

The following terms in the present disclosure have the following meanings, unless otherwise indicated. Any undefined term has the meaning as understood in the art.

"Halogen" in the present disclosure means fluoride (F), chloride (Cl), bromide (Br), and iodide (I).

The term "amino" used in the present disclosure means a primary, secondary or tertiary amino group which is bonded through a nitrogen atom alone or in combination (herein, the secondary amino group has a alkyl or cycloalkyl substituent, and the tertiary amino group has two similar or different alkyl or cycloalkyl substituents, or has two nitrogen substituents which forms a ring together), and for example, it is —$NH_2$, methylamino, ethylamino, dimethylamino, diethylamino, methyl-ethylamino, —$NR_5R_6$, —$N(SO_2)R_7$, —$NR_5SO_2NR_5R_6$, —$NR_5CONR_5R_6$, —$NR_5C(=N—CN)NR_5R_6$, —$NR_5C(=N—CN)R_6$, —$NR_5C(=C—NO_2)NR_5R_6$, pyrrolidin-1-yl or piperidino and the like, and preferably, it is a primary amino, $C_1$-$C_{10}$ alkyl amino.

The term "substituted" used in the present disclosure means comprising at least one substituent, for example, one or two or more of halogen atom, nitro, hydroxy, cyano, amino, thiol, carboxyl, amide, nitrile, sulfide, disulfide, sulphenyl, formyl, formyloxy, formylamino, aryl or substituted aryl, unless otherwise indicated. Unless otherwise indicated, or when the structure obtained by such substitution does not significantly adversely affect the properties of the compound represented by Chemical formula 1 of the present disclosure, any group or structure described may be substituted for the compound represented by Chemical formula 1 of the present disclosure.

The term "alkyl" used in the present disclosure means a hydrocarbon radical of carbon number 1~10 ($C_1$-$C_{10}$) comprising a linear or branched chain, more preferably carbon number 1~6 ($C_1$-$C_6$), further more preferably carbon number 1~4 ($C_1$-$C_4$), unless otherwise indicated. For example, it may include methyl, ethyl, n-propyl, isopropyl, cyclopropyl, n-butyl, sec-butyl, tert-butyl, cyclobutyl, cyclopropylmethyl, n-pentyl, isopentyl, neopentyl, tert-pentyl, cyclopentyl, cyclobutylmethyl, n-hexyl, isohexyl, cyclohexyl, cyclopentylmethyl, and so on. The alkyl may be a substituted or unsubstituted alkyl.

The term "alkenyl" or "alkynyl" used in the present disclosure means a hydrocarbon radical of carbon number 1~10 comprising a linear or branched chain containing one or more double bonds or triple bonds, respectively, more preferably carbon number 1~6, further more preferably carbon 1~4. The alkenyl or alkynyl may be a substituted or unsubstituted alkenyl or alkynyl, respectively.

The term "alkoxy" used in the present disclosure means a —O-alkyl group, and the alkyl is as described above. For example, it may include methoxy, trifluoromethoxy, ethoxy, n-propoxy, isopropoxy, n-butoxy, t-butoxy, sec-butoxy, n-pentoxy, and so on. The alkoxy may be a substituted or unsubstituted alkoxy.

The term "cycloalkyl" used in the present disclosure means a ring alkyl group, and is formed by having a single ring of 3 to 10 carbon atoms. For example, it may include cyclopropyl, cyclobutyl, cyclopentyl, cyclohexyl, cycloheptyl, cyclooctyl, and so on. The cycloalkyl may be a substituted or unsubstituted cycloalkyl.

The term "cycloalkenyl" used in the present disclosure means a ring alkenyl group, and is formed by having a single ring of 3 to 10 carbon atoms. For example, it may include cyclohexenyl, cyclopentenyl and cyclobutenyl and so on. The cycloalkenyl may be a substituted or unsubstituted cycloalkenyl.

The term "aryl" used in the present disclosure means an aromatic moiety, and is a carbocyclic functional group, and is formed by having a single ring of 6 to 14 carbon atoms (for example, phenyl) or a multiple fusion ring (for example, naphthyl, anthryl, phenanthryl). The aryl may be a substituted or unsubstituted aryl.

The term "arylalkyl" used in the present disclosure means an aryl group substituted by an alkyl group, and the aryl and alkyl are as described above.

"Heterocycloalkyl", "heterocycloalkenyl" and "heteroaryl" means "cycloalkyl", "cycloalkenyl" and "aryl" which have a single ring or multiple fusion ring and have 3 to 12 ring atoms and have at least one ring atoms substituted by same or different kinds of heteroatoms (for example, nitrogen, sulfur or oxygen), respectively.

In the present disclosure, the pharmaceutically acceptable salt means a salt or complex of Chemical formula 1 which retains the preferable biological activity. The examples of this salt includes acid addition salts formed by inorganic acids [for example, hydrochloric acid, hydrobromic acid, sulfuric acid, phosphoric acid, nitric acid, and the like], and salts formed by organic acids such as acetic acid, oxalic acid, tartaric acid, succinic acid, malic acid, fumaric acid, maleic acid, ascorbic acid, benzoic acid, tannic acid, pamoic acid, alginic acid, polyglutamic acid, naphthalene sulfonic acid, naphthalene disulfonic acid, and poly-galacturonic acid, but not limited thereto. The compound may be also administered as a pharmaceutically acceptable quaternary salt known to those skilled in the art, and in particular, it includes chloride, bromide, iodide, —O-alkyl, toluenesulfonate, methylsulfonate, sulfonate, phosphate, or carboxylate (for example, benzoate, succinate, acetate, glycolate, maleate, malate, fumarate, citrate, tartrate, ascorbate, cinnamoate, mandeloate and diphenylacetate. The compound of Chemical formula 1 of the present disclosure may include pharmaceutically acceptable salts, as well as all salts, hydrates and solvates which may be prepared by common methods.

In addition, the compound of the present disclosure may contain one or more asymmetry carbon atoms, and it may be present in racemic and optically active forms. All of these compounds and diastereomers are included in the scope of the present disclosure.

Preferably, in the Chemical formula 1, $R_1$ or $R_2$ may be each independently substituted by one or more kinds of substituents selected from the group consisting of hydrogen, hydroxy, halogen, cyano, amino, nitro, —$CH_3$, —$OCF_3$, —$OCH_3$, —$NHCOCH_3$, —COOH, —$CONH_2$, —$CONHCH_3$ or —$NHCOC_6H_5$, and $R_4$ may be substituted by one or more kinds of substituents selected from the group consisting of —$CH_2OCOC(CH_3)_3$, —$CH_2OCOC_6H_5$, —$CH_2COC_5H_{10}N$, —$CH_2OCOC_4H_8N$, —$CH_2OCOCH(NH_2)CH(CH_3)CH_2CH_3$, —$CH_2OCOCH_2CH_2CH_3$ or —$CH_2OCOC_4H_7NBoc$, and more preferably, the $R_4$ may be

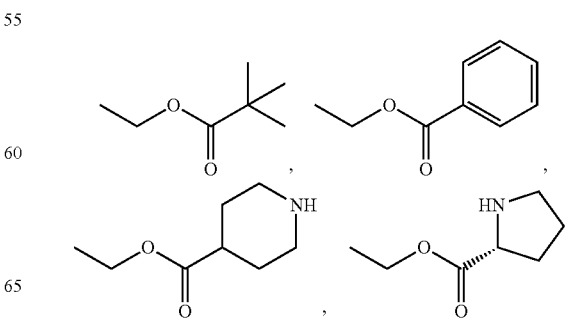

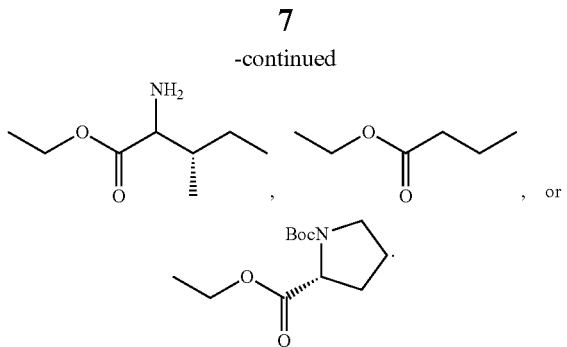

In addition, further more preferably, in the Chemical formula 1, X is nitrogen (N), and most preferably, in the Chemical formula 1, X is nitrogen (N), and $R_1$ or $R_2$ is each independently substituted by one or more kinds of substituents selected from the group consisting of hydrogen, hydroxy, halogen, cyano, amino, nitro, —$CH_3$, —$OCF_3$, —$OCH_3$, —$NHCOCH_3$, —COOH, —$CONH_2$, —$CONHCH_3$ or —$NHCOC_6H_5$, and $R_4$ is substituted by one or more kinds of substituents selected from the group consisting of —$CH_2OCOC(CH_3)_3$, —$CH_2OCOC_6H_5$, —$CH_2COC_5H_{10}N$, —$CH_2OCOC_4H_8N$, —$CH_2OCOCH(NH_2)CH(CH_3)CH_2CH_3$, —$CH_2OCOCH_2CH_2CH_3$ or —$CH_2OCOC_4H_7NBoc$ Furthermore, the present disclosure provides a method comprising (a) reacting a compound represented by the following Chemical formula 2 with a compound represented by the following Chemical formula 3 to prepare a compound represented by the following Chemical formula 4; and (b) reacting the compound represented by the following Chemical formula 4 with $NaNO_2$ to prepare a compound represented by the following Chemical formula 5.

[Chemical formula 2]

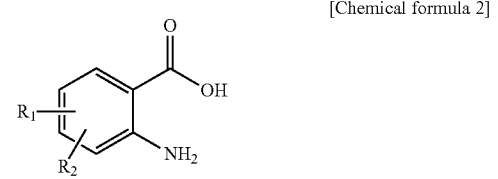

[Chemical formula 3]

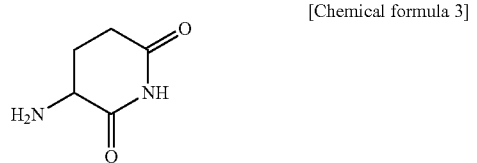

[Chemical formula 4]

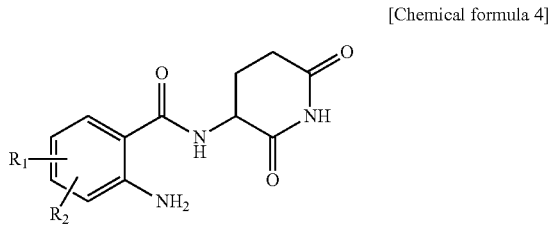

[Chemical formula 5]

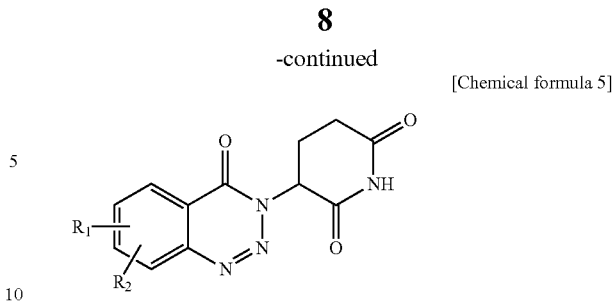

In the Chemical formula 2, $R_1$ or $R_2$ may be each independently substituted by one or more kinds of substituents selected from the group consisting of hydrogen, hydroxy, halogen, cyano, amino, nitro, —$CH_3$, —$OCF_3$, —$OCH_3$, —$NHCOCH_3$, —COOH, —$CONH_2$, —$CONHCH_3$ or —$NHCOC_6H_5$.

The solvent used in the step (a) of the present disclosure is not particularly limited as long as it is a solvent which dissolves a starting material and does not inhibit the reaction, and for example, ether-based solvents such as tetrahydrofuran, 1,2-dimethoxy ethane, diethyl ether or dioxane and the like; aromatic hydrocarbon-based solvents such as benzene, toluene or xylene and the like; amide-based solvents such as N,N-dimethylformamide, N,N-dimethylacetamide or N-methylpyrrolidone and the like; organic solvents such as dimethyl sulfoxide and the like; alcohol-based solvents such as methanol, ethanol, propanol, n-butanol or t-butanol and the like; or mixtures thereof or mixed solvents of the solvent and water may be used. Preferably, dimethylformamide may be used, but not limited thereto.

In addition, in order to perform the reaction in the step (a) easily, an appropriate base may be used. As the base, for example, sodium hydride, potassium t-butoxide, sodium methoxide, sodium ethoxide, N,N-diisopropylamine, diisopropylethylamine, 2,4-diaminobutyric acid (DBU) and the like may be used, and preferably, diisopropylethylamine may be used, but not limited thereto.

In the step (a), the reaction molar ratio of the compound of Chemical formula 2 and the compound of Chemical formula 3 may be 1:3 to 5, and most preferably, the reaction is progressed at a molar ratio of 1:4.

The step (b) is a step of adding sodium nitride to the compound of Chemical formula 4 produced in the step (a) to progress a cyclization reaction, and it is preferable to progress the reaction under slightly acidic and room temperature conditions.

The present disclosure also provides a pharmaceutical composition for preventing or treating leprosy, chronic graft versus host disease, an inflammatory disease, or cancer, comprising the compound of Chemical formula 1 or its pharmaceutically acceptable salt as an active ingredient.

Such effects of the present disclosure are well shown in an example of the present disclosure.

In the present disclosure, the treat means reversing a disease or disorder to which the term is applied, or one or more symptoms of the disease or disorder, alleviating it or them, inhibiting its or their progression, or preventing it or them, and the term treat used in the present disclosure refers to an act of treating.

According to one test example of the present disclosure, it was confirmed to bind to a CRBN (celebron) protein to degrade Ikaros/Aiolos, GSPI1. The CRBN protein is a kind of E3 ubiquitin ligases, and it has been known to have an activity to bind to thalidomide and its derivatives, pomalidomide, lenalidomide and the like to attach ubiquitin for substrate proteins such as Ikaros/Aiolos protein, GSPT1 protein, and so on.

In the present disclosure, the cancer may be selected from the group consisting of breast cancer, colorectal cancer, lung cancer, small cell lung cancer, gastric cancer, liver cancer, blood cancer, bone cancer, pancreatic cancer, skin cancer, head or neck cancer, skin or intraocular melanoma, uterine cancer, ovarian cancer, rectal cancer, anal region cancer, colon cancer, breast cancer, fallopian tube carcinoma, endometrial cancer, cervical cancer, vaginal cancer, vulva cancer, Hodgkin disease, esophageal cancer, small intestine cancer, endocrine gland cancer, thyroid cancer, parathyroid cancer, adrenal cancer, soft tissue sarcoma, urethral cancer, penile cancer, prostate cancer, chronic or acute leukemia, lymphocytic lymphoma, bladder cancer, kidney or ureteral cancer, renal cell carcinoma, renal pelvic carcinoma, CNS tumor, primary CNS lymphoma, spinal cord tumor, brainstem glioma and pituitary adenoma, but not limited thereto.

In addition, the compound of Chemical formula 1 of the present disclosure may be more specifically a compound of Chemical formula 6.

[Chemical formula 6]

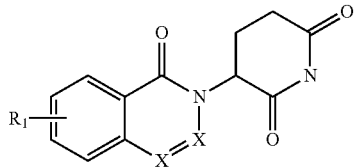

Most preferably, the compound of Chemical formula 1 of the present disclosure may be selected among the following compounds.

[Chemical formula 7]

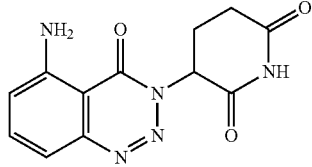

3-(5-amino-4-oxobenzo[d][1,2,3]triazin-3(4H)-yl)piperidine-2,6-dione

[Chemical formula 8]

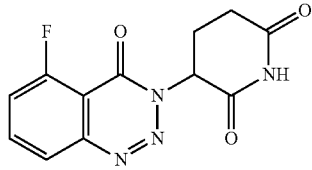

3-(5-fluoro-4-oxobenzo[d][1,2,3]triazin-3(4H)-yl)piperidine-2,6-dione

[Chemical formula 9]

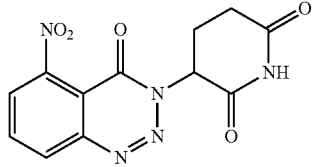

3-(5-nitro-4-oxobenzo[d][1,2,3]triazin-3(4H)-yl)piperidine-2,6-dione

[Chemical formula 10]

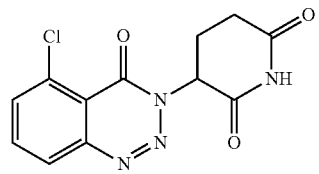

3-(5-chloro-4-oxobenzo[d][1,2,3]triazin-3(4H)-yl)piperidine-2,6-dione

[Chemical formula 11]

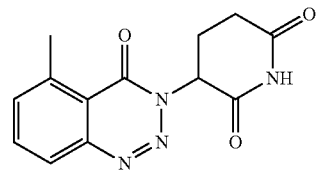

3-(5-methyl-4-oxobenzo[d][1,2,3]triazin-3(4H)-yl)piperidine-2,6-dione

[Chemical formula 12]

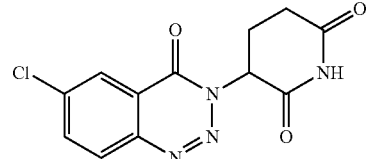

3-(6-chloro-4-oxobenzo[d][1,2,3]triazin-3(4H)-yl)piperidine-2,6-dione

[Chemical formula 13]

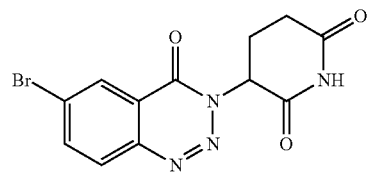

3-(6-bromo-4-oxobenzo[d][1,2,3]triazin-3(4H)-yl)piperidine-2,6-dione

[Chemical formula 14]

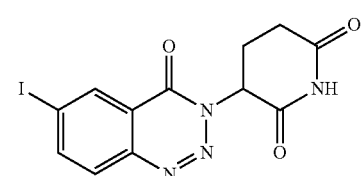

3-(6-iodo-4-oxobenzo[d][1,2,3]triazin-3(4H)-yl)piperidine-2,6-dione

[Chemical formula 15]

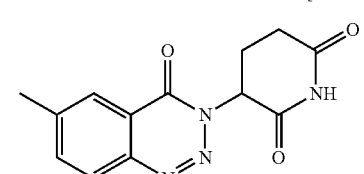

3-(8-bromo-6-methyl-4-oxobenzo[d][1,2,3]triazin-3(4H)-yl)piperidine-2,6-dione

[Chemical formula 16]

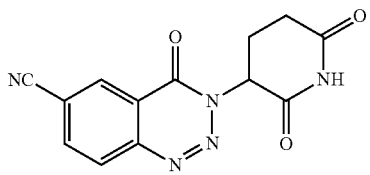

3-(2,6-dioxopiperidin-3-yl)-4-oxo-3,4-dihydrobenzo[d][1,2,3]triazin-6-carbonitrile

[Chemical formula 17]

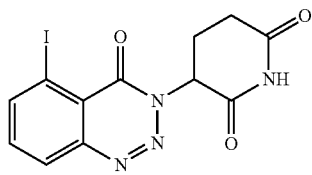

3-(5-iodo-4-oxobenzo[d][1,2,3]triazin-3(4H)-yl)piperidine-2,6-dione

[Chemical formula 18]

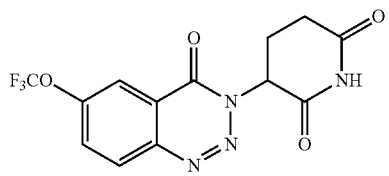

3-(4-oxo-6-(trifluoromethoxy)benzo[d][1,2,3]triazin-3(4H)-yl)piperidine-2,6-dione

[Chemical formula 19]

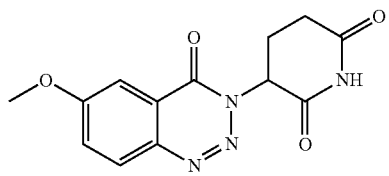

3-(6-methoxy-4-oxobenzo[d][1,2,3]triazin-3(4H)-yl)piperidine-2,6-dione

[Chemical formula 20]

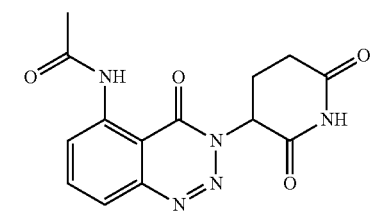

N-(3-(2,6-dioxopiperidin-3-yl)-4-oxo-3,4-dihydrobenzo[d][1,2,3]triazin-5-yl)acetamide

[Chemical formula 21]

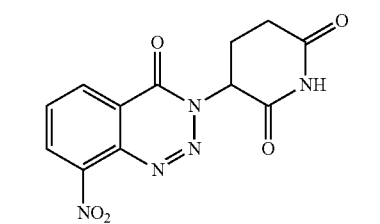

3-(8-nitro-4-oxobenzo[d][1,2,3]triazin-3(4H)-yl)piperidine-2,6-dione

[Chemical formula 22]

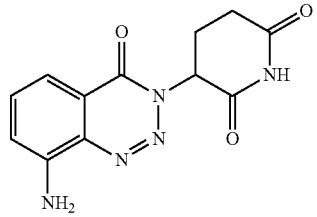

3-(8-amino-4-oxobenzo[d][1,2,3]triazin-3(4H)-yl)piperidine-2,6-dione

[Chemical formula 23]

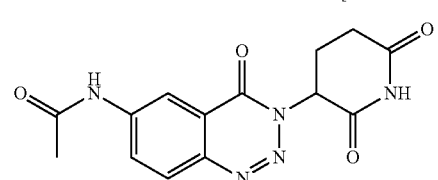

N-(3-(2,6-dioxopiperidin-3-yl)-4-oxo-3,4-dihydrobenzo[d][1,2,3]triazin-6-yl)acetamide

[Chemical formula 24]

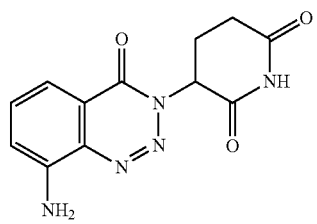

3-(5-amino-1-oxoisoquinolin-2(1H)-yl)piperidine-2,6-dione

[Chemical formula 25]

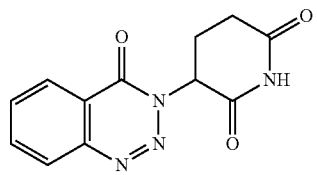

3-(4-oxobenzo[d][1,2,3]triazan-3(4H)-yl)piperidine-2,6-dione

[Chemical formula 26]

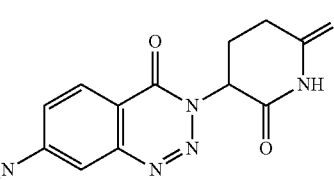

3-(7-nitro-4-oxobenzo[d][1,2,3]triazan-3(4H)-yl)piperidine-2,6-dione

[Chemical formula 27]

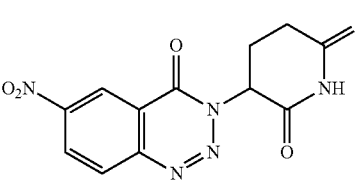

3-(6-nitro-4-oxobenzo[d][1,2,3]triazan-3(4H)-yl)piperidine-2,6-dione

[Chemical formula 28]

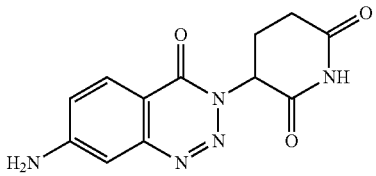

3-(7-amino-4-oxobenzo[d][1,2,3]triazan-3(4H)-yl)piperidine-2,6-dione

[Chemical formula 29]

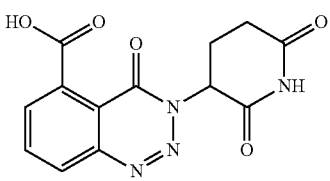

3-(2,6-dioxopiperidin-3-yl)-4-oxo-3,4-dihydrobenzo[d][1,2,3]triazin-5-carboxylic acid

[Chemical formula 30]

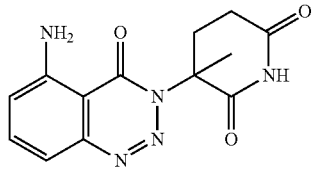

3-(5-amino-4-oxobenzo[d][1,2,3]triazin-3(4H)-yl)-3-methylpiperidine-2,6-dione

[Chemical formula 31]

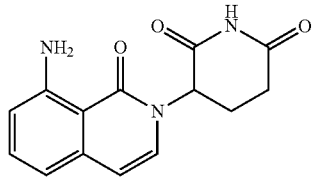

3-(8-amino-1-oxoisoquinolin-2(1H)-yl)piperidine-2,6-dione

[Chemical formula 32]

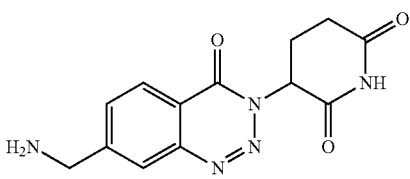

3-(7-(aminomethyl)-4-oxobenzo[d][1,2,3]triazan-3(4H)-yl)piperidine-2,6-dione

[Chemical formula 33]

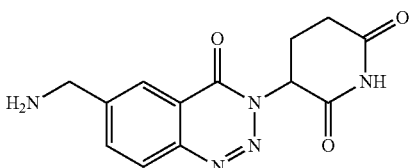

3-(6-(aminomethyl)-4-oxobenzo[d][1,2,3]triazan-3(4H)-yl)piperidine-2,6-dione

[Chemical formula 34]

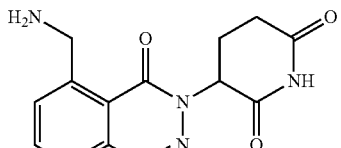

3-(5-(aminomethyl)-4-oxobenzo[d][1,2,3]triazan-3(4H)-yl)piperidine-2,6-dione

[Chemical formula 35]

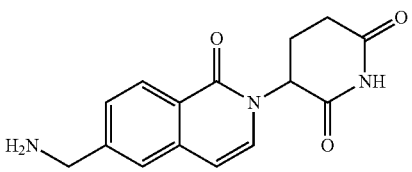

3-(6-(aminomethyl)-1-oxoisoquinolin-2(1H)-yl)piperidine-2,6-dione

[Chemical formula 36]

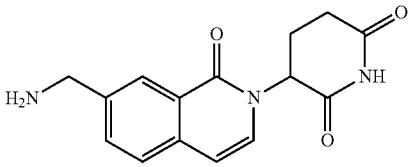

3-(7-(aminomethyl)-1-oxoisoquinolin-2(1H)-yl)piperidine-2,6-dione

[Chemical formula 37]

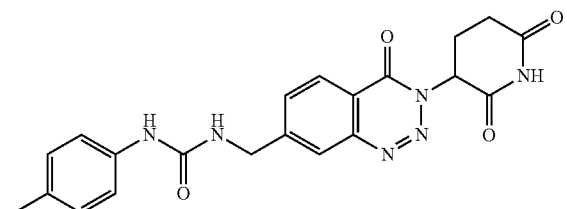

1-(3-chloro-4-methylphenyl)-3-((3-(2,6-dioxopiperidin-3-yl)-4-oxo-3,4-dihydrobenzo[d][1,2,3]triazin-7-yl)methyl)urea

[Chemical formula 38]

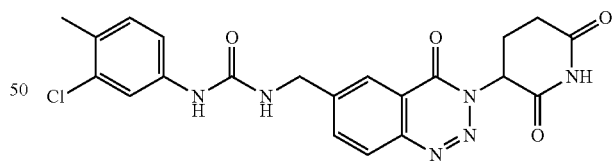

1-(3-chloro-4-methylphenyl)-3-((3-(2,6-dioxopiperidin-3-yl)-4-oxo-3,4-dihydrobenzo[d][1,2,3]triazin-6-yl)methyl)urea

[Chemical formula 39]

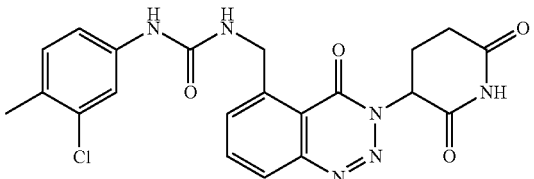

1-(3-chloro-4-methylphenyl)-3-((3-(2,6-dioxopiperidin-3-yl)-4-oxo-3,4-dihydrobenzo[d][1,2,3]triazin-5-yl)methyl)urea

[Chemical formula 40]

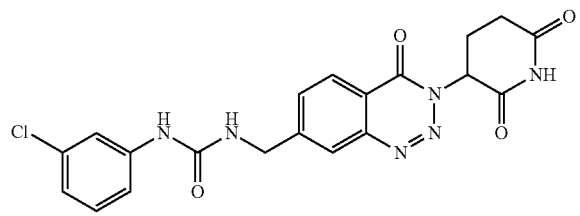

1-(3-chlorophenyl)-3-((3-(2,6-dioxopiperidin-3-yl)-4-oxo-3,4-dihydrobenzo[d][1,2,3]triazin-7-yl)methyl)urea

[Chemical formula 41]

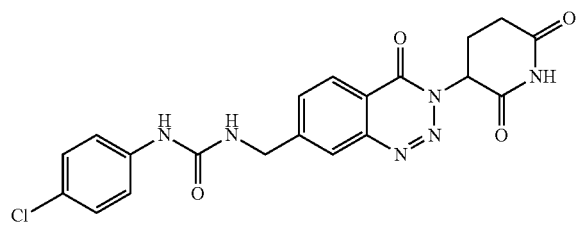

1-(4-chlorophenyl)-3-((3-(2,6-dioxopiperidin-3-yl)-4-oxo-3,4-dihydrobenzo[d][1,2,3]triazin-7-yl)methyl)urea

[Chemical formula 42]

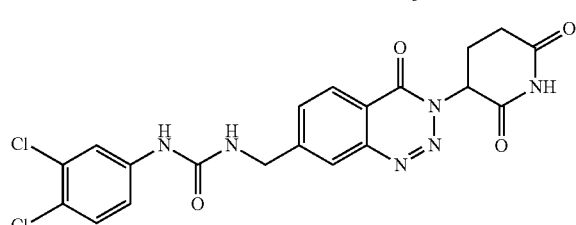

1-(3,4-dichlorophenyl)-3-((3-(2,6-dioxopiperidin-3-yl)-4-oxo-3,4-dihydrobenzo[d][1,2,3]triazin-7-yl)methyl)urea

[Chemical formula 43]

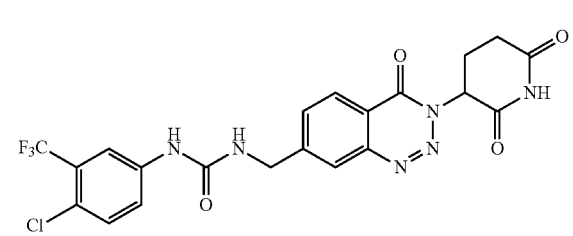

1-(4-chloro-3-(trifluoromethly)phenyl)-3-((3-(2,6-dioxopiperidin-3-yl)-4-oxo-3,4-dihydrobenzo[d][1,2,3]triazin-7-yl)methyl)urea

[Chemical formula 44]

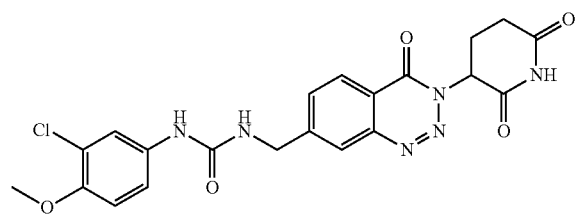

1-(3-chloro-4-methoxyphenyl)-3-((3-(2,6-dioxopiperidin-3-yl)-4-oxo-3,4-dihydrobenzo[d][1,2,3]triazin-7-yl)methyl)urea

[Chemical formula 45]

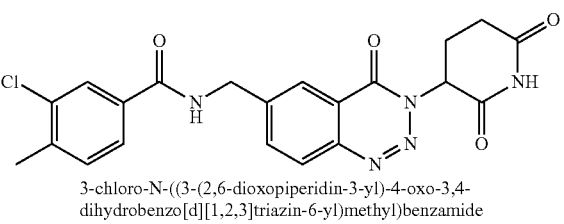

3-chloro-N-((3-(2,6-dioxopiperidin-3-yl)-4-oxo-3,4-dihydrobenzo[d][1,2,3]triazin-6-yl)methyl)benzamide

[Chemical formula 46]

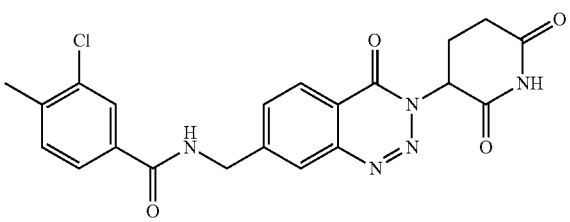

3-chloro-N-((3-(2,6-dioxopiperidin-3-yl)-4-oxo-3,4-dihydrobenzo[d][1,2,3]triazin-6-yl)methyl)-4-methylbenzamide

[Chemical formula 47]

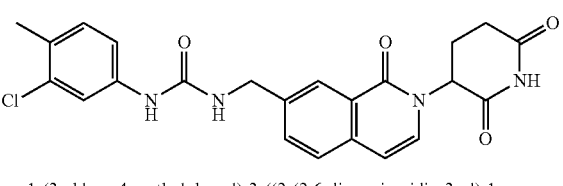

1-(3-chloro-4-methylphenyl)-3-((2-(2,6-dioxopiperidin-3-yl)-1-oxo-1,2-dihydroisoquinolin-7-yl)methyl)urea

[Chemical formula 48]

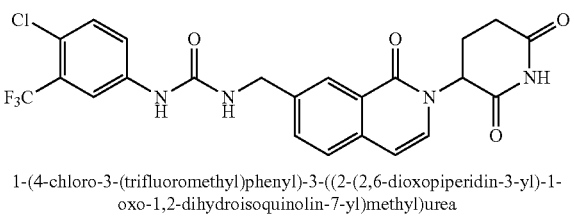

1-(4-chloro-3-(trifluoromethyl)phenyl)-3-((2-(2,6-dioxopiperidin-3-yl)-1-oxo-1,2-dihydroisoquinolin-7-yl)methyl)urea

[Chemical formula 49]

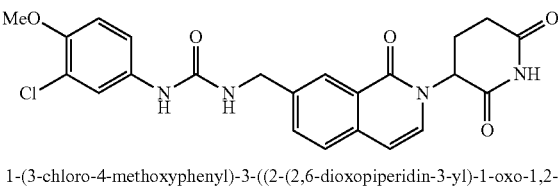

1-(3-chloro-4-methoxyphenyl)-3-((2-(2,6-dioxopiperidin-3-yl)-1-oxo-1,2-dihydroisoquinolin-7-yl)methyl)urea
(* Me: methyl group)

[Chemical formula 50]

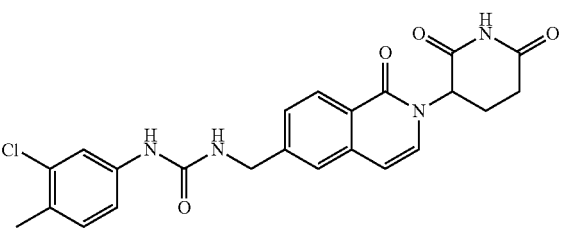

1-(3-chloro-4-methylphenyl)-3-((2-(2,6-dioxopiperidin-3-yl)-1-oxo-1,2-dihydroisoquinolin-6-yl)methyl)urea

[Chemical formula 51]

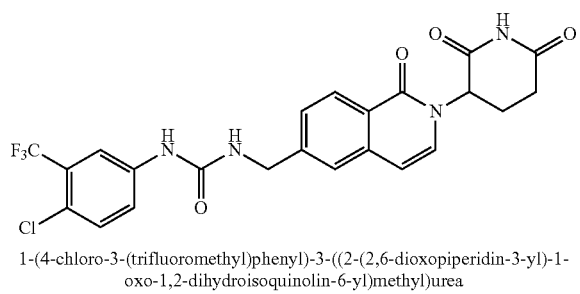

1-(4-chloro-3-(trifluoromethyl)phenyl)-3-((2-(2,6-dioxopiperidin-3-yl)-1-oxo-1,2-dihydroisoquinolin-6-yl)methyl)urea

[Chemical formula 52]

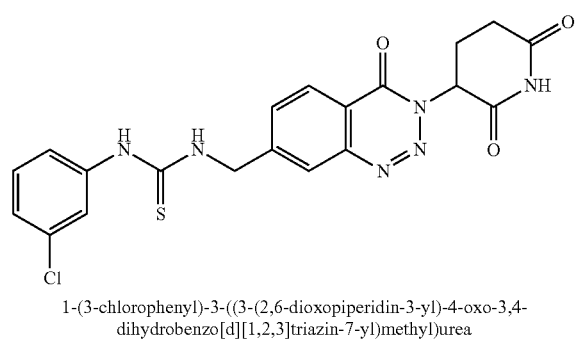

1-(3-chlorophenyl)-3-((3-(2,6-dioxopiperidin-3-yl)-4-oxo-3,4-dihydrobenzo[d][1,2,3]triazin-7-yl)methyl)urea

[Chemical formula 53]

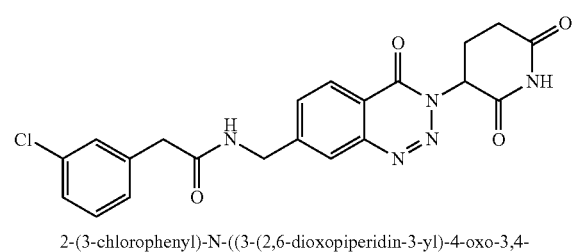

2-(3-chlorophenyl)-N-((3-(2,6-dioxopiperidin-3-yl)-4-oxo-3,4-dihydrobenzo[d][1,2,3]triazin-7-yl)methyl)acetamide

[Chemical formula 54]

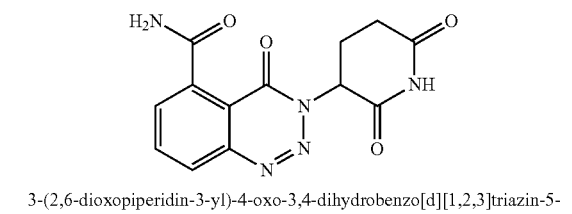

3-(2,6-dioxopiperidin-3-yl)-4-oxo-3,4-dihydrobenzo[d][1,2,3]triazin-5-carboxamide

[Chemical formula 55]

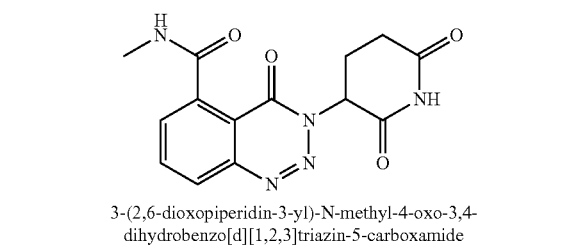

3-(2,6-dioxopiperidin-3-yl)-N-methyl-4-oxo-3,4-dihydrobenzo[d][1,2,3]triazin-5-carboxamide

[Chemical formula 56]

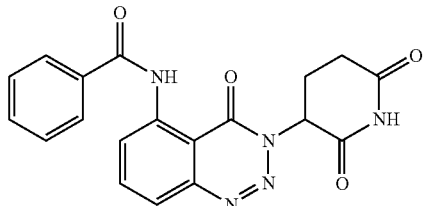

N-(3-(2,6-dioxopiperidin-3-yl)-4-oxo-3,4-dihydrobenzo[d][1,2,3]triazin-5-yl)benzamide

[Chemical formula 57]

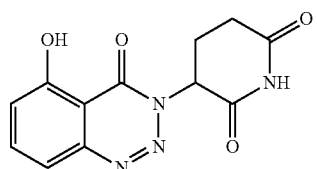

3-(5-hydroxy-4-oxobenzo[d][1,2,3]triazin-3(4H)-yl)piperidine-2,6-dione

[Chemical formula 58]

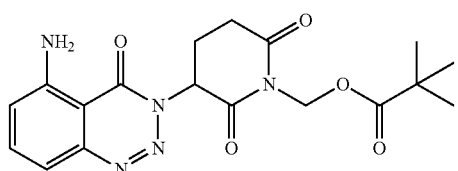

(3-(5-amino-4-oxobenzo[d][1,2,3]triazin-3(4H)-yl)-2,6-dioxopiperidin-1-yl)methyl pivalate

[Chemical formula 59]

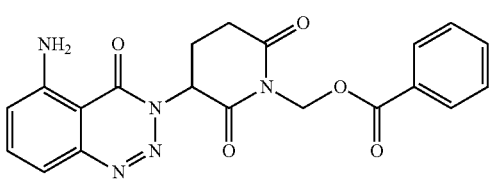

(3-(5-amino-4-oxobenzo[d][1,2,3]triazin-3(4H)-yl)-2,6-dioxopiperidin-1-yl)methyl benzoate

[Chemical formula 60]

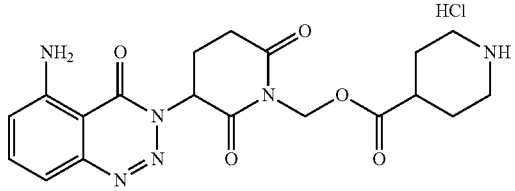

(3-(5-amino-4-oxobenzo[d][1,2,3]triazin-3(4H)-yl)-2,6-dioxopiperidin-1-yl)methyl piperdine-4-carboxylate hydrochloride

[Chemical formula 61]

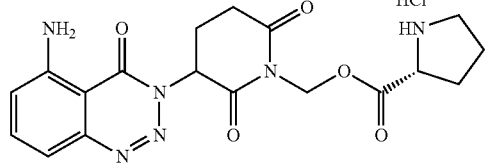

(3-(5-amino-4-oxobenzo[d][1,2,3]triazin-3(4H)-yl)-2,6-dioxopiperidin-1-yl)methyl D-prolinate hydrochloride -continued

[Chemical formula 62]

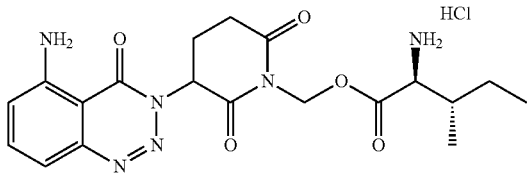

(3-(5-amino-4-oxobenzo[d][1,2,3]triazin-3(4H)-yl)-2,6-dioxopiperidin-1-yl)methyl L-isoleucinate hydrochloride

[Chemical formula 63]

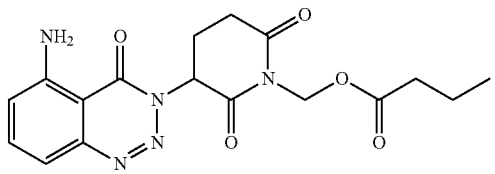

(3-(5-amino-4-oxobenzo[d][1,2,3]triazin-3(4H)-yl)-2,6-dioxopiperidin-1-yl)methyl butyrate

[Chemical formula 64]

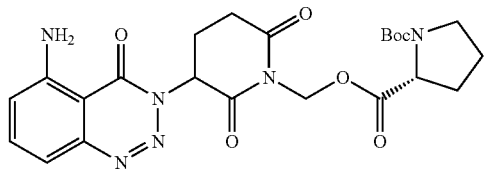

2-((3-(5-amino-4-oxobenzo[d][1,2,3]triazin-3(4H)-yl)-2,6-dioxopiperidin-1-yl)methyl) 1-(tert-butyl) (2R)-pyrrolidine-1,2-dicarboxylate

[Chemical formula 65]

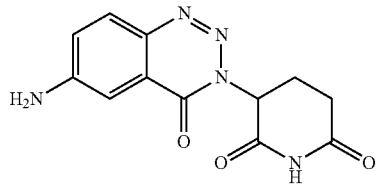

3-(6-amino-4-oxobenzo[d][1,2,3]triazin-3(4H)-yl)piperidine-2,6-dione

In the pharmaceutical composition according to the present disclosure, the compound of Chemical formula 1 or its pharmaceutically acceptable salt may be administered in various oral and parenteral formulations during clinical administration, and in case of preparation, it may be prepared using commonly used diluents or excipients such as fillers, extenders, binders, wetting agents, disintegrants and surfactants.

Solid preparations for oral administration include tablets, pills, powder, granules, capsules, troches, and the like, and such solid preparations may be prepared by mixing at least one excipient, for example, starch, calcium carbonate, sucrose or lactose or gelatin and so on, to at least one compound of Chemical formula 1 or its pharmaceutically acceptable salt of the present disclosure. In addition, other than the simple excipient, a lubricant such as magnesium stearate, talc and the like may be used. Liquid preparations for oral administration include suspension, liquid for internal use, emulsion or syrup and the like, and various excipients in addition to commonly used simple diluents, water and liquid paraffin, for example, wetting agents, sweeteners, aromatics, preservatives and the like may be included.

Preparations for parenteral administration include sterile aqueous solution, nonaqueous solvents, suspending agents, emulsion, lyophilized preparations, and suppository. As the nonaqueous solvents and suspending agents, propylene glycol, polyethylene glycol, plant oil such as olive oil, injectable ester such as ethyl oleate and the like may be used. As a base material of suppository, witepsol, macrogol, tween 61, cacao butter, laurin butter, glycerol, gelatin and the like may be used.

Moreover, the dosage of the compound of Chemical formula 1 or its pharmaceutically acceptable salt of the present disclosure to human may differ depending on the patient's age, body weight, gender, administration form, health condition and disease severity, and based on adult patients weighing 70 kg, it is generally 0.1-1000 mg/day, and preferably, 1-500 mg/day, and in addition, depending on the judgement of a doctor or pharmacist, it may be administered once a day to a number of doses divided at regular intervals.

The pharmaceutical composition of the present disclosure may be used alone, or in combination with surgery, hormone treatment, chemotherapy and methods using a biological response modifier.

On the other hand, the compound according to the present disclosure may be prepared in various forms depending on the purpose, Preparation examples for the composition of the present disclosure are exemplified below.

<Preparation Example 1> Preparation of a Pharmaceutical Preparation

1. Preparation of a Powder
2 g of the compound of Chemical formula 1 according to the present disclosure
lactose 1 g
The above ingredients were mixed and filled into an airtight pack to prepare a powder.

2. Preparation of a Tablet
100 mg of the compound of Chemical formula 1 according to the present disclosure
corn starch 100 mg
lactose 100 mg
magnesium stearate 2 mg
The above ingredients were mixed and then were tableted by the common preparation method of a tablet to prepare a tablet.

3. Preparation of a Capsule
100 mg of the compound of Chemical formula 1 according to the present disclosure
corn starch 100 mg
lactose 100 mg
magnesium stearate 2 mg
The above ingredients were mixed and then were filled into a gelatin capsule by the common preparation method of a capsule to prepare a capsule.

4. Preparation of a Pill
1 mg of the compound of Chemical formula 1 according to the present disclosure
lactose 1.5 g
glycerin 1 g
xylitol 0.5 g
The above ingredients were mixed, and then it was prepared so as to be 4 g per 1 pill by the common method.

5. Preparation of a Granule
150 mg of the compound of Chemical formula 1 according to the present disclosure
soybean extract 50 mg
glucose 200 mg
starch 600 mg The above ingredients were mixed, and then 100 mg of 30% ethanol was added, and it was dried at 60° C. to form a granule and then it was filled to a pack.

Advantageous Effects

The compound of Chemical formula 1 according to the present disclosure specifically binds to CRBN protein and is involved in its function. Accordingly, the compound of the present disclosure may be usefully used for prevention or treatment of leprosy, chronic graft versus host disease, an inflammatory disease, or cancer, which are caused by actions of CRBN protein.

DETAILED DESCRIPTION

Figure 1:
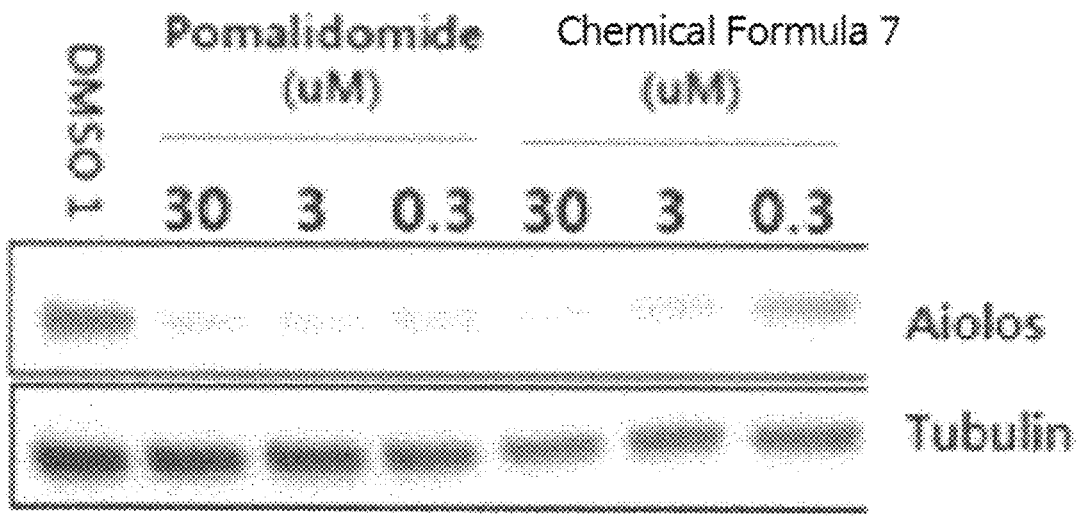
FIG. 1 is the measurement of the degradation activity against Aiolos when the compound of Chemical formula 7 of the present disclosure is treated for 6 hours.

Hereinafter, the present disclosure will be described in detail.

However, the following examples are intended to exemplify the present disclosure only, but the content of the present disclosure is not limited by the following examples.

Example 1

Synthesis of 3-(5-amino-4-oxobenzo[d][1,2,3]triazin-3(4H)-yl)piperidine-2,6-dione (Chemical Formula 7)

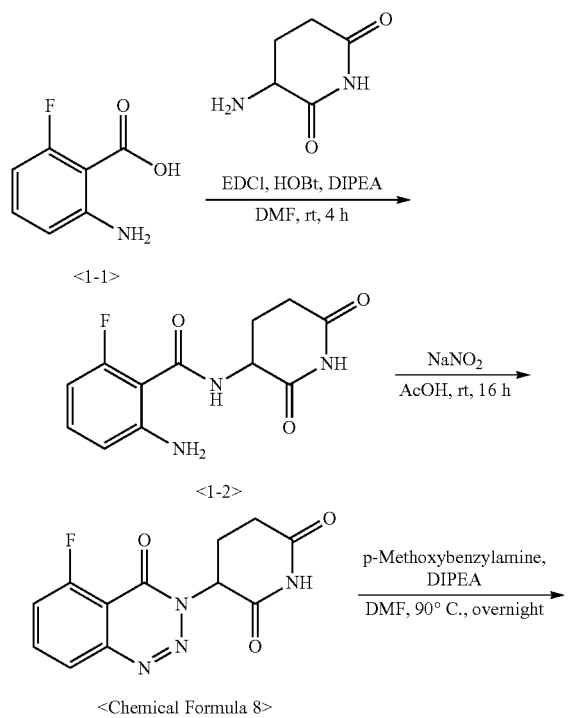

<Chemical Formula 8>

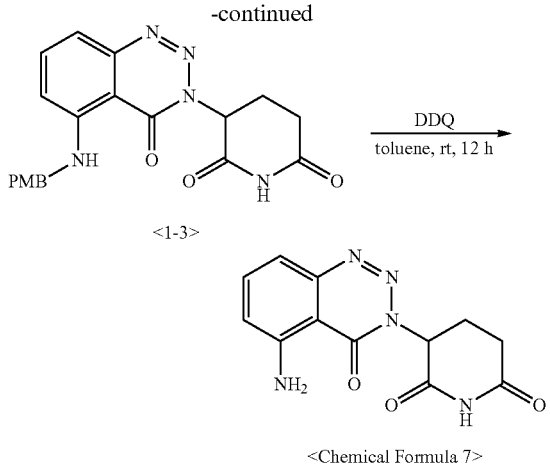

<Chemical Formula 7>

[1-1] Synthesis of 2-amino-N-(2,6-dioxopiperidin-3-yl)-6-fluorobenzamide (Compound <1-2>)

2-amino-6-fluorobenzoic acid (394 mg, 2.54 mmol) was dissolved in DMF (12 ml) and EDCl-HCl (540 mg, 2.8 mmol) and HOBt (429 mg, 2.8 mmol) were added. After stirring at a room temperature for 30 minutes, amine (361 mg, 2.8 mmol) was added, and DIPEA (1.4 ml, 8.12 mmol) was added, and it was stirred at a room temperature for 16 hours. The reaction mixture was diluted with water and then was extracted with ethyl acetate. The organic layer was dried on $Na_2SO_4$, and it was purified by column chromatography, to obtain pure 2-amino-N-(2,6-dioxopiperidin-3-yl)-6-fluorobenzamide compound 406 mg (60%) as a white solid.

$^1$H NMR (300 MHz, DMSO-$d_6$) δ 10.90 (s, 1H), 8.53 (d, J=6.0 Hz, 1H), 7.09 (dd, J=14.9, 8.1 Hz, 1H), 6.52 (d, J=8.2 Hz, 1H), 6.42-6.26 (m, 1H), 6.00 (s, 2H), 4.84-4.61 (m, 1H), 2.97-2.70 (m, 1H), 2.56-2.54 (m, 1H), 2.24-1.94 (m, 2H);

MS found (M+H)$^+$ (m/z), 266.09; calcd for $C_{12}H_{12}FN_3O_3$ m/z, 266.10.

[1-2] Synthesis of 3-(5-fluoro-4-oxobenzo[d][1,2,3]triazin-3(4H)-yl)piperidine-2,6-dione (Chemical Formula 8)

Sodium nitride (179 mg, 2.6 mmol) was added to 2-amino-N-(2,6-dioxopiperidin-3-yl)-6-fluorobenzamide (406 mg, 1.5 mmol) dissolved in acetic acid (12 ml). After stirring at a room temperature for 1.5 hours, the mixture was diluted with water, and the precipitated white products were collected and were washed with water and were dried to obtain 3-(5-fluoro-4-oxobenzo[d][1,2,3]triazin-3(4H)-yl)piperidine-2,6-dione 280 mg.

$^1$H NMR (300 MHz, DMSO-$d_6$) δ 11.21 (s, 1H), 8.26-8.02 (m, 2H), 8.00-7.67 (m, 1H), 6.06-5.81 (m, 1H), 3.08-2.53 (m, 3H), 2.36-2.17 (m, 1H);

MS found (M+H)$^+$ (m/z), 277.09; calcd for $C_{12}H_9FN_4O_3$ m/z, 277.10.

[1-3] Synthesis of 3-(5-((4-methoxybenzyl)amino)-4-oxobenzo[d][1,2,3]triazin-3(4H)-yl)piperidine-2,6-dione (Compound <1-3>)

To the solution of 3-(5-fluoro-4-oxobenzo[d][1,2,3]triazin-3(4H)-yl)piperidine-2,6-dione (50 mg, 0.18 mmol) dissolved in DMF (1 ml), 4-methoxybenzyl amine (47 μl, 0.36 mmol) and DIPEA (62 μl, 0.36 mmol) were added at a room temperature, and it was stirred at 90° C. overnight. The reaction mixture was diluted with water, and then it was extracted with ethyl acetate. The organic layer was dried on anhydrous $Na_2SO_4$, and it was purified by column chromatography to obtain 3-(5-((4-methoxybenzyl)amino)-4-oxobenzo[d][1,2,3]triazin-3(4H)-yl)piperidine-2,6-dione (12 mg, 17%) as a white solid.

$^1$H NMR (300 MHz, $CDCl_3$) δ 8.55 (s, 1H), 8.25 (s, 1H), 7.64 (t, J=8.1 Hz, 1H), 7.29-7.27 (m, 2H), 6.88 (d, J=8.4 Hz, 2H), 6.76 (d, J=8.4 Hz, 1H), 5.76-5.61 (m, 1H), 4.39 (d, J=5.3 Hz, 2H), 3.80 (s, 3H), 3.00-2.71 (m, 3H), 2.49-2.28 (m, 1H);

MS found $(M+H)^+$ (m/z), 394.9; calcd for $C_{20}H_{19}N_5O_4$ m/z, 394.10.

[1-4] Synthesis of 3-(5-amino-4-oxobenzo[d][1,2,3]triazin-3(4H)-yl)piperidine-2,6-dione To 3-(5-((4-methoxybenzyl)amino)-4-oxobenzo[d][1,2,3]triazin-3(4H)-yl)piperidine-2,6-dione solution (10 mg, 0.025 mmol) dissolved in toluene (1 ml), DDQ (6.9 mg, 0.03 mmol) was added at a room temperature, and it was stirred overnight. The reaction mixture was diluted with ethyl acetate and was washed with $NaHCO_3$ (aq). The organic layer was dried on anhydrous $MgSO_4$, and it was purified by column chromatography to obtain a pure compound, 3-(5-amino-4-oxobenzo[d][1,2,3]triazin-3(4H)-yl)piperidine-2,6-dione 1.6 mg (23%) as a white solid.

$^1$H NMR (300 MHz, $CDCl_3$) δ 8.00 (s, 1H), 7.72-7.57 (m, 1H), 7.36 (d, J=7.8 Hz, 2H), 7.01-6.75 (m, 2H), 6.13 (s, 1H), 5.83-5.61 (m, 1H), 3.10-2.67 (m, 3H), 2.46-2.34 (m, 1H);

MS found $(M+H)^+$ (m/z), 274.9; calcd for $C_{12}H_{11}N_5O_3$ m/z, 274.10.

Example 2

Synthesis of 3-(5-nitro-4-oxobenzo[d][1,2,3]triazin-3(4H)-yl)piperidine-2,6-dione (Chemical Formula 9)

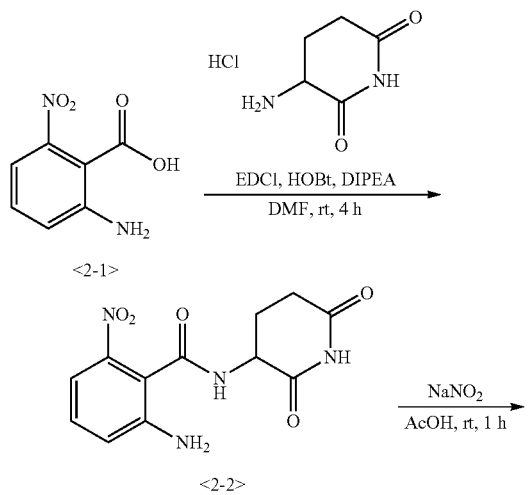

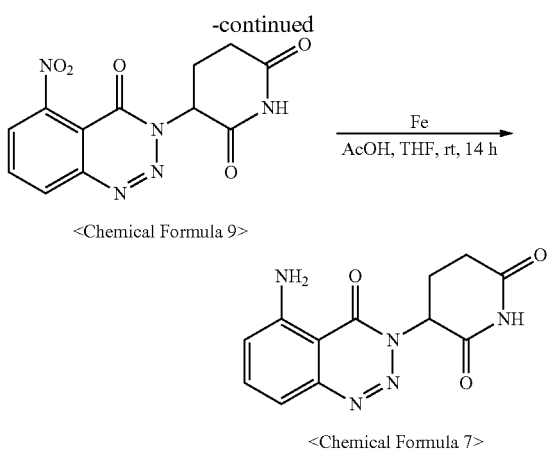

<Chemical Formula 7>

[2-1] Synthesis of 2-amino-N-(2,6-dioxopiperidin-3-yl)-6-nitrobenzamide (Compound <2-2>)

To 2-amino-6-nitrobenzoic acid (7 g, 38 mmol) dissolved in DMF (90 ml), EDCl-HCl (8 g, 42 mmol) and HOBt (6.5 g, 42 mmol) were added. After stirring at a room temperature for 30 minutes, 3-aminopiperidine-2,6-dione hydrochloride (25 g, 152 mmol) and DIPEA (21 ml, 121.6 mmol) were added and it was stirred at a room temperature for 16 hours. The reaction mixture was diluted with water and it was extracted with ethyl acetate. The organic layer was dried on anhydrous $Na_2SO_4$, and then was concentrated under the reduced pressure to obtain 2-amino-N-(2,6-dioxopiperidin-3-yl)-6-nitrobenzamide as a yellow solid (15 g), and it was used in the following step without purification.

$^1$H NMR (300 MHz, DMSO-$d_6$) δ 11.01 (s, 1H), 9.03 (d, J=8.3 Hz, 1H), 7.38-7.14 (m, 2H), 7.06 (d, J=7.2 Hz, 1H), 6.02 (s, 2H), 4.80-4.65 (m, 1H), 2.89-2.58 (m, 2H), 2.33-1.87 (m, 2H).

[2-2] Synthesis of 3-(5-nitro-4-oxobenzo[d][1,2,3]triazin-3(4H)-yl)piperidine-2,6-dione Sodium nitride (2.7 g, 40 mmol) was added to the solution of 2-amino-N-(2,6-dioxopiperidin-3-yl)-6-nitrobenzamide dissolved in acetic acid. After stirring at a room temperature for 1.5 hours, the mixture was diluted with water, and the precipitated white products were collected, and were washed using water, and were dried to obtain 3-(5-nitro-4-oxobenzo[d][1,2,3]triazin-3(4H)-yl)piperidine-2,6-dione 7 g (60%, step 2 yield).

$^1$H NMR (300 MHz, DMSO-$d_6$) δ 11.26 (s, 1H), 8.52 (dd, J=7.6, 1.5 Hz, 1H), 8.45-8.20 (m, 2H), 6.00 (dd, J=12.4, 5.3 Hz, 1H), 3.04-2.87 (m, 1H), 2.78-2.58 (m, 2H), 2.44-2.17 (m, 1H).

[2-3] Synthesis of 3-(5-amino-4-oxobenzo[d][1,2,3]triazin-3(4H)-yl)piperidine-2,6-dione To the solution of 3-(8-nitro-4-oxobenzo[d][1,2,3]triazin-3(4H)-yl)piperidine-2,6-dione (1 g, 3.2 mmol) dissolved in AcOH/THF (25 ml/25 ml), iron (Fe, 1 g) was added and it was stirred at a room temperature overnight. The reaction mixture was filtered and extracted with ethyl acetate. The organic layer was dried on $Na_2SO_4$, and it was purified by column chromatography to obtain 0.5 g (57%) of pure 3-(5-amino-4-oxobenzo[d][1,2,3]triazin-3(4H)-yl)piperidine-2,6-dione as a yellow-green solid.

$^1$H NMR (300 MHz, CDCl$_3$) δ 8.00 (s, 1H), 7.72-7.57 (m, 1H), 7.36 (d, J=7.8 Hz, 2H), 7.01-6.75 (m, 2H), 6.13 (s, 1H), 5.83-5.61 (m, 1H), 3.10-2.67 (m, 3H), 2.46-2.34 (m, 1H);

MS found (M+H)$^+$ (m/z), 274.9; calcd for C$_{12}$H$_{11}$N$_5$O$_3$ m/z, 274.10.

Example 3

Synthesis of 3-(5-chloro-4-oxobenzo[d][1,2,3]triazin-3(4H)-yl)piperidine-2,6-dione (Chemical Formula 10)

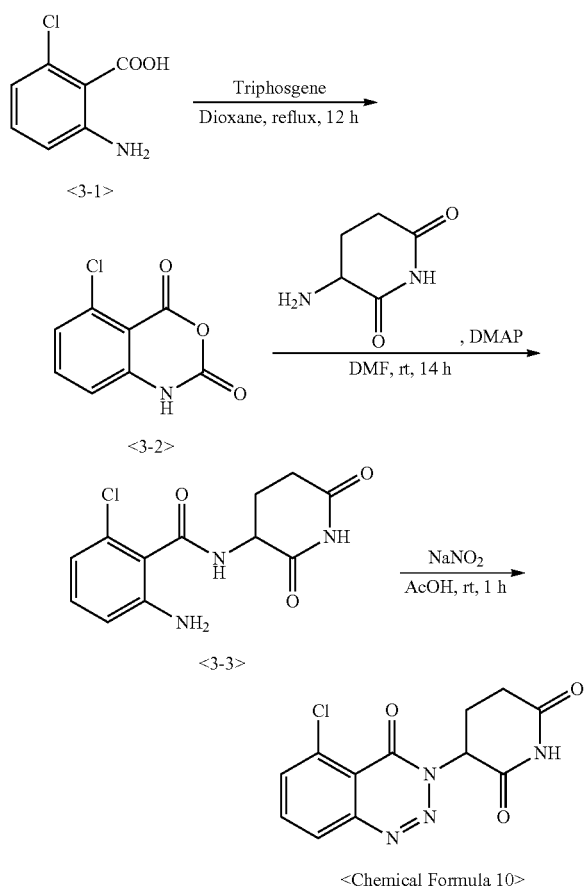

<Chemical Formula 10>

[3-1] Synthesis of 5-chloro-2H-benzo[d][1,3]oxazine-2,4(1H)-dione (Compound <3-2>)

To the solution of 2-amino-6-chlorobenzoic acid (1 g, 5.8 mmol) dissolved in 1,4-dioxane (10 ml), triphosgene (570 mg, 1.9 mmol) was added, and the solution was refluxed for 2 hours. Then, the reactant was cooled on ice. The solid was washed with hexane and was under vacuum drying to obtain a 1.1 g (99%) of pure compound as a brown solid.

$^1$H NMR (300 MHz, DMSO-d$_6$) δ $^1$H NMR (300 MHz, Methanol-d$_4$) δ 7.63 (t, J=8.1 Hz, 1H), 7.40-7.24 (m, 1H), 7.10 (d, J=8.2 Hz, 1H);

MS found (M+H)$^+$ (m/z), 198.09; calcd for C$_8$H$_4$ClNO$_3$ m/z, 198.10.

[3-2] Synthesis of 2-amino-6-chloro-N-(2,6-dioxopiperidin-3-yl)benzamide (Compound <3-3>)

To the solution of 5-chloro-2H-benzo[d][1,3]oxazine-2,4(1H)-dione (200 mg, 1.01 mmol) dissolved in DMF (4 ml), 3-aminopiperidine-2,6-dione (194 mg, 1.5 mmol) and DMAP (12 mg, 0.10 mmol) were added, and the temperature was elevated from 60° C. overnight. The reaction mixture was extracted with ethyl acetate and the organic layer was dried on Na$_2$SO$_4$. The crude compound was obtained as a blue solid (75 mg), and this was used in the next step without further purification.

MS found (M+H)$^+$ (m/z), 282.09; calcd for C$_{12}$H$_9$ClN$_4$O$_3$ m/z, 282.10.

[3-3] Synthesis of 3-(5-chloro-4-oxobenzo[d][1,2,3]triazin-3(4H)-yl)piperidine-2,6-dione To the solution of 2-amino-6-chloro-N-(2,6-dioxopiperidin-3-yl)benzamide (75 mg, 0.26 mmol) dissolved in acetic acid (2 ml), NaNO$_2$ (31 mg, 0.45 mmol) was added, and it was stirred at a room temperature for 1 hour. The reaction mixture was diluted with water and the precipitated product was collected to obtain a pure compound of 18 mg (24%) as a white solid.

$^1$H NMR (300 MHz, DMSO-d$_6$) δ 11.22 (s, 1H), 8.21 (d, J=7.9 Hz, 1H), 8.12-8.01 (m, 2H), 6.02-5.88 (m, 1H), 3.03-2.88 (m, 1H), 2.84-2.60 (m, 2H), 2.42-2.14 (m, 1H);

MS found (M+H)$^+$ (m/z), 293.09; calcd for C$_{12}$H$_9$ClN$_4$O$_3$ m/z, 293.10.

Example 4

Synthesis of 3-(5-methyl-4-oxobenzo[d][1,2,3]triazin-3(4H)-yl)piperidine-2,6-dione (Chemical Formula 11)

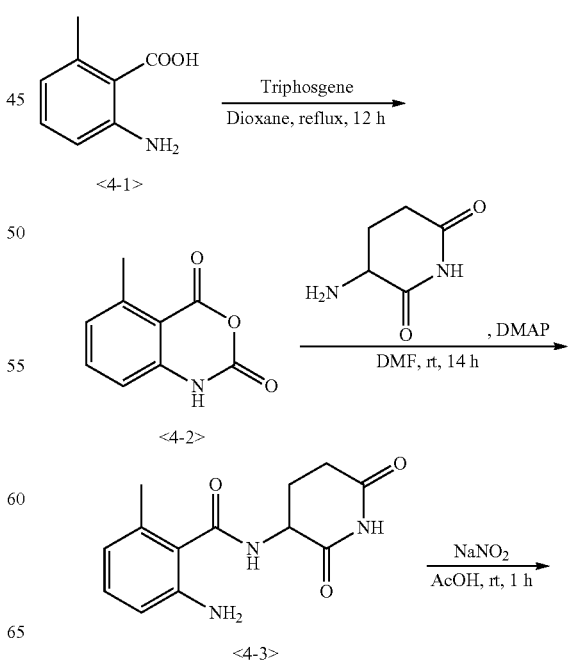

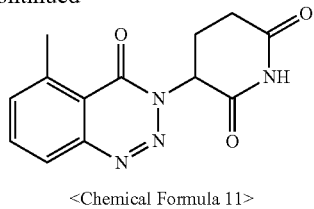

<Chemical Formula 11>

[4-1] Synthesis of 5-methyl-2H-benzo[d][1,3]oxazine-2,4(1H)-dione (Compound <4-2>)

To the solution of 2-amino-6-methylbenzoic acid (876 mg, 5.8 mmol) dissolved in 1,4-dioxane (10 ml), triphosgene (570 mg, 1.9 mmol) was added, and the solution was refluxed for 2 hours. Then, the solution was cooled on ice. The solid was washed with hexane and was under vacuum drying to obtain a pure compound of 880 mg (85%) as a brown solid.
$^1$H NMR (300 MHz, CDCl$_3$) δ 9.02 (brs, 1H), 7.56 (t, J=7.8 Hz, 1H), 7.12 (d, J=7.7 Hz, 1H), 6.94 (d, J=8.1 Hz, 1H), 2.77 (s, 3H).

[4-2] Synthesis of 2-amino-N-(2,6-dioxopiperidin-3-yl)-6-methylbenzamide (Compound <4-3>)

To the solution of 5-methyl-2H-benzo[d][1,3]oxazine-2,4[1h]-dione (178 mg, 1.01 mmol) dissolved in DMF (4 ml), 3-aminopiperidine-2,6-dione (194 mg, 1.5 mmol) and DMAP (12 mg, 0.104 mmol) were added, and the mixture was heated at 60° C. overnight. The reaction mixture was extracted with ethyl acetate, and the organic layer was dried on Na$_2$SO$_4$. The crude compound was obtained as a blue solid (50 mg), and this was used in the next step without further purification.

[4-3] Synthesis of 3-(5-methyl-4-oxobenzo[d][1,2,3]triazin-3(4H)-yl)piperidine-2,6-dione To the solution of 2-amino-N-(2,6-dioxopiperidin-3-yl)-6-methylbenzamide (50 mg, 0.19 mmol) dissolved in acetic acid (2 ml), NaNO$_2$ (22 mg, 0.32 mmol) was added, and it was stirred at a room temperature for 1 hour. The reaction mixture was diluted with water, and the precipitated product was collected, and a pure compound of 16 mg (31%) was obtained as a brown solid.
$^1$H NMR (300 MHz, DMSO-d$_6$) δ 11.19 (s, 1H), 8.07 (d, J=7.8 Hz, 1H), 7.99 (t, J=7.7 Hz, 1H), 7.75 (d, J=7.1 Hz, 1H), 5.99-5.87 (m, 1H), 3.03-2.85 (m, 1H), 2.83 (s, 3H), 2.76-2.56 (m, 2H), 2.35-2.19 (m, 1H).

Example 5

Synthesis of 3-(6-chloro-4-oxobenzo[d][1,2,3]triazin-3(4H)-yl)piperidine-2,6-dione (Chemical Formula 12)

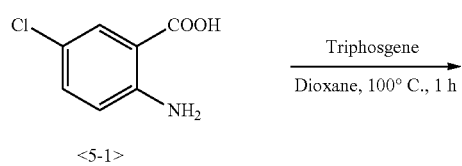

<5-1>

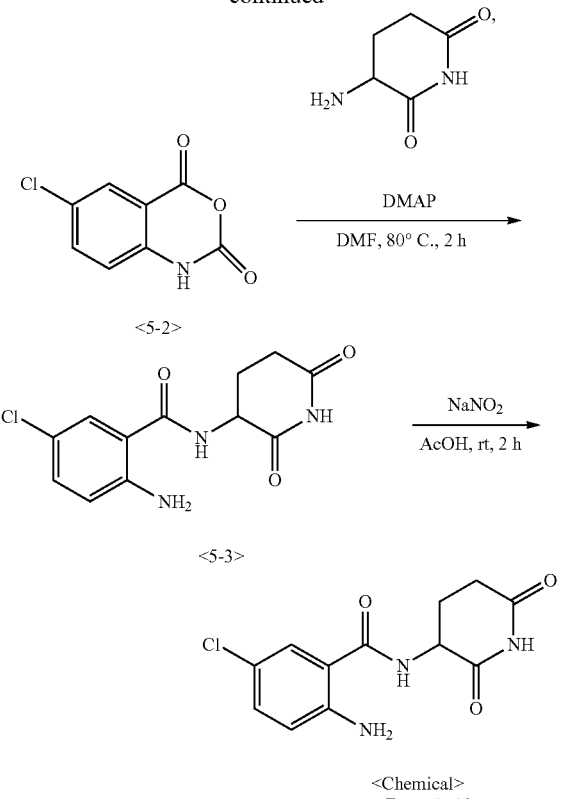

<Chemical Formula 12>

[5-1] Synthesis of 6-chloro-2H-benzo[d][1,3]oxazine-2,4(1H)-dione (Compound <5-2>)

To the solution of 2-amino-5-chlorobenzoic acid (500 mg, 2.0 mmol) dissolved in 1,4-dioxane (5 ml), triphosgene (285 mg, 0.96 mmol) was added and the solution was refluxed for 2 hours. The reaction mixture was cooled in an ice container. The solid was washed and was under vacuum drying to obtain a pure compound of 400 mg (70%) as a brown solid.
$^1$H NMR (300 MHz, DMSO-d$_6$) δ 11.88 (s, 1H), 7.89 (d, J=2.4 Hz, 1H), 7.80 (dd, J=8.7, 2.5 Hz, 1H), 7.19 (d, J=8.7 Hz, 1H).

[5-2] Synthesis of 2-amino-5-chloro-N-(2,6-dioxopiperidin-3-yl)benzamide (Compound <5-3>)

To the solution of 6-chloro-2H-benzo[d][1,3]oxazine-2,4(1H)-dione (200 mg, 1.01 mmol) dissolved in DMF (3 ml), 3-aminopiperidine-2,6-dione (129 mg, 1.01 mmol) and DMAP (12.3 mg, 0.101 mmol) were added, and the reaction mixture solution was heated at 60° C. overnight. The reaction mixture was extracted with ethyl acetate, and the organic layer was dried on Na$_2$SO$_4$. The crude compound was obtained as a blue solid (70 mg), and this was used in the next step without further purification.

[5-3] Synthesis of 3-(6-chloro-4-oxobenzo[d][1,2,3]triazin-3(4H)-yl)piperidine-2,6-dione To the solution of 2-amino-N-(2,6-dioxopiperidin-3-yl)-6-methylbenzamide (50 mg, 0.19 mmol) dissolved in acetic acid (3 ml), NaNO$_2$ (22 mg, 0.32 mmol) was added and it was stirred at a room temperature for 1 hour. The reaction mixture was diluted with water, and the precipitated product was collected to obtain a pure compound of 28 mg (39%) as a brown solid.

$^1$H NMR (300 MHz, DMSO-d$_6$) δ 11.21 (br s, 1H), 8.38-8.25 (m, 2H), 8.24-8.12 (m, 1H), 6.00 (dd, J=12.2, 5.4 Hz, 1H), 3.05-2.91 (m, 1H), 2.83-2.58 (m, 2H), 2.39-2.15 (m, 2H).

Example 6

Synthesis of 3-(6-bromo-4-oxobenzo[d][1,2,3]triazin-3(4H)-yl)piperidine-2,6-dione (Chemical Formula 13)

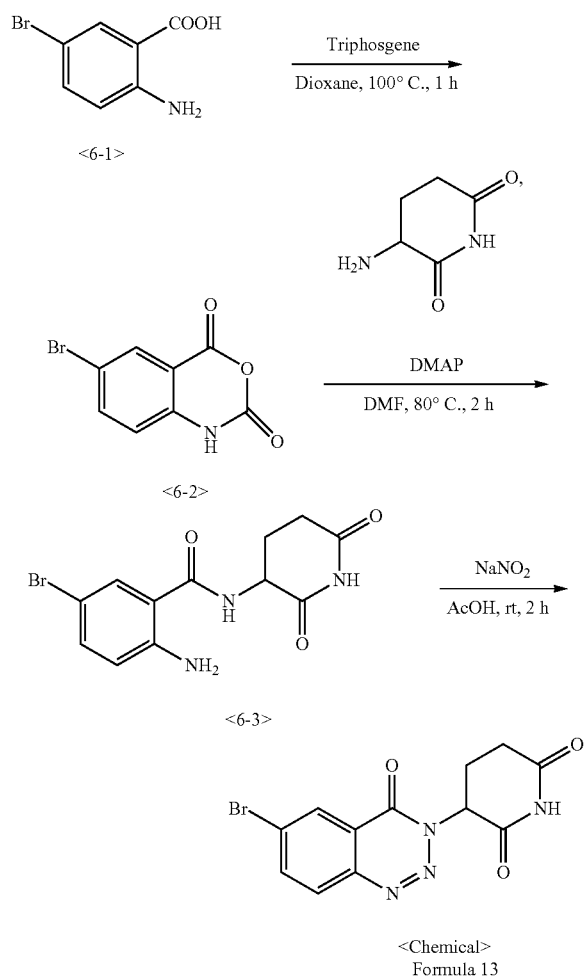

[6-1] Synthesis of 6-bromo-2H-benzo[d][1,3]oxazine-2,4(1H)-dione (Compound <6-2>)

To the solution of 2-amino-5-bromobenzoic acid (626 mg, 2.9 mmol) dissolved in 1,4-dioxane (5 ml), triphosgene (285 mg, 0.96 mmol) was added, and the solution was refluxed for 2 hours. Then, the reaction mixture was cooled on ice. The solid was washed with hexane and was under vacuum drying to obtain a pure compound of brown solid of 630 mg (90%).

$^1$H NMR (300 MHz, DMSO-d$_6$) δ 11.87 (s, 1H), 8.00 (d, J=2.3 Hz, 1H), 7.91 (dd, J=8.7, 2.3 Hz, 1H), 7.11 (d, J=8.7 Hz, 1H).

[6-2] Synthesis of 2-amino-5-bromo-N-(2,6-dioxopiperidin-3-yl)benzamide (Compound <6-3>)

To the solution of 6-bromo-2H-benzo[d][1,3]oxazine-2,4(1H)-dione (244 mg, 1.01 mmol) dissolved in DMF (3 ml), 3-aminopiperidine-2,6-dione (129 mg, 1.01 mmol) and DMAP (12.3 mg, 0.101 mmol) were added, and the mixture was heated at 60° C. overnight. The reaction mixture was extracted with ethyl acetate, and the organic layer was dried on Na$_2$SO$_4$. The crude compound was obtained as a blue solid (80 mg), and this was used in the next step without further purification.

[6-3] Synthesis of 3-(6-bromo-4-oxobenzo[d][1,2,3]triazin-3(4H)-yl)piperidine-2,6-dione To the solution of 2-amino-5-bromo-N-(2,6-dioxopiperidin-3-yl)benzamide (80 mg, 0.25 mmol) dissolved in acetic acid (3 ml), NaNO$_2$ (28 mg, 0.41 mmol) was added, and it was stirred at a room temperature for 1 hour. The reaction mixture was diluted with water, and the precipitated product was collected to obtain a pure compound of 42 mg (51%) as an ivory solid.

$^1$H NMR (300 MHz, DMSO-d$_6$) δ 11.21 (br s, 1H), 8.40 (d, J=2.0 Hz, 1H), 8.32 (dd, J=8.6, 2.2 Hz, 1H), 8.21 (d, J=8.6 Hz, 1H), 6.07-5.99 (m, 1H), 3.00-2.85 (m, 1H), 2.78-2.55 (m, 2H), 2.34-2.16 (m, 1H).

Example 7

Synthesis of 3-(6-iodo-4-oxobenzo[d][1,2,3]triazin-3(4H)-yl)piperidine-2,6-dione (Chemical Formula 14)

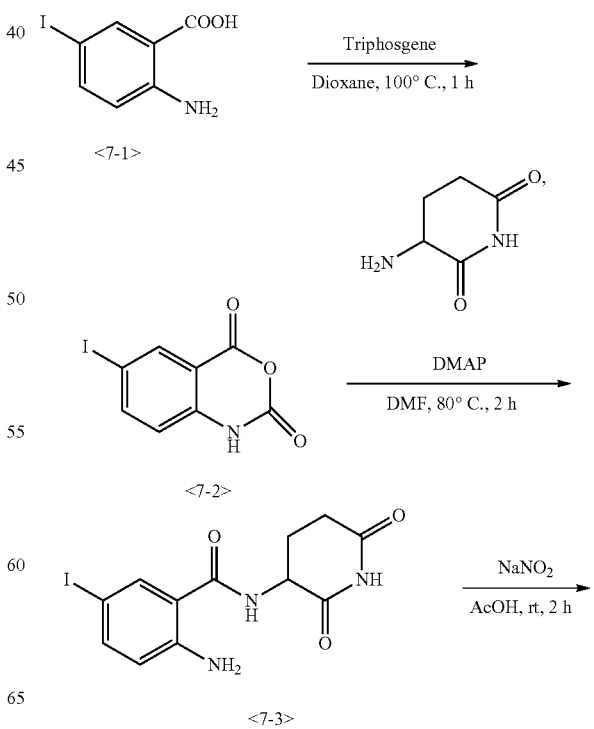

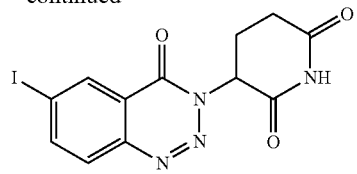

<Chemical>
Formula 14

[7-1] Synthesis of 6-iodo-2H-benzo[d][1,3]oxazine-2,4(1H)-dione (Compound <7-2>)

To the solution of 2-amino-5-iodobenzoic acid (762 mg, 2.9 mmol) dissolved in 1,4-dioxane (5 ml), triphosgene (285 mg, 0.96 mmol) was added, and the solution was refluxed for 2 hours. Then, the reaction mixture was cooled on ice. The solid was washed with hexane and was under vacuum drying to obtain a pure compound of brown solid of 680 mg (81%).
$^1$H NMR (300 MHz, DMSO-d$_6$) δ 11.83 (s, 1H), 8.14 (d, J=2.0 Hz, 1H), 8.03 (dd, J=8.5, 2.0 Hz, 1H), 6.97 (d, J=8.6 Hz, 1H).

[7-2] Synthesis of 2-amino-N-(2,6-dioxopiperidin-3-yl)-5-iodobenzamide (Compound <7-3>)

To the solution of 6-iodo-2H-benzo[d][1,3]oxazine-2,4(1H)-dione (291 mg, 1.01 mmol) dissolved in DMF (3 ml), 3-aminopiperidine-2,6-dione (129 mg, 1.01 mmol) and DMAP (12.3 mg, 0.101 mmol) were added, and the mixture was heated at 60° C. overnight. The reaction mixture was extracted with ethyl acetate, and the organic layer was dried on Na$_2$SO$_4$. The crude compound was obtained as a blue solid (80 mg), and this was used in the next step without further purification.

[7-3] Synthesis of 3-(6-iodo-4-oxobenzo[d][1,2,3]triazin-3(4H)-yl)piperidine-2,6-dione To the solution of 2-amino-N-(2,6-dioxopiperidin-3-yl)-5-iodobenzamide (130 mg, 0.35 mmol) dissolved in acetic acid (5 ml), NaNO$_2$ (40 mg, 0.59 mmol) was added, and it was stirred at a room temperature for 1 hour. The reaction mixture was diluted with water, and the precipitated product was collected to obtain a pure compound of 20 mg (15%) as an ivory solid.
$^1$H NMR (300 MHz, DMSO-d$_6$) δ 11.20 (br s, 1H), 8.58 (s, 1H), 8.47 (d, J=8.3 Hz, 1H), 8.02 (d, J=8.6 Hz, 1H), 6.14-5.84 (m, 1H), 3.02-2.83 (m, 1H), 2.85-2.63 (m, 2H), 2.40-2.01 (m, 1H).

Example 8

Synthesis of 3-(8-bromo-6-methyl-4-oxobenzo[d][1,2,3]triazin-3(4H)-yl)piperidine-2,6-dione (Chemical Formula 15)

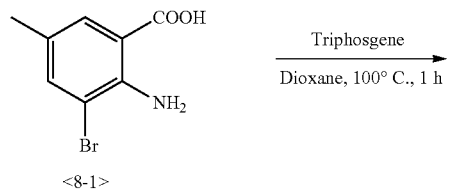

<8-1>

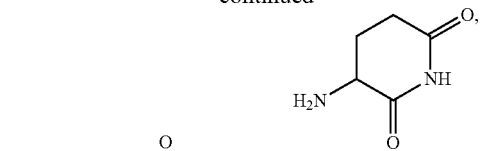

<8-2>

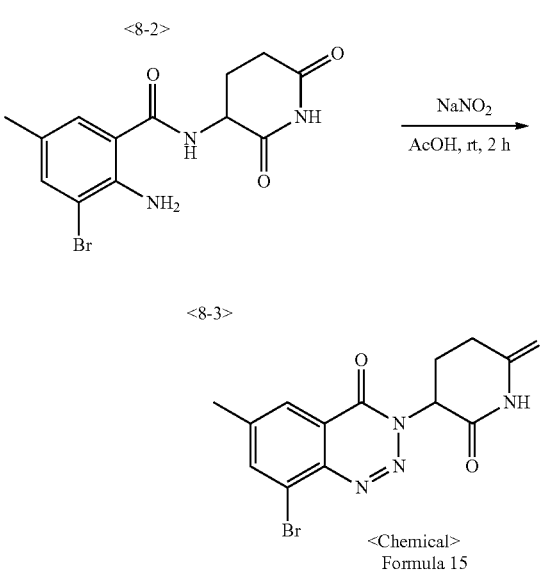

<8-3>

<Chemical>
Formula 15

[8-1] Synthesis of 8-bromo-6-methyl-2H-benzo[d][1,3]oxazine-2,4(1H)-dione (Compound <8-2>)

To the solution of 2-amino-3-bromo-5-methylbenzoic acid (667 mg, 2.9 mmol) dissolved in 1,4-dioxane (5 ml), triphosgene (285 mg, 0.96 mmol) was added, and the solution was refluxed for 2 hours. Then, the reaction mixture was cooled on ice. The solid was washed with hexane and was under vacuum drying to obtain a pure compound of brown solid of 720 mg (97%).
$^1$H NMR (300 MHz, DMSO-d$_6$) δ 11.01 (s, 1H), 7.89 (d, J=1.4 Hz, 1H), 7.77 (s, 1H), 3.57 (s, 3H).

[8-2] Synthesis of 2-amino-3-bromo-N-(2,6-dioxopiperidin-3-yl)-5-methylbenzamide (Compound <8-3>)

To the solution of 8-bromo-6-methyl-2H-benzo[d][1,3]oxazine-2,4(1H)-dione (258 mg, 1.01 mmol) dissolved in DMF (3 ml), 3-aminopiperidine-2,6-dione (129 mg, 1.01 mmol) and DMAP (12.3 mg, 0.101 mmol) were added, and the mixture was heated at 60° C. overnight. The reaction mixture was extracted with ethyl acetate, and the organic layer was dried on Na$_2$SO$_4$. The crude compound was obtained as a blue solid (170 mg), and this was used in the next step without further purification.

[8-3] Synthesis of 3-(8-bromo-6-methyl-4-oxobenzo[d][1,2,3]triazin-3(4H)-yl)piperidine-2,6-dione To the solution of 2-amino-3-bromo-N-(2,6-dioxopiperidin-3-yl)-5-methylbenzamide (170 mg, 0.5 mmol) dissolved in acetic acid (6 ml), NaNO$_2$ (59 mg, 0.85 mmol) was added, and it was stirred at a room temperature for 1 hour. The reaction mixture was diluted with water, and the precipitated was collected to obtain a pure compound of 120 mg (69%) as an ivory solid.

$^1$H NMR (300 MHz, DMSO-d$_6$) δ 11.21 (br s, 1H), 8.31 (d, J=1.3 Hz, 1H), 8.13-8.03 (m, 1H), 6.00 (dd, J=12.1, 5.3 Hz, 1H), 2.99-2.91 (m, 1H), 2.78-2.59 (m, 1H), 2.55 (s, 2H), 2.40-2.21 (m, 1H).

Example 9

Synthesis of 3-(2,6-dioxopiperidin-3-yl)-4-oxo-3,4-dihydrobenzo[d][1,2,3]triazin-6-carbonitrile (Chemical Formula 16)

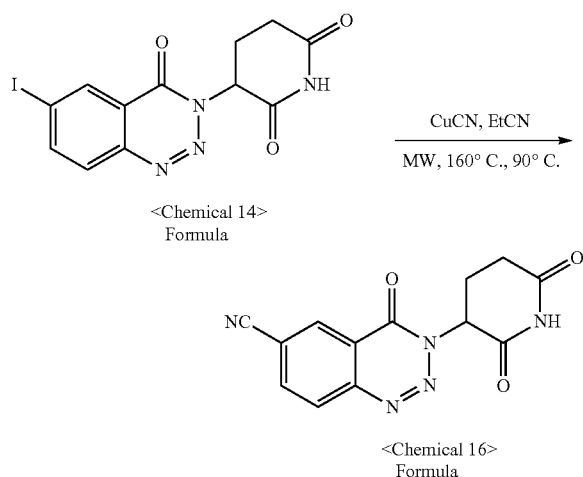

<Chemical 14>
Formula

<Chemical 16>
Formula 3-(6-Iodo-4-oxobenzo[d][1,2,3]triazin-3(4H)-yl)piperidine-2,6-dione (10 mg, 0.038 mmol, synthesized in Example 7) dissolved in propionitrile (0.04 ml) was added, and it was stirred using a microwave reactor for 1 hour. The mixture was filtered with DCM, and was concentrated, and was purified by column chromatography to obtain a pure compound of 4.1 mg (40%) as a pink solid.

$^1$H NMR (300 MHz, CDCl$_3$) δ 8.71 (s, 1H), 8.35 (d, J=8.4 Hz, 1H), 8.22 (dd, J=8.4, 1.5 Hz, 1H), 8.12 (s, 1H), 5.88 (dd, J=12.2, 5.3 Hz, 1H), 3.15-2.79 (m, 3H), 2.60-2.39 (m, 1H).

Example 10

Synthesis of 3-(5-iodo-4-oxobenzo[d][1,2,3]triazin-3(4H)-yl)piperidine-2,6-dione (Chemical Formula 17)

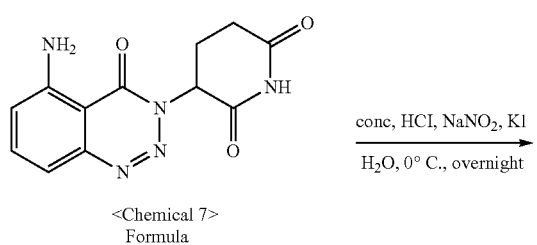

<Chemical 7>
Formula

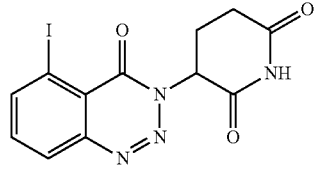

<Chemical 17>
Formula

To the solution of 3-(5-amino-4-oxobenzo[d][1,2,3]triazin-3(4H)-yl)piperidine-2,6-dione (10 mg, 0.036 mmol, synthesized in Example 1) dissolved in concentrated hydrochloric acid of 0.12 ml, NaNO$_2$ (5 mg, 0.073 mmol) comprised in 0.02 ml water was added at 0° C. under the presence of argon gas. After the addition, the solution was stirred for 30 minutes and KI (potassium iodide, 12 mg, 0.073 mmol) dissolved in 10 ml water was added at 0° C. under the presence of argon gas. Then, it was stirred overnight. The solution was diluted with 100 ml AcOEt, and was diluted again with 100 ml water. The aqueous layer was separated and was extracted with EtOAc. The organic layer was combined and it was washed with salt water, and it was dried on Na$_2$SO$_4$, and was concentrated under vacuum. The residues were purified by chromatography on gel to obtain 3-(5-iodo-4-oxobenzo[d][1,2,3]triazin-3(4H)-yl)piperidine-2,6-dione.

$^1$H NMR (300 MHz, MeOD) δ 8.50 (d, J=7.7 Hz, 1H), 8.20 (d, J=8.2 Hz, 1H), 7.69 (t, J=7.5 Hz, 1H), 6.04-5.82 (m, 1H), 3.04-2.75 (m, 3H), 2.49-2.21 (m, 1H).

Example 11

Synthesis of 3-(4-oxo-6-(trifluoromethoxy)benzo[d][1,2,3]triazin-3(4H)-yl)piperidine-2,6-dione (Chemical Formula 18)

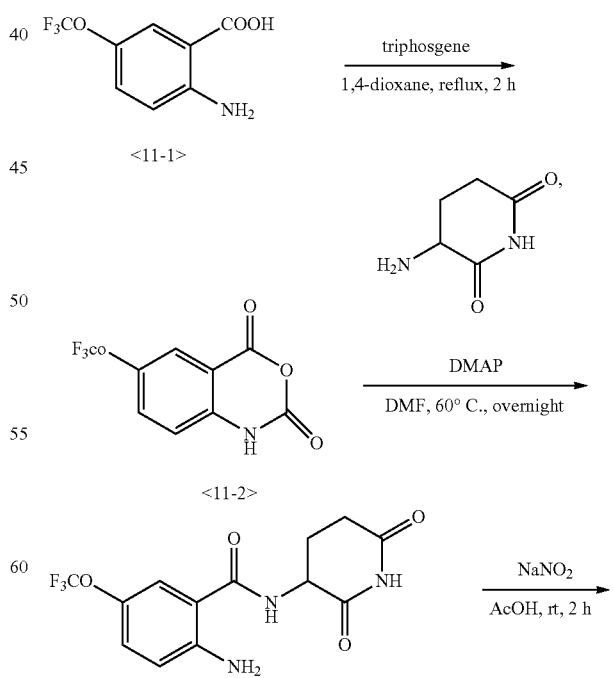

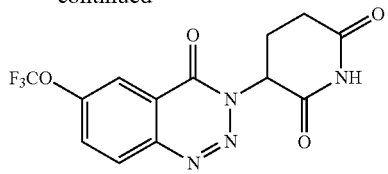

<Chemical>
Formula 18

[11-1] Synthesis of 6-(trifluoromethoxy)-2H-benzo[d][1,3]oxazine-2,4(1H)-dione (Compound <11-2>)

To the solution of 2-amino-5-(trifluoromethoxy)benzoic acid (0.2 g, 0.904 mmol) dissolved in 1,4-dioxane (5 ml), triphosgene (0.09 g, 0.3 mmol) was added, and the solution was refluxed for 2 hours. The reaction mixture was cooled in an ice container. The solid was washed with hexane and was under vacuum drying to obtain a pure compound of 0.2 g (90%) as an ivory solid.
$^1$H NMR (300 MHz, DMSO-$d_6$) δ 11.92 (s, 1H), 7.82-7.76 (m, 2H), 7.25 (d, J=8.8 Hz, 1H).

[11-2] Synthesis of 2-amino-N-(2,6-dioxopiperidin-3-yl)-5-(trifluoromethoxy)benzamide (Compound <11-3>)

To 6-(trifluoromethoxy)-2H-benzo[d][1,3]oxazine-2,4(1H)-dione (0.2 g, 0.81 mmol) dissolved in DMF (2 ml), 3-aminopiperidine-2,6-dione (0.156 g, 1.22 mmol) and DMAP (0.015 g, 0.122 mmol) were added and the mixture was heated at 60° C. overnight. The reaction mixture was extracted with ethyl acetate, and the organic layer was dried on Na$_2$SO$_4$. The crude compound was collected as a blue solid (0.2 g), and this was used in the next step without further purification.

[11-3] Synthesis of 3-(4-oxo-6-(trifluoromethoxy)benzo[d][1,2,3]triazin-3(4H)-yl)piperidine-2,6-dione To the solution of 2-amino-N-(2,6-dioxopiperidin-3-yl)-5-(trifluoromethoxy)benzamide (0.1 g, 0.32 mmol) dissolved in acetic acid (2 ml), NaNO$_2$ (37 mg, 0.54 mmol) was added, and it was stirred at a room temperature for 1 hour. The reaction mixture was diluted with water, and the precipitated product was collected to obtain a pure compound of 76 mg (70%) as an ivory solid.
$^1$H NMR (500 MHz, CD$_3$OD) δ 8.36 (d, J=8.9 Hz, 1H), 8.15 (s, 1H), 7.99 (d, J=8.8 Hz, 1H), 6.01-5.97 (m, 1H), 2.89-2.83 (m, 3H), 2.41-2.37 (m, 1H);
MS found (M+H)$^+$ (m/z), 342.8; calcd for C$_{13}$H$_9$F$_3$N$_4$O$_4$ m/z, 342.06.

Example 12

Synthesis of 3-(6-methoxy-4-oxobenzo[d][1,2,3]triazin-3(4H)-yl)piperidine-2,6-dione (Chemical Formula 19)

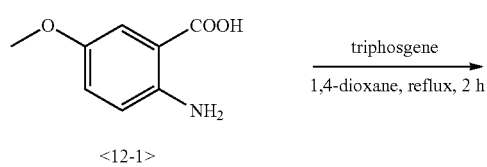

<12-1>

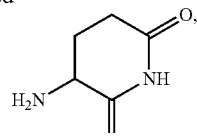

<12-2>

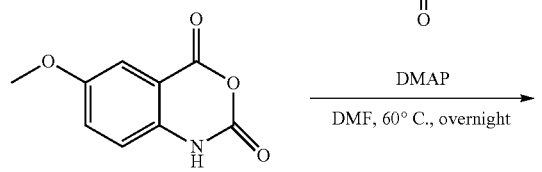

<12-3>

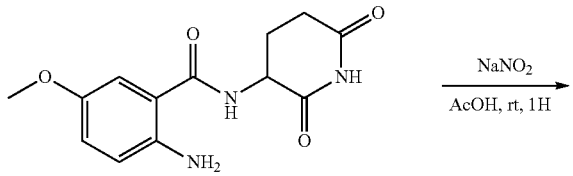

<Chemical>
Formula 19

[12-1] Synthesis of 6-methoxy-2H-benzo[d][1,3]oxazine-2,4(1H)-dione (Compound <12-2>)

To the solution of 2-amino-5-methoxybenzoic acid (0.5 g, 3 mmol) dissolved in 1,4-dioxane (5 ml), triphosgene (0.3 g, 1 mmol) was added, and the solution was refluxed for 2 hours. The reaction mixture was cooled in an ice container. The solid was washed with hexane and was under vacuum drying to obtain a pure compound of 0.53 g (92%) as a brown solid.
$^1$H NMR (300 MHz, DMSO-$d_6$) δ 11.61 (s, 1H), 7.38 (dd, J=8.8, 2.9 Hz, 1H), 7.34 (d, J=2.8 Hz, 1H), 7.11 (d, J=8.8 Hz, 1H), 3.80 (s, 3H).

[12-2] Synthesis of 2-amino-N-(2,6-dioxopiperidin-3-yl)-5-methoxybenzamide (Compound <12-3>)

To 6-methoxy-2H-benzo[d][1,3]oxazine-2,4(1H)-dione (0.2 g, 1.04 mmol) dissolved in DMF (2 ml), 3-aminopiperidine-2,6-dione (0.2 g, 1.56 mmol) and DMAP (0.013 g, 0.104 mmol) were added, and the mixture was heated at 60° C. overnight. The reaction mixture was extracted with ethyl acetate, and the organic layer was dried on Na$_2$SO$_4$. The crude compound was obtained as a blue solid (0.2 g) and this was used in the next step without further purification.

[12-3] Synthesis of 3-(6-methoxy-4-oxobenzo[d][1,2,3]triazin-3(4H)-yl)piperidine-2,6-dione To the solution of 2-amino-N-(2,6-dioxopiperidin-3-yl)-5-methoxybenzamide (0.13 g, 0.5 mmol) dissolved in acetic acid (2 ml), NaNO$_2$ (60 mg, 0.85 mmol) was added, and it was stirred at a room temperature for 1 hour. The reaction mixture was diluted with water and the precipitated product was collected to obtain a pure compound of 42 mg (30%) as a pink solid.

$^1$H NMR (300 MHz, DMSO-d$_6$) δ 11.20 (s, 1H), 8.20 (d, J=8.9 Hz, 1H), 7.69 (dd, J=8.9, 2.9 Hz, 1H), 7.61 (d, J=2.8 Hz, 1H), 6.00-5.94 (m, 1H), 3.04-2.91 (m, 1H), 2.77-2.63 (m, 2H), 2.31-2.23 (m, 1H);

MS found (M+H)$^+$ (m/z), 288.9; calcd for C$_{13}$H$_{12}$N$_4$O$_4$ m/z, 288.09.

Example 13

Synthesis of N-(3-(2,6-dioxopiperidin-3-yl)-4-oxo-3,4-dihydrobenzo[d][1,2,3]triazin-5-yl)acetamide (Chemical Formula 20)

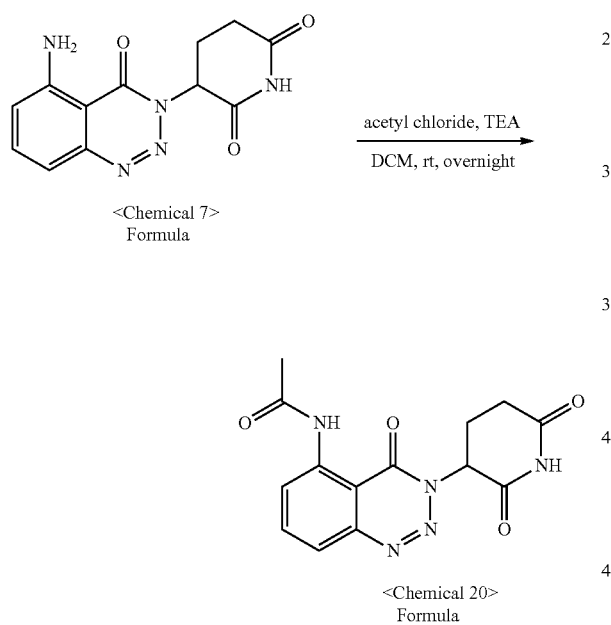

To the solution of 3-(5-amino-4-oxobenzo[d][1,2,3]triazin-3(4H)-yl)piperidine-2,6-dione (22 mg, 0.081 mmol, synthesized in Example 1) dissolved in DCM (5 ml), trimethylamine (0.013 ml, 0.09 mmol) and acetyl chloride (0.006 ml, 0.081 mmol) were added at 0° C., and the mixture was stirred at a room temperature overnight. The reaction mixture was extracted with DCM. The organic layer was dried on Na$_2$SO$_4$, and was purified by column chromatography to obtain a pure compound of 0.012 g (47%) as a white solid.

$^1$H NMR (300 MHz, CDCl$_3$) δ 11.46 (s, 1H), 9.06 (d, J=8.5 Hz, 1H), 8.06 (s, 1H), 7.96 (t, J=8.2 Hz, 1H), 7.86 (d, J=8.1 Hz, 1H), 5.76-5.71 (m, 1H), 3.03-2.84 (m, 1H), 2.44-2.37 (m, 1H), 2.28 (s, 3H);

MS found (M+H)$^+$ (m/z), 315.9; calcd for C$_{14}$H$_{13}$N$_5$O$_4$ m/z, 315.10.

Example 14

Synthesis of 3-(8-nitro-4-oxobenzo[d][1,2,3]triazin-3(4H)-yl)piperidine-2,6-dione (Chemical Formula 21) and 3-(8-amino-4-oxobenzo[d][1,2,3]triazin-3(4H)-yl)piperidine-2,6-dione (Chemical Formula 22)

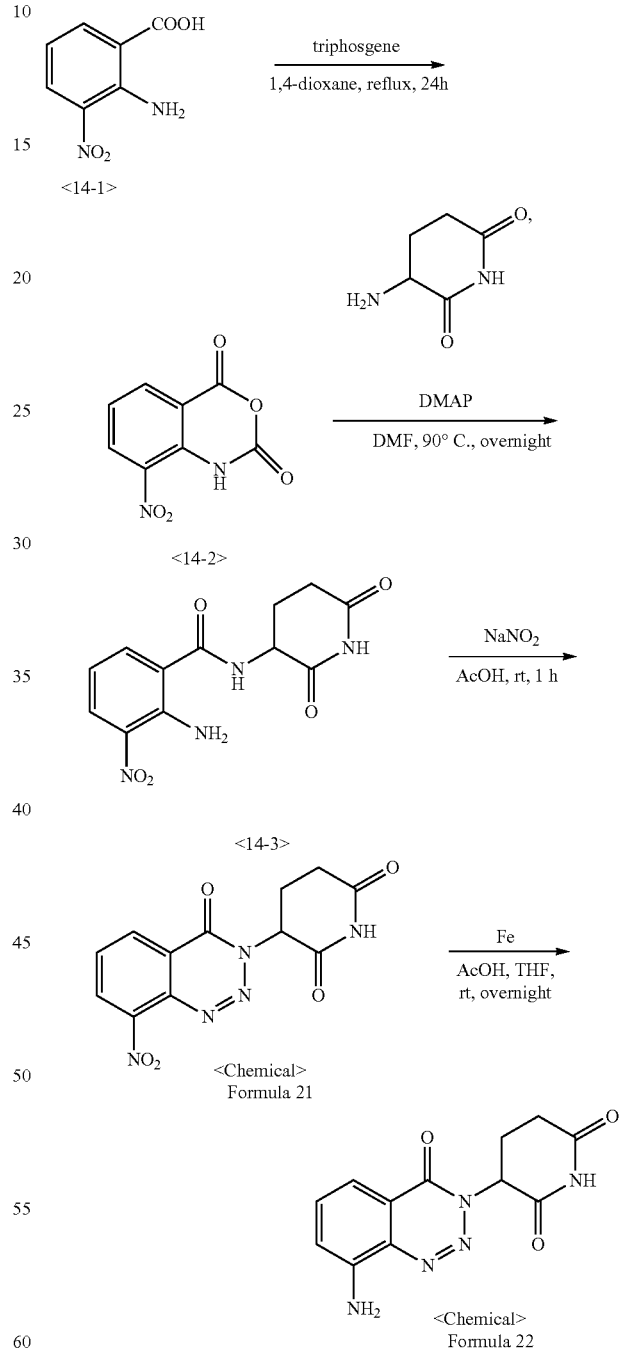

[14-1] Synthesis of 8-nitro-2H-benzo[d][1,3]oxazine-2,4(1H)-dione (Compound <14-2>)

To the solution of 2-amino-3-nitrobenzoic acid (1.0 g, 5.5 mmol) dissolved in 1,4-dioxane (10 ml), triphosgene (0.54 g, 1.82 mmol) was added and the solution was refluxed overnight. The reaction mixture was cooled in an ice container. The solid was washed with hexane and was under vacuum drying to obtain a pure compound of 0.945 g (83%) as a yellow solid.

$^1$H NMR (300 MHz, DMSO-d$_6$) δ 11.13 (s, 1H), 8.49 (d, J=8.2 Hz, 1H), 8.34 (d, J=6.6 Hz, 1H), 7.43 (t, J=8.0 Hz, 1H).

[14-2] Synthesis of 2-amino-N-(2,6-dioxopiperidin-3-yl)-3-nitrobenzamide (Compound <14-3>)

To 8-nitro-2H-benzo[d][1,3]oxazine-2,4(1H)-dione (0.216 g, 1.04 mmol) dissolved in DMF (2 ml), 3-aminopiperidine-2,6-dione (0.2 g, 1.56 mmol) and DMAP (0.013 g, 0.104 mmol) were added, and the mixture was heated at 90° C. overnight. The reaction mixture was extracted with ethyl acetate, and the organic layer was dried on Na$_2$SO$_4$. The crude compound was obtained as a yellow solid (0.2 g), and this was used in the next step without further purification.

[14-3] Synthesis of 3-(8-nitro-4-oxobenzo[d][1,2,3]triazin-3(4H)-yl)piperidine-2,6-dione To the solution of 2-amino-N-(2,6-dioxopiperidin-3-yl)-3-nitrobenzamide (0.128 g, 0.46 mmol) dissolved in acetic acid (2 ml), NaNO$_2$ (54 mg, 0.78 mmol) was added, and it was stirred at a room temperature for 1 hour. The reaction mixture was diluted with water, and the precipitated product was collected to obtain a pure compound of 55 mg (39%) as a yellow solid.

$^1$H NMR (300 MHz, DMSO-d$_6$) δ 11.26 (s, 1H), 8.64 (d, J=7.8 Hz, 1H), 8.53 (d, J=8.2 Hz, 1H), 8.14 (t, J=8.0 Hz, 1H), 6.09-6.03 (m, 1H), 3.03-2.93 (m, 1H), 2.73-2.65 (m, 2H), 2.33-2.27 (m, 2H);

MS found (M+H)$^+$ (m/z), 303.8; calcd for C$_{12}$H$_9$N$_5$O$_5$ m/z, 303.06.

[14-4] Synthesis of 3-(8-amino-4-oxobenzo[d][1,2,3]triazin-3(4H)-yl)piperidine-2,6-dione To the solution of 3-(8-nitro-4-oxobenzo[d][1,2,3]triazin-3(4H)-yl)piperidine-2,6-dione (0.02 g, 0.066 mmol) dissolved in AcOH/THF (2 ml/2 ml), iron (Fe, 0.02 g) was added, and it was stirred at a room temperature overnight. The reaction mixture was filtered and was extracted with ethyl acetate. The organic layer was dried Na$_2$SO$_4$, and was purified by column chromatography to obtain a pure compound of 0.004 g (22%) as a yellow-green solid.

$^1$H NMR (300 MHz, DMSO-d$_6$) δ 11.16 (s, 1H), 7.56 (t, J=7.9 Hz, 1H), 7.23-7.17 (m, 2H), 6.69 (s, 2H), 5.92-5.86 (m, 1H), 3.02-2.91 (m, 1H), 2.74-2.61 (m, 1H), 2.29-2.20 (m, 1H);

MS found (M+H)$^+$ (m/z), 274.0; calcd for C$_{12}$H$_{11}$N$_5$O$_3$ m/z, 273.09.

Example 15

Synthesis of N-(3-(2,6-dioxopiperidin-3-yl)-4-oxo-3,4-dihydrobenzo[d][1,2,3]triazin-6-yl)acetamide (Chemical Formula 23)

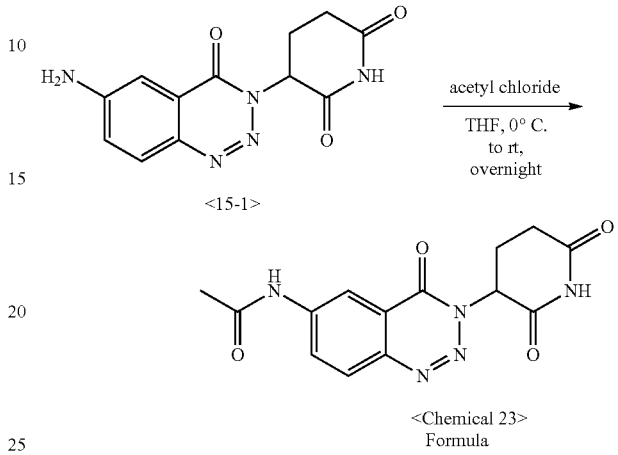

<Chemical 23> Formula

To the solution of 3-(6-amino-4-oxobenzo[d][1,2,3]triazin-3(4H)-yl)piperidine-2,6-dione (0.02 g, 0.07 mmol) dissolved in THF (5 ml), acetyl chloride (0.005 ml, 0.07 mmol) was added, and it was stirred at a room temperature overnight. The reaction mixture was extracted with ethyl acetate. The organic layer was dried on Na$_2$SO$_4$, and was purified by column chromatography to obtain a pure compound of 0.01 g (45%) as a white solid.

$^1$H NMR (300 MHz, DMSO-d$_6$) δ 11.18 (s, 1H), 10.71 (s, 1H), 8.61 (d, J=2.2 Hz, 1H), 8.23-8.13 (m, 2H), 5.98-5.93 (m, 1H), 3.02-2.90 (m, 1H), 2.70-2.63 (m, 2H), 2.30-2.23 (m, 1H), 2.15 (s, 3H);

MS found (M+H)$^+$ (m/z), 315.9; calcd for C$_{14}$H$_{13}$N$_5$O$_4$ m/z, 315.10.

Example 16

Synthesis of 3-(8-amino-1-oxoisoquinolin-2(1H)-yl)piperidine-2,6-dione (Chemical Formula 31)

[16-1] Synthesis of Compound <16-1>

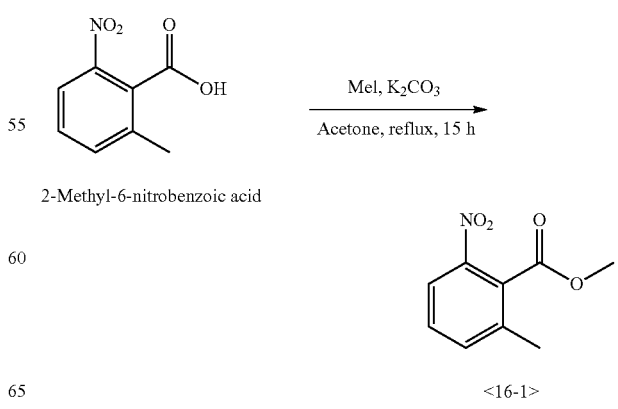

To the solution of 2-methyl-6-nitrobenzoic acid (15 g, 82.8 mmol) dissolved in acetone (350 ml), iodomethane (25.8 ml, 414.0 mmol) and potassium carbonate (57.2 g, 414.0 mmol) were added, and the reaction mixture was refluxed for 15 hours and was stirred. The reaction mixture was cooled to a room temperature and was filtered. The filtrates were concentrated, and the residues were diluted, and then were extracted with EtOAc (250 ml×2 times). The combined organic layer was dried on MgSO$_4$, and the solvent was removed under vacuum to obtain yellow oil. The combined organic layer was concentrated under reduced pressure to obtain methyl 2-methyl-6-nitro benzoate (compound <16-1>) (15.9 g, 81.5 mmol, 98%) as a white solid.

[16-2] Synthesis of Compound <16-2>

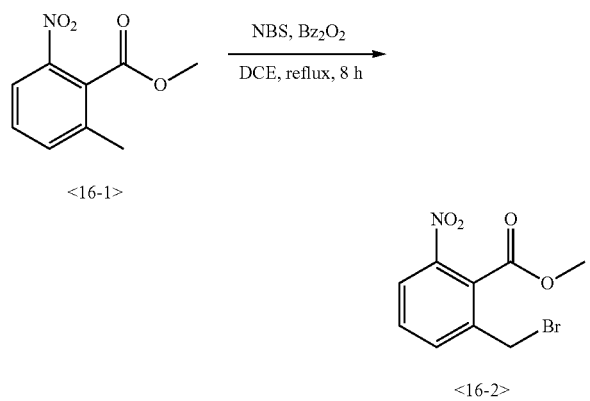

To the solution of compound <16-1> (15.9 g, 81.5 mmol) dissolved in dichloroethane (150 ml), N-bromosuccinimide (16.9 g, 122.2 mmol) and benzoyl peroxide (197 mg, 0.815 mmol) were added at a room temperature, and the mixture was stirred under reflux for 8 hours. The reaction mixture was cooled to a room temperature and was filtered. The filtrates were concentrated. The residues were purified by silica-gel column chromatography using EA/Hx (8%) as an eluent, to obtain compound <16-2> (15.9 g, 58.0 mmol, 71%) as a lemon yellow.

$^1$H NMR (400 MHz, CDCl$_3$) δ 3.98 (s, 3H), 4.57 (s, 2H), 7.59 (dd, 1H, J=7.8, 8.4 Hz), 7.78 (d, 1H, J=7.8 Hz), 8.1 (d, 1H, J=8.4 Hz).

[16-3] Synthesis of Compound <16-3>

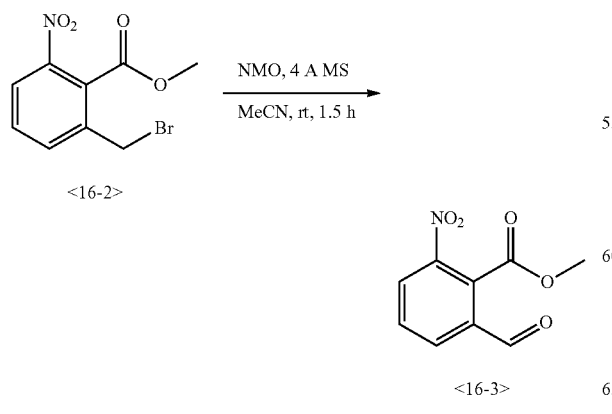

To a stirred suspension of a fire-dried 4 Å molecular sieve dissolved in acetonitrile (150 ml), NMO (15.6 g, 133.4 mmol) was added. In 5 minutes, LDH-17-081 (15.9 g, 58.0 mmol) dissolved in acetonitrile (20 ml) was added. The reaction mixture was stirred at a room temperature for 1.5 hours, and it was filtered through silica-gel, and it was eluted with EtOAc, and it was concentrated under vacuum to obtain reddish brown oil. It was purified by silica-gel column chromatography (MPLC, 0 to 30% EA/Hx) to obtain compound <16-3> (8.12 g, 38.8 mmol, 67%) as a white solid.

$^1$H NMR (300 MHz, CDCl$_3$) δ 10.08 (s, 1H), 8.44 (dd, J=8.2, 1.2 Hz, 1H), 8.26 (dd, J=7.7, 1.2 Hz, 1H), 7.81 (t, J=8.0 Hz, 1H), 4.06 (s, 3H).

[16-4] Synthesis of Compound <16-4>

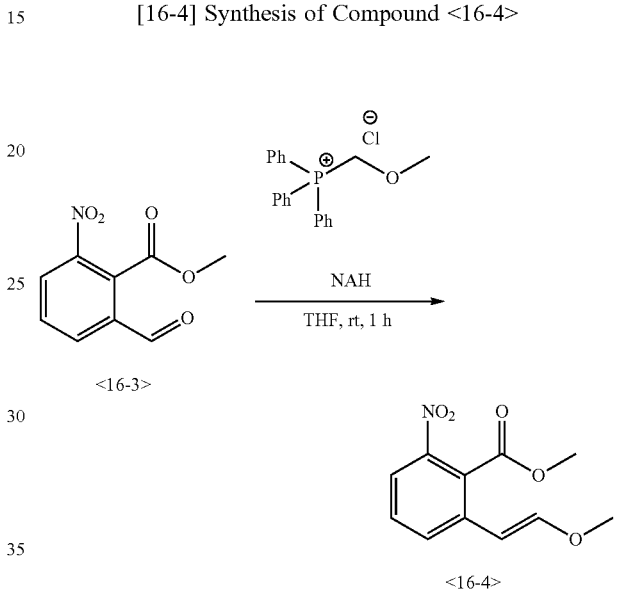

To the stirred suspension of (methoxymethyl)triphenyl phosphonium chloride (1.22 g, 3.59 mmol) dissolved in THF (24 ml), sodium hydride (192 mg, 4.78 mmol) was added in small portions in an ice container under N$_2$. The red solution was stirred at a room temperature for 30 minutes, and then compound <16-3> (500 mg, 2.39 mmol) dissolved in THF (6 ml) was added dropwise. The reactants were stirred at a room temperature for 12 hours. The mixture was diluted with water, and was extracted with EtOAc (50 ml). The combined organic layer was washed with salt water, and was dried on MgSO$_4$, and the solvent was removed under vacuum to obtain dark oil. The crude compound was purified by silica-gel column chromatography using EtOAc/Hex (30%) as an eluent, to obtain compound <16-4> (372 mg, 1.57 mmol, 66%) as yellow oil (mixture of 1.7:1 E/Z isomers).

[16-5] Synthesis of Compound <16-5>

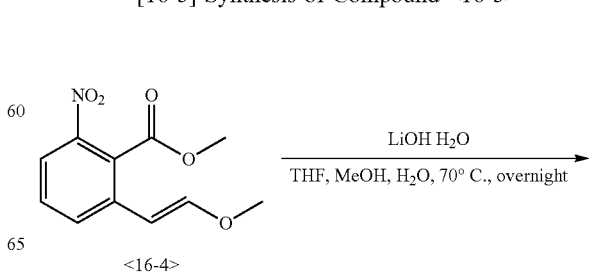

-continued

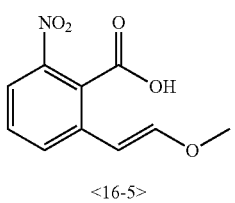

To the solution of compound <16-4> (360 mg, 1.52 mmol) dissolved in MeOH (4 ml), H₂O (4 ml) and THF (12 ml), lithium monohydrate (638 mg, 15.2 mmol) was added at a room temperature, and the reaction mixture was stirred at 70° C. overnight. The reaction mixture was concentrated to remove THF and methanol. Subsequently, water (40 ml) was added. The combined organic layer was concentrated under reduced pressure to obtain compound <16-5> (332 mg, 1.49 mmol, 98%) as a yellow solid (mixture of 1.7:1 E/Z isomers).

[16-6] Synthesis of Compound <16-7>

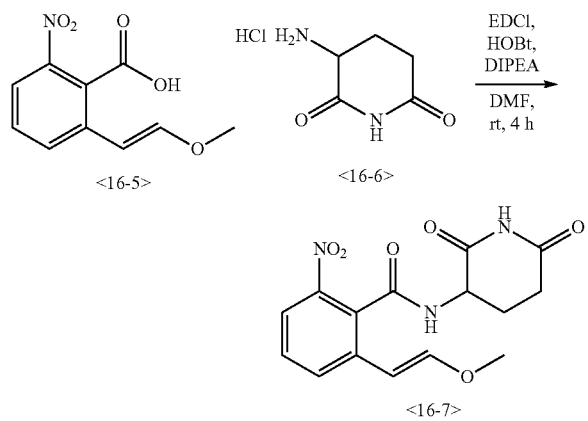

To the solution of compound <16-5> (332 mg, 1.49 mmol), 3-aminopiperidine-2,6-dione hydrochloride (1.08 g, 6.55 mmol), EDCl HCl (314 mg, 1.64 mmol), and HOBt H₂O (221 mg, 1.64 mmol), dissolved in DMF (10 ml), DIPEA (1.71 ml, 9.82 mmol) was added at a room temperature, and the reaction mixture was stirred at a room temperature for 4 hours. The reaction mixture was diluted with water and was extracted with EtOAc (50 ml×2 times). The combined organic layer was dried on MgSO₄, and the solvent was removed under vacuum to obtain yellow oil. The crude compound was purified by column chromatography using MeOH/DCM (5%) as an eluent, to obtain E-products (219 mg, 0.658 mmol, 44%), and Z-products (43 mg, 0.129 mmol, 9%) as lemon yellow solids.

¹H NMR (300 MHz, CDCl₃) δ 7.98-7.86 (m, 2H), 7.69 (d, J=7.9 Hz, 1H), 7.47 (t, J=8.1 Hz, 1H), 7.12 (d, J=12.8 Hz, 1H), 6.47 (d, J=6.5 Hz, 1H), 6.06 (d, J=12.8 Hz, 1H), 4.87-4.76 (m, 1H), 3.73 (s, 3H), 2.97-2.71 (m, 3H), 2.16-1.97 (m, 1H).

[16-7] Synthesis of Compound <16-8>

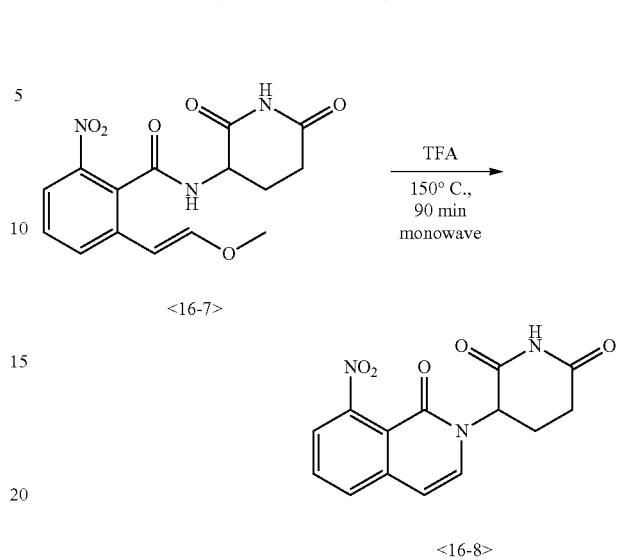

To the solution of compound <16-7> (100 mg, 0.300 mmol) dissolved in TFA (6 ml), the reaction mixture was stirred at 150° C. for 90 minutes under the monowave-assisted condition. Until the reactants were dried, it was evaporated. The residues were purified by silica-gel column chromatography using MeOH/DCM (5%) as an eluent to obtain compound <16-8> as an ivory solid.

¹H NMR (300 MHz, CDCl₃) δ 7.98 (s, 1H), 7.82-7.67 (m, 2H), 7.47 (d, J=7.3 Hz, 1H), 7.06 (d, J=7.5 Hz, 1H), 6.67 (d, J=7.4 Hz, 1H), 5.61-5.48 (m, 1H), 2.98-2.69 (m, 3H), 2.37-2.23 (m, 1H).

[16-8] Synthesis of Compound of Chemical Formula 31

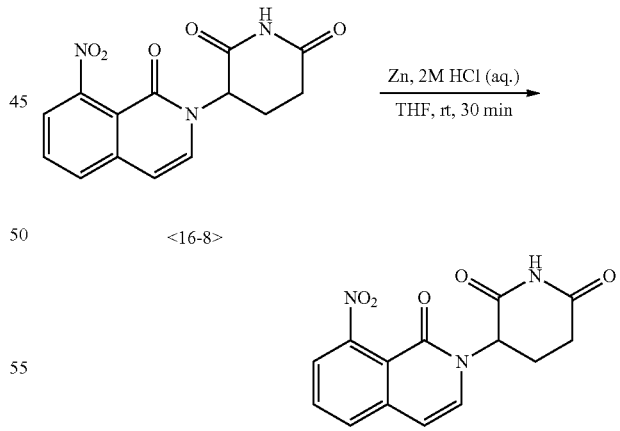

To the solution of compound <16-8> (20 mg, 0.066 mmol) and Zn (63 mg, 0.957 mmol), dissolved in THF (0.5 ml), 2M aq. HCl (0.5 ml) was added, and the reaction mixture was stirred at a room temperature for 30 minutes. The mixture was filtered, and was distributed between ethyl acetate and saturated aqueous NaHCO₃. The combined organic layer was dried on MgSO₄, and the solvent was removed under vacuum to obtain compound of Chemical formula 31 (17 mg, 0.063 mmol, 94%) as a yellow solid.

¹H NMR (300 MHz, DMSO-d₆) δ 10.99 (s, 1H), 7.29 (t, J=7.8 Hz, 2H), 7.19 (d, J=7.4 Hz, 2H), 6.65-6.54 (m, 2H), 6.40 (d, J=7.5 Hz, 1H), 5.33 (s, 1H), 2.91-2.70 (m, 1H), 2.70-2.53 (m, 2H), 2.07-1.93 (m, 1H).

Example 17

Synthesis of 3-(5-amino-1-oxoisoquinolin-2(1H)-yl)piperidine-2,6-dione (Chemical Formula 24)

[17-1] Synthesis of 5-nitro-1H-isochromen-1-one

The starting material (1 g, 5.1 mmol) was dissolved in DMF (8.2 ml) and DMFDMA (2.3 ml), and it was stirred at 115° C. for 17 hours. When the reaction was finished, it was concentrated to remove the solvent, and it was dissolved in EA, and then silica gel (80 g) was added, and it was stirred at a room temperature for 3 hours. The reactants were filtered, and were washed with EA, and then were concentrated, to obtain a desired compound, 5-nitro-1H-isochromen-1-one (800 mg, brown solid, 82%).

¹H NMR (300 MHz, CDCl₃) δ 8.62 (d, J=7.8 Hz, 1H), 8.47 (d, J=8.1 Hz, 1H), 7.65 (m, 1H), 7.42 (d, J=6.3 Hz, 1H), 7.36 (d, J=6.3 Hz, 1H).

[17-2] Synthesis of 3-(5-nitro-1-oxoisoquinolin-2(1H)-yl)piperidine-2,6-dione 5-nitro-1H-isochromen-1-one (1 g, 5.2 mmol) and 3-aminopiperidine-2,6-dione (0.67 g, 5.2 mmol) were dissolved in MeOH (10 ml), and then it was refluxed as heated for 5 hours, and then TEA (1.45 ml) was added, and the reaction was progressed overnight. When the reaction was completed, water was added to dilute it, and then it was extracted with EA and was concentrated under reduced pressure. The concentrates were dissolved in toluene, and then PPTS (0.1 g) was added and then was refluxed as heated. When the reaction was completed, it was neutralized with saturated NaHCO₃ aqueous solution, and it was extracted with EA and was dried and was isolated and purified to obtain a desired compound, 3-(5-nitro-1-oxoisoquinolin-2(1H)-yl)piperidine-2,6-dione.

¹H NMR (300 MHz, CDCl₃) δ 8.78 (d, J=8.3 Hz, 1H), 8.48 (d, J=6.6 Hz, 1H), 8.03 (s, 1H), 7.65 (t, J=8.0 Hz, 1H), 7.44 (d, J=7.8 Hz, 1H), 7.17 (d, J=7.9 Hz, 1H), 5.45-5.37 (m, 1H), 3.04-2.57 (m, 3H), 2.48-2.17 (m, 1H).

[17-3] Synthesis of 3-(5-amino-1-oxoisoquinolin-2(1H)-yl)piperidine-2,6-dione 3-(5-Nitro-1-oxoisoquinolin-2(1H)-yl)piperidine-2,6-dione was dissolved in EA, and then ammonium formate and 10% Pd/C were added, and it was refluxed as heated. When the reaction was completed, it was filtered into Celite, and it was washed with EA, and then the filtrates were concentrated under reduced pressure to obtain a desired compound, 3-(5-amino-1-oxoisoquinolin-2(1H)-yl)piperidine-2,6-dione.

¹H NMR (300 MHz, CDCl₃) δ 9.68 (s, 1H), 7.90 (d, J=8.0 Hz, 1H), 7.40-7.27 (m, 1H), 7.19-6.87 (m, 2H), 6.53 (dd, J=17.0, 7.4 Hz, 1H), 5.42 (dd, J=42.5, 18.5 Hz, 1H), 4.27-3.86 (m, 2H), 3.07-2.14 (m, 4H);

LC/MS (m/z) 272.1 (M+H).

Example 18

Synthesis of 3-(7-(aminomethyl)-4-oxobenzo[d][1,2,3]triazin-3(4H)-yl)piperidine-2,6-dione (Chemical Formula 32) and 1-(3-chloro-4-methylphenyl)-3-((3-(2,6-dioxopiperidin-3-yl)-4-oxo-3,4-dihydrobenzo[d][1,2,3]triazin-7-yl)methyl)urea (Chemical Formula 37)

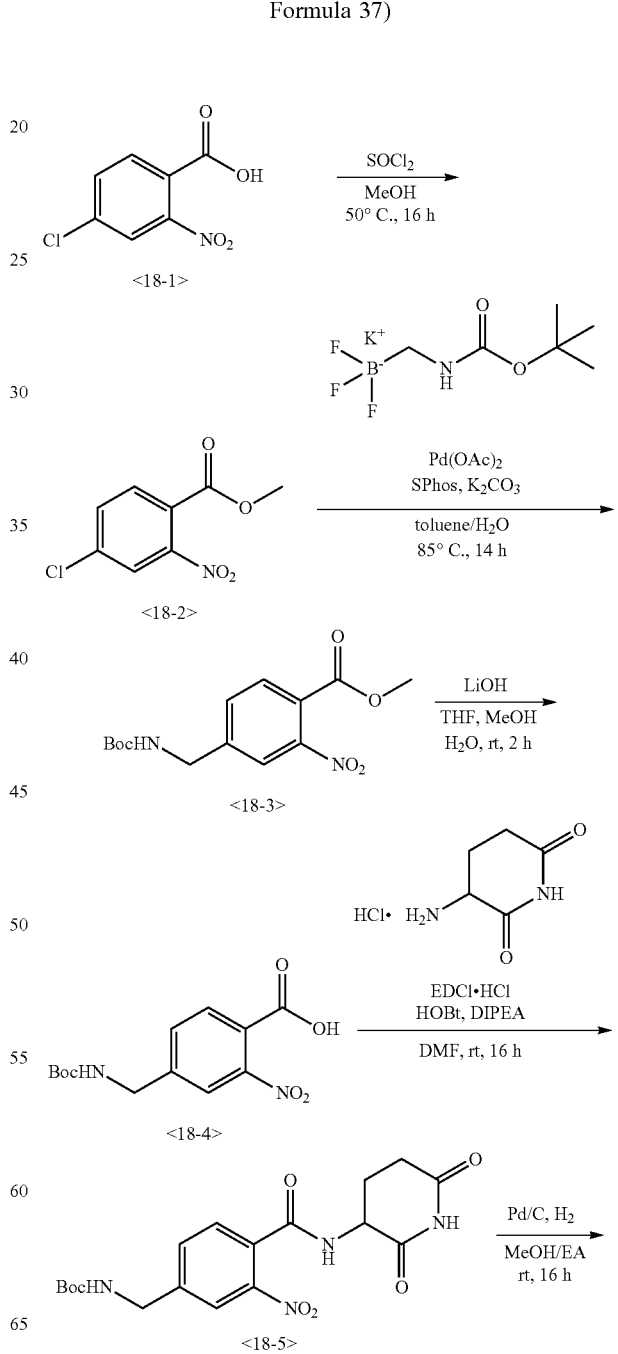

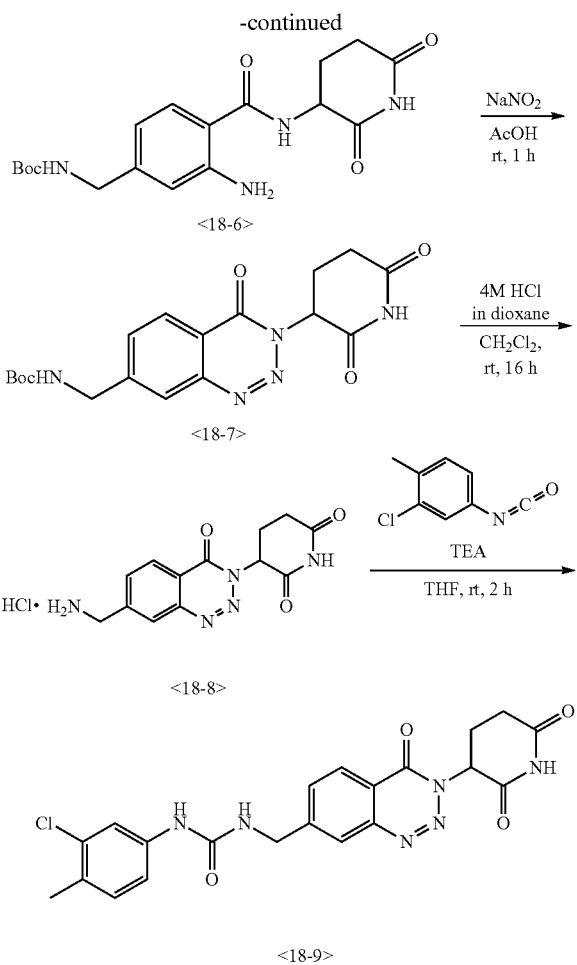

[18-1] Synthesis of methyl 4-chloro-2-nitrobenzoate 4-chloro-2-nitrobenzoic acid (10 g, 50 mmol) was suspended in dry methanol (5 ml per 1 mmol), and it was cooled to 0° C. SOCl$_2$ (22 ml, 250 mmol) was slowly added, and then the suspension was heated at 50° C. for 16 hours. The produced solution was concentrated under reduced pressure, and the residues were dissolved in water-saturated NaHCO$_3$ solution (2.5 ml/1 mmol). The solution was extracted with ethyl acetate (2.5 ml×3 times/1 mmol). The combined organic layer was washed with saturated aqueous NaCl solution (7.5 ml per 1 mmol), and it was dried with Na$_2$SO$_4$ to filter it, and then the solution was concentrated under reduced pressure to obtain a pure compound of 9 g (70%) as an ivory solid.

$^1$H NMR (300 MHz, CDCl$_3$) δ 7.86 (d, J=1.8 Hz, 1H), 7.73 (d, J=8.3 Hz, 1H), 7.64 (dd, J=8.3, 1.9 Hz, 1H), 3.92 (s, 3H).

[18-2] Synthesis of methyl 4-(((tert-butoxy carbonyl)amino)methyl)-2-nitrobenzoate Potassium [[(tert-butoxy carbonyl)amino]methyl]trifluoroborate (2.6 g, 11 mmol), methyl 4-chloro-2-nitro benzoate (2 g, 9.28 mmol), Pd(OAc)2 (0.104 g, 0.464 mmol), SPhos ligand (0.38 g, 0.928 mmol) and K$_2$CO$_3$ (4 g, 28 mmol) were filled into a sealed tube. The mixture was washed with N$_2$ 3 times. subsequently, toluene/H$_2$O (4:1, 20 ml/5 ml) was added to the reaction tube and it was deaerated with N$_2$ for 30 minutes. The reaction mixture was stirred at 85° C. for 4 hours, and then it was cooled to a room temperature. The produced mixture was extracted with EtOAc, and then the organic layer was combined, and it was dried (MgSO$_4$) and was filtered. The solvent was removed under vacuum and the products were purified by column chromatography to obtain a pure compound of 2.5 g (87%) as an ivory solid.

$^1$H NMR (300 MHz, CDCl$_3$) δ 7.79 (s, 1H), 7.72 (d, J=7.9 Hz, 1H), 7.58 (d, J=7.9 Hz, 1H), 5.04 (s, 1H), 4.41 (d, J=5.9 Hz, 2H), 3.91 (s, 3H), 1.46 (s, 9H).

[18-3] Synthesis of 4-(((tert-butoxy carbonyl)amino)methyl)-2-nitrobenzoic acid

To the solution of 4-((tert-butoxy carbonyl)amino)methyl)-2-nitro benzoate (1.5 g, 4.8 mmol) dissolved in THF/MeOH (10 ml/10 ml), LiOH (0.480 g, 20 mmol) dissolved in H$_2$O (2.5 ml) was added, and it was stirred at a room temperature for 2 hours. After the reaction was completed, the solvent was evaporated and it was extracted with H$_2$O. HCl was added to the water layer, and it was extracted with EA. The organic layer was dried on Na$_2$SO$_4$ to obtain a pure compound of 1.4 g (98%) as a brown solid.

$^1$H NMR (500 MHz, DMSO-d$_6$) δ 13.81 (s, 1H), 7.82 (d, J=7.9 Hz, 1H), 7.78 (s, 1H), 7.62 (d, J=8.5 Hz, 1H), 7.58 (t, J=6.2 Hz, 1H), 4.24 (d, J=6.1 Hz, 2H), 1.39 (s, 9H).

[18-4] Synthesis of tert-butyl (4-((2,6-dioxopiperidin-3-yl)carbamoyl)-3-nitrobenzyl)carbamate To 4-((tert-butoxy carbonyl)amino)methyl)-2-nitrobenzoic acid (1.4 g, 3.85 mmol), EDCl-HCl (0.813 mg, 4.24 mmol) and HOBt (0.649 mg, 4.24 mmol) were added, and it was stirred at a room temperature for 30 minutes. To the reaction mixture, 3-aminopiperidine-2,6-dione hydrochloride (1.3 g, 7.7 mmol) and DIPEA (2.7 ml, 15.4 mmol) were added, and it was stirred at a room temperature for 16 hours. After the reaction was finished, the mixture was extracted with EA. The organic layer was dried on Na$_2$SO$_4$, and was purified by column chromatography to obtain a pure compound 1.05 g (67%) as a white-green solid.

$^1$H NMR (500 MHz, DMSO-d$_6$) δ 10.88 (s, 1H), 9.01 (d, J=8.3 Hz, 1H), 7.89 (s, 1H), 7.67 (d, J=8.0 Hz, 1H), 7.61-7.58 (m, 2H), 4.75-4.70 (m, 1H), 4.24 (d, J=6.1 Hz, 2H), 2.82-2.75 (m, 1H), 2.57-2.49 (m, 1H), 2.06-1.99 (m, 2H).

[18-5] Synthesis of tert-butyl (3-amino-4-((2,6-dioxopiperidin-3-yl)carbamoyl)benzyl)carbamate To tert-butyl(4-((2,6-dioxopiperidin-3-yl)carbamoyl)-3-nitrobenzyl)carbamate (1 g, 2.5 mmol) dissolved in MeOH/EA (50 ml/50 ml), 1 Pd/C (0.1 g) was added, and the reaction mixture was stirred under the hydrogen gas circumstance at a room temperature for 16 hours. The solution was filtered through Celite, and it was dried under vacuum to obtain a pure compound of 932 mg (99%) as a grey-white solid.

$^1$H NMR (300 MHz, DMSO-d$_6$) δ 10.83 (s, 1H), 8.40 (d, J=8.3 Hz, 1H), 7.46 (d, J=8.2 Hz, 1H), 7.32 (t, J=6.3 Hz, 1H), 6.55 (d, J=1.6 Hz, 1H), 6.49 (s, 2H), 6.40 (d, J=8.1 Hz, 1H), 4.76-4.67 (m, 1H), 4.00 (d, J=6.3 Hz, 2H), 2.84-2.72 (m, 1H), 2.56-2.54 (m, 1H), 2.16-2.03 (m, 1H), 1.99-1.90 (m, 1H).

[18-6] Synthesis of tert-butyl ((3-(2,6-dioxopiperidin-3-yl)-4-oxo-3,4-dihydrobenzo[d][1,2,3]triazin-7-yl)methyl)carbamate To the solution of tert-butyl(3-amino-4-((2,6-deoxypiperidin-3-yl)carbamoyl)benzyl)carbamate (0.922 g, 2.45 mmol) dissolved in glacial acetic acid (10 ml), sodium nitrite (0.288 g, 4.17 mmol) was added, and it was stirred at a room temperature for 1 hour. The reaction mixture was extracted with EA. The organic layer was dried on $Na_2SO_4$, and was purified by column chromatography to obtain a pure compound of 0.613 g (65%) as a white solid.

$^1$H NMR (300 MHz, Chloroform-d) δ 8.32 (d, J=8.2 Hz, 1H), 8.09 (s, 1H), 8.02 (s, 1H), 7.77 (d, J=8.2 Hz, 1H), 5.86-5.80 (m, 1H), 5.11 (s, 1H), 4.56 (d, J=6.3 Hz, 2H), 3.04-2.83 (m, 3H), 2.44-2.37 (m, 1H), 1.48 (s, 9H).

[18-7] Synthesis of 3-(7-(aminomethyl)-4-oxobenzo[d][1,2,3]triazin-3(4H)-yl)piperidine-2,6-dione hydrochloride To the solution of tert-butyl((3-(2,6-dioxopiperidin-3-yl)-4-oxo-3,4-dihydrobenzo[d][1,2,3]triazin-7-yl)methyl)carbamate (0.605 mg, 1.56 mmol) dissolved in DCM (10 ml), 4M HCl mixed to 1,4-dioxane (2 ml) was added, and it was stirred at a room temperature for 16 hours. the solvent was dried under vacuum to obtain a compound of 0.545 g (quant.) (Chemical formula 32) as an ivory solid.

$^1$H NMR (500 MHz, DMSO-$d_6$) δ 11.22 (s, 1H), 8.65 (s, 3H), 8.40 (d, J=1.5 Hz, 1H), 8.33 (d, J=8.1 Hz, 1H), 8.06 (dd, J=8.2, 1.6 Hz, 1H), 6.02-5.99 (m, 1H), 4.35 (q, J=5.7 Hz, 2H), 3.02-2.94 (m, 1H), 2.75-2.66 (m, 2H), 2.32-2.27 (m, 1H).

[18-8] Synthesis of 1-(3-chloro-4-methylphenyl)-3-((3-(2,6-dioxopiperidin-3-yl)-4-oxo-3,4-dihydrobenzo[d][1,2,3]triazin-7-yl)methyl)urea (Chemical Formula 37)

The mixture of 3-(7-(aminomethyl)-4-oxobenzo[d][1,2,3]triazin-3(4H)-yl)piperidine-2,6-dione hydrochloride (0.2 g, 0.62 mmol), 3-chloro-4-methylphenyl isocyanate (0.104 g, 0.62 mmol) and TEA (0.2 ml, 1.24 mmol), dissolved in THF (10 ml) was heated from a room temperature to 40° C. for 2 hours. The mixture was extracted with EA and was purified by column chromatography to obtain the pure compound of Chemical formula 37 of 0.134 g (48%) as an ivory solid.

$^1$H NMR (500 MHz, DMSO-$d_6$) δ 11.19 (s, 1H), 8.92 (s, 1H), 8.25 (d, J=8.2 Hz, 1H), 8.11 (s, 1H), 7.90 (d, J=8.1 Hz, 1H), 7.66 (d, J=2.0 Hz, 1H), 7.20-7.14 (m, 2H), 7.00 (t, J=6.1 Hz, 1H), 6.00-5.96 (m, 1H), 4.56 (d, J=6.0 Hz, 2H), 3.00-2.93 (m, 1H), 2.73-2.66 (m, 2H), 2.30-2.25 (m, 1H), 2.23 (s, 3H).

Example 19

Synthesis of 1-(3-chloro-4-methylphenyl)-3-((3-(2,6-dioxopiperidin-3-yl)-4-oxo-3,4-dihydrobenzo[d][1,2,3]triazin-5-yl)methyl)urea (Chemical Formula 39)

The compound of Chemical formula 39 was prepared according to the preparation method of Example 18.

$^1$H NMR (300 MHz, DMSO-$d_6$) δ 11.21 (s, 1H), 8.97 (s, 1H), 8.17-8.07 (m, 2H), 7.88 (d, J=7.1 Hz, 1H), 7.64 (d, J=2.1 Hz, 1H), 7.17 (d, J=8.3 Hz, 1H), 7.09 (dd, J=8.2, 2.2 Hz, 1H), 6.81 (t, J=6.3 Hz, 1H), 6.03-5.98 (m, 1H), 4.84 (d, J=6.1 Hz, 2H), 3.04-2.93 (m, 1H), 2.79-2.65 (m, 2H), 2.34-2.25 (m, 1H), 2.22 (s, 3H).

Example 20

Synthesis of 1-(3-chlorophenyl)-3-((3-(2,6-dioxopiperidin-3-yl)-4-oxo-3,4-dihydrobenzo[d][1,2,3]triazin-7-yl)methyl)urea (Chemical Formula 40)

The compound of Chemical formula 40 was prepared according to the preparation method of Example 18.

$^1$H NMR (300 MHz, DMSO-$d_6$) δ 11.17 (s, 1H), 9.01 (s, 1H), 8.26 (d, J=8.2 Hz, 1H), 8.11 (s, 1H), 7.91 (dd, J=8.2, 1.6 Hz, 1H), 7.68 (s, 1H), 7.25-7.23 (m, 2H), 7.02 (t, J=6.1 Hz, 1H), 6.98-6.93 (m, 1H), 6.01-5.95 (m, 1H), 4.57 (d, J=6.0 Hz, 2H), 3.03-2.92 (m, 1H), 2.77-2.64 (m, 2H), 2.31-2.24 (m, 1H).

Example 21

Synthesis of 1-(4-chlorophenyl)-3-((3-(2,6-dioxopiperidin-3-yl)-4-oxo-3,4-dihydrobenzo[d][1,2,3]triazin-7-yl)methyl)urea (Chemical Formula 41)

The compound of Chemical formula 41 was prepared according to the preparation method of Example 18.

$^1$H NMR (300 MHz, DMSO-$d_6$) δ 11.18 (s, 1H), 8.93 (s, 1H), 8.25 (d, J=8.2 Hz, 1H), 8.11 (s, 1H), 7.90 (dd, J=8.2, 1.6 Hz, 1H), 7.48-7.43 (m, 2H), 7.29-7.24 (m, 2H), 6.97 (t, J=6.0 Hz, 1H), 6.01-5.95 (m, 1H), 4.57 (d, J=5.9 Hz, 2H), 3.03-2.92 (m, 1H), 2.77-2.63 (m, 2H), 2.31-2.24 (m, 1H).

Example 22

Synthesis of 1-(3,4-dichlorophenyl)-3-((3-(2,6-dioxopiperidin-3-yl)-4-oxo-3,4-dihydrobenzo[d][1,2,3]triazin-7-yl)methyl)urea (Chemical Formula 42)

The compound of Chemical formula 42 was prepared according to the preparation method of Example 18.

$^1$H NMR (300 MHz, DMSO-$d_6$) δ 11.18 (s, 1H), 9.13 (s, 1H), 8.26 (d, J=8.2 Hz, 1H), 8.11 (s, 1H), 7.90 (dd, J=8.2, 1.6 Hz, 1H), 7.85 (d, J=2.5 Hz, 1H), 7.46 (d, J=8.8 Hz, 1H), 7.30 (dd, J=8.9, 2.5 Hz, 1H), 7.09 (t, J=6.1 Hz, 1H), 6.01-5.95 (m, 1H), 4.57 (d, J=6.0 Hz, 2H), 3.03-2.91 (m, 1H), 2.77-2.64 (m, 2H), 2.31-2.23 (m, 1H).

Example 23

Synthesis of 1-(4-chloro-3-(trifluoromethyl)phenyl)-3-((3-(2,6-dioxopiperidin-3-yl)-4-oxo-3,4-dihydrobenzo[d][1,2,3]triazin-7-yl)methyl)urea (Chemical Formula 43)

The compound of Chemical formula 43 was prepared according to the preparation method of Example 18.

$^1$H NMR (300 MHz, DMSO-$d_6$) δ 11.17 (s, 1H), 9.34 (s, 1H), 8.26 (d, J=8.2 Hz, 1H), 8.12 (s, 1H), 8.07 (d, J=2.5 Hz, 1H), 7.91 (dd, J=8.2, 1.6 Hz, 1H), 7.63 (dd, J=8.8, 2.5 Hz, 1H), 7.55 (d, J=8.7 Hz, 1H), 7.17 (t, J=6.2 Hz, 1H), 6.01-5.95 (m, 1H), 4.58 (d, J=5.9 Hz, 2H), 3.03-2.90 (m, 1H), 2.76-2.63 (m, 2H), 2.31-2.23 (m, 1H).

Example 24

Synthesis of 1-(3-chloro-4-methoxyphenyl)-3-((3-(2,6-dioxopiperidin-3-yl)-4-oxo-3,4-dihydrobenzo[d][1,2,3]triazin-7-yl)methyl)urea (Chemical Formula 44)

The compound of Chemical formula 44 was prepared according to the preparation method of Example 18.
$^1$H NMR (300 MHz, DMSO-d$_6$) δ 11.17 (s, 1H), 8.78 (s, 1H), 8.25 (d, J=8.2 Hz, 1H), 8.11 (s, 1H), 7.90 (dd, J=8.1, 1.6 Hz, 1H), 7.63 (d, J=2.6 Hz, 1H), 7.23 (dd, J=8.9, 2.6 Hz, 1H), 7.03 (d, J=9.0 Hz, 1H), 6.95 (t, J=6.0 Hz, 1H), 6.01-5.95 (m, 1H), 4.56 (d, J=6.0 Hz, 2H), 3.03-2.91 (m, 1H), 2.77-2.63 (m, 2H), 2.32-2.24 (m, 1H).

Example 25

Synthesis of Other Compounds

[25-1] Synthesis of 3-chloro-N-((3-(2,6-dioxopiperidin-3-yl)-4-oxo-3,4-dihydrobenzo[d][1,2,3]triazin-6-yl)methyl)-4-methylbenzamide (Chemical Formula The compound of Chemical formula 46 was prepared according to the preparation method of Example 18.
$^1$H NMR (300 MHz, DMSO-d$_6$) δ 11.20 (s, 1H), 9.35 (t, J=5.9 Hz, 1H), 8.26 (d, J=8.1 Hz, 1H), 8.14 (s, 1H), 7.98 (d, J=1.7 Hz, 1H), 7.93 (d, J=8.2 Hz, 1H), 7.81 (dd, J=8.0, 1.8 Hz, 1H), 7.50 (d, J=7.9 Hz, 1H), 5.99 (dd, J=12.3, 5.4 Hz, 1H), 4.74 (d, J=5.5 Hz, 2H), 3.07-2.88 (m, 1H), 2.75-2.63 (m, 2H), 2.40 (s, 3H), 2.35-2.22 (m, 1H).

[25-2] Synthesis of 3-(6-(aminomethyl)-4-oxobenzo[d][1,2,3]triazin-3(4H)-yl)piperidine-2,6-dione (Chemical Formula 33)

The compound of Chemical formula 33 was prepared according to the preparation method of Example 14.
$^1$H NMR (500 MHz, DMSO-d$_6$) δ 11.22 (s, 1H), 8.57 (s, 3H), 8.44 (d, J=1.9 Hz, 1H), 8.33 (d, J=8.4 Hz, 1H), 8.22 (dd, J=8.5, 1.9 Hz, 1H), 6.05-6.00 (m, 1H), 4.32 (q, J=5.9 Hz, 2H), 3.02-2.94 (m, 1H), 2.76-2.67 (m, 2H), 2.32-2.28 (m, 1H).

[25-3] Synthesis of 3-(5-(aminomethyl)-4-oxobenzo[d][1,2,3]triazin-3(4H)-yl)piperidine-2,6-dione (Chemical Formula 34)

The compound of Chemical formula 34 was prepared according to the preparation method of Example 14.
$^1$H NMR (500 MHz, DMSO-d$_6$) δ 11.24 (s, 1H), 8.36 (s, 3H), 8.32 (d, J=8.1 Hz, 1H), 8.19 (t, J=7.8 Hz, 1H), 7.99 (d, J=7.5 Hz, 1H), 6.04-6.01 (m, 1H), 4.66-4.55 (m, 2H), 3.01-2.93 (m, 1H), 2.73-2.63 (m, 2H), 2.29-2.23 (m, 1H).

[25-4] Synthesis of 1-(3-chlorophenyl)-3-((3-(2,6-dioxopiperidin-3-yl)-4-oxo-3,4-dihydrobenzo[d][1,2,3]triazin-7-yl)methyl)thiourea (Chemical Formula 52)

The compound of Chemical formula 52 was prepared according to the preparation method of Example 18.
$^1$H NMR (500 MHz, DMSO-d$_6$) δ 11.20 (s, 1H), 10.00 (s, 1H), 8.60 (s, 1H), 8.26 (d, J=8.2 Hz, 1H), 8.12 (s, 1H), 7.92 (dd, J=8.2, 1.6 Hz, 1H), 7.68 (s, 1H), 7.36 (d, J=5.1 Hz, 2H), 7.19-7.17 (m, 1H), 6.00-5.97 (m, 1H), 5.01 (d, J=5.8 Hz, 2H), 3.00-2.93 (m, 1H), 2.74-2.63 (m, 2H), 2.30-2.27 (m, 1H).

[25-5] Synthesis of 2-(3-chlorophenyl)-N-((3-(2,6-dioxopiperidin-3-yl)-4-oxo-3,4-dihydrobenzo[d][1,2,3]triazin-7-yl)methyl)acetamide (Chemical Formula 53)

The compound of Chemical formula 53 was prepared according to the preparation method of Example 18.
$^1$H NMR (500 MHz, DMSO-d$_6$) δ 11.20 (s, 1H), 8.85 (t, J=6.0 Hz, 1H), 8.22 (d, J=8.1 Hz, 1H), 8.04 (s, 1H), 7.83 (dd, J=8.3, 1.3 Hz, 1H), 7.36-7.30 (m, 3H), 7.26 (d, J=7.4 Hz, 1H), 5.99-5.96 (m, 1H), 4.55 (d, J=6.0 Hz, 2H), 3.58 (s, 2H), 3.00-2.92 (m, 1H), 2.73-2.64 (m, 2H), 2.29-2.25 (m, 1H).

[25-6] Synthesis of 3-(4-oxobenzo[d][1,2,3]triazin-3(4H)-yl)piperidine-2,6-dione (Chemical Formula 25)

The compound of Chemical formula 25 was prepared according to the preparation method of Example 14.
$^1$H NMR (300 MHz, CDCl$_3$) δ 8.40 (d, J=7.1 Hz, 1H), 8.23 (d, J=8.2 Hz, 1H), 8.09 (s, 1H), 8.03 (t, J=7.7 Hz, 1H), 7.88 (t, J=7.6 Hz, 1H), 5.89-5.83 (m, 1H), 3.08-2.83 (m, 3H), 2.52-2.31 (m, 1H).

[25-7] Synthesis of 3-(7-nitro-4-oxobenzo[d][1,2,3]triazin-3(4H)-yl)piperidine-2,6-dione (Chemical Formula 26)

The compound of Chemical formula 26 was prepared according to the preparation method of Example 14.
$^1$H NMR (300 MHz, Methanol-d$_4$) δ 9.03 (s, 1H), 8.70 (d, J=8.7 Hz, 1H), 8.58 (d, J=8.8 Hz, 1H), 6.14-5.99 (m, 1H), 3.12-2.85 (m, 3H), 2.54-2.38 (m, 1H).

[25-8] Synthesis of 3-(6-nitro-4-oxobenzo[d][1,2,3]triazin-3(4H)-yl)piperidine-2,6-dione (Chemical Formula 27)

The compound of Chemical formula 27 was prepared according to the preparation method of Example 14.
$^1$H NMR (300 MHz, Methanol-d$_4$) δ 9.11 (d, J=2.5 Hz, 1H), 8.85 (d, J=11.5 Hz, 1H), 8.46 (d, J=8.7 Hz, 1H), 6.29-5.87 (m, 1H), 3.33-2.71 (m, 3H), 2.52-2.31 (m, 1H).

[25-9] Synthesis of 3-(7-amino-4-oxobenzo[d][1,2,3]triazin-3(4H)-yl)piperidine-2,6-dione (Chemical Formula 28)

The compound of Chemical formula 28 was prepared according to the preparation method of Example 14.
$^1$H NMR (500 MHz, Methanol-d$_4$) δ 7.99 (d, J=8.3 Hz, 1H), 7.20-7.10 (m, 2H), 5.89 (dd, J=12.2, 5.4 Hz, 1H), 3.02-2.79 (m, 3H), 2.39-2.32 (m, 1H).

[25-10] Synthesis of 3-(2,6-dioxopiperidin-3-yl)-4-oxo-3,4-dihydrobenzo[d][1,2,3]triazin-5-carboxylic acid (Chemical Formula 29)

The compound of Chemical formula 29 was prepared according to the preparation method of Example 14.
$^1$H NMR (300 MHz, DMSO-d$_6$) δ 13.50 (s, 1H), 11.23 (s, 1H), 8.33 (dd, J=8.2, 1.1 Hz, 1H), 8.17 (t, J=7.8 Hz, 1H), 7.94 (dd, J=7.4, 1.1 Hz, 1H), 6.03-5.97 (m, 1H), 3.03-2.90 (m, 1H), 2.75-2.60 (m, 2H), 2.34-2.25 (m, 1H).

[25-11] Synthesis of 3-(5-amino-4-oxobenzo[d][1,2,3]triazin-3(4H)-yl)-3-methylpiperidine-2,6-dione (Chemical Formula 30)

The compound of Chemical formula 30 was prepared according to the preparation method of Example 14.

$^1$H NMR (500 MHz, DMSO-$d_6$) δ 11.03 (s, 1H), 7.68 (t, J=8.0 Hz, 1H), 7.18-7.17 (m, 3H), 6.97 (d, J=7.9 Hz, 1H), 2.96-2.88 (m, 1H), 2.73-2.67 (m, 1H), 2.63-2.58 (m, 1H), 2.01-1.97 (m, 1H), 1.95 (s, 3H).

[25-12] Synthesis of 1-(3-chloro-4-methylphenyl)-3-((3-(2,6-dioxopiperidin-3-yl)-4-oxo-3,4-dihydrobenzo[d][1,2,3]triazin-6-yl)methyl)urea (Chemical Formula 38)

The compound of Chemical formula 38 was prepared according to the preparation method of Example 18.

$^1$H NMR (300 MHz, DMSO-$d_6$) δ 11.19 (s, 1H), 8.90 (s, 1H), 8.23 (d, J=8.3 Hz, 1H), 8.17 (s, 1H), 8.05 (d, J=8.5 Hz, 1H), 7.65 (s, 1H), 7.20-7.13 (m, 2H), 6.98 (t, J=6.1 Hz, 1H), 6.01-5.95 (m, 1H), 4.52 (s, 2H), 3.03-2.90 (m, 1H), 2.76-2.63 (m, 2H), 2.32-2.23 (m, 1H), 2.23 (s, 3H).

[25-13] Synthesis of 3-(2,6-dioxopiperidin-3-yl)-4-oxo-3,4-dihydrobenzo[d][1,2,3]triazin-5-carboxamide (Chemical Formula 54)

The compound of Chemical formula 54 was prepared according to the preparation method of Example 14.

$^1$H NMR (500 MHz, Chloroform-d) δ 8.29 (d, J=8.1 Hz, 1H), 8.16 (s, 1H), 8.04 (t, J=7.8 Hz, 1H), 7.95 (d, J=7.4 Hz, 1H), 6.24 (s, 1H), 5.96 (s, 1H), 5.82-5.79 (m, 1H), 3.02-2.93 (m, 2H), 2.87-2.79 (m, 1H), 2.42-2.37 (m, 1H).

[25-14] Synthesis of 3-(2,6-dioxopiperidin-3-yl)-N-methyl-4-oxo-3,4-dihydrobenzo[d][1,2,3]triazin-5-carboxamide (Chemical Formula 55)

The compound of Chemical formula 55 was prepared according to the preparation method of Example 14.

$^1$H NMR (500 MHz, Chloroform-d) δ 8.26 (d, J=8.0 Hz, 1H), 8.13 (s, 1H), 8.01 (t, J=7.8 Hz, 1H), 7.86 (d, J=7.3 Hz, 1H), 6.11 (d, J=5.2 Hz, 1H), 5.84-5.81 (m, 1H), 3.07 (d, J=4.9 Hz, 3H), 3.00-2.91 (m, 2H), 2.84-2.77 (m, 1H), 2.39-2.34 (m, 1H).

[25-15] Synthesis of N-(3-(2,6-dioxopiperidin-3-yl)-4-oxo-3,4-dihydrobenzo[d][1,2,3]triazin-5-yl)benzamide (Chemical Formula 56)

The compound of Chemical formula 56 was prepared according to the preparation method of Example 14.

$^1$H NMR (300 MHz, DMSO-$d_6$) δ 12.49 (s, 1H), 11.26 (s, 1H), 9.12 (d, J=8.0 Hz, 1H), 8.20 (t, J=8.2 Hz, 1H), 8.02-7.99 (m, 3H), 7.73-7.61 (m, 3H), 6.17-6.11 (m, 1H), 3.02-2.94 (m, 1H), 2.77-2.67 (m, 2H), 2.37-2.30 (m, 1H).

Example 26

Synthesis of 3-chloro-N-((3-(2,6-dioxopiperidin-3-yl)-4-oxo-3,4-dihydrobenzo[d][1,2,3]triazin-6-yl)methyl)-4-methylbenzamide (Chemical Formula 45)

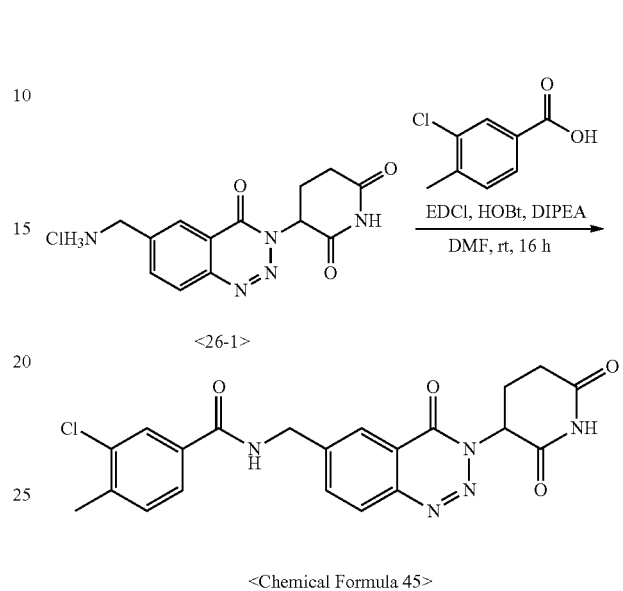

<Chemical Formula 45>

To 3-chloro-4-methylbenzoic acid (16 mg, 0.093 mmol), EDCl-HCl (20 mg, 0.102 mmol) and HOBt (16 mg, 0.102 mmol) were added, and it was stirred at a room temperature for 30 minutes. To the reaction mixture, 3-(6-(aminomethyl)-4-oxobenzo[d][1,2,3]triazin-3(4H)-yl)piperidine-2,6-dione hydrochloride (30 mg, 0.093 mmol) and DIPEA (0.03 ml, 0.186 mmol) were treated, and it was stirred at a room temperature for 16 hours. After the reaction was completed, the mixture was extracted with EA. The organic layer was dried on $Na_2SO_4$, and was purified by column chromatography to obtain a pure compound of 24 mg (60%) as a white solid.

$^1$H NMR (300 MHz, DMSO-$d_6$) δ 11.19 (s, 1H), 9.34 (t, J=5.9 Hz, 1H), 8.24 (d, J=8.3 Hz, 1H), 8.18 (s, 1H), 8.08 (d, J=8.2 Hz, 1H), 7.95 (s, 1H), 7.79 (d, J=8.0 Hz, 1H), 7.49 (d, J=8.0 Hz, 1H), 6.00-5.95 (m, 1H), 4.70 (d, J=5.9 Hz, 2H), 3.01-2.86 (m, 1H), 2.76-2.63 (m, 2H), 2.39 (s, 3H), 2.30-2.23 (m, 1H).

Example 27

Synthesis of 1-(3-chloro-4-methylphenyl)-3-((2-(2,6-dioxopiperidin-3-yl)-1-oxo-1,2-dihydroisoquinolin-7-yl)methyl)urea (Chemical Formula 47)

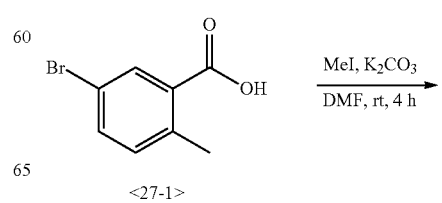

<27-1>

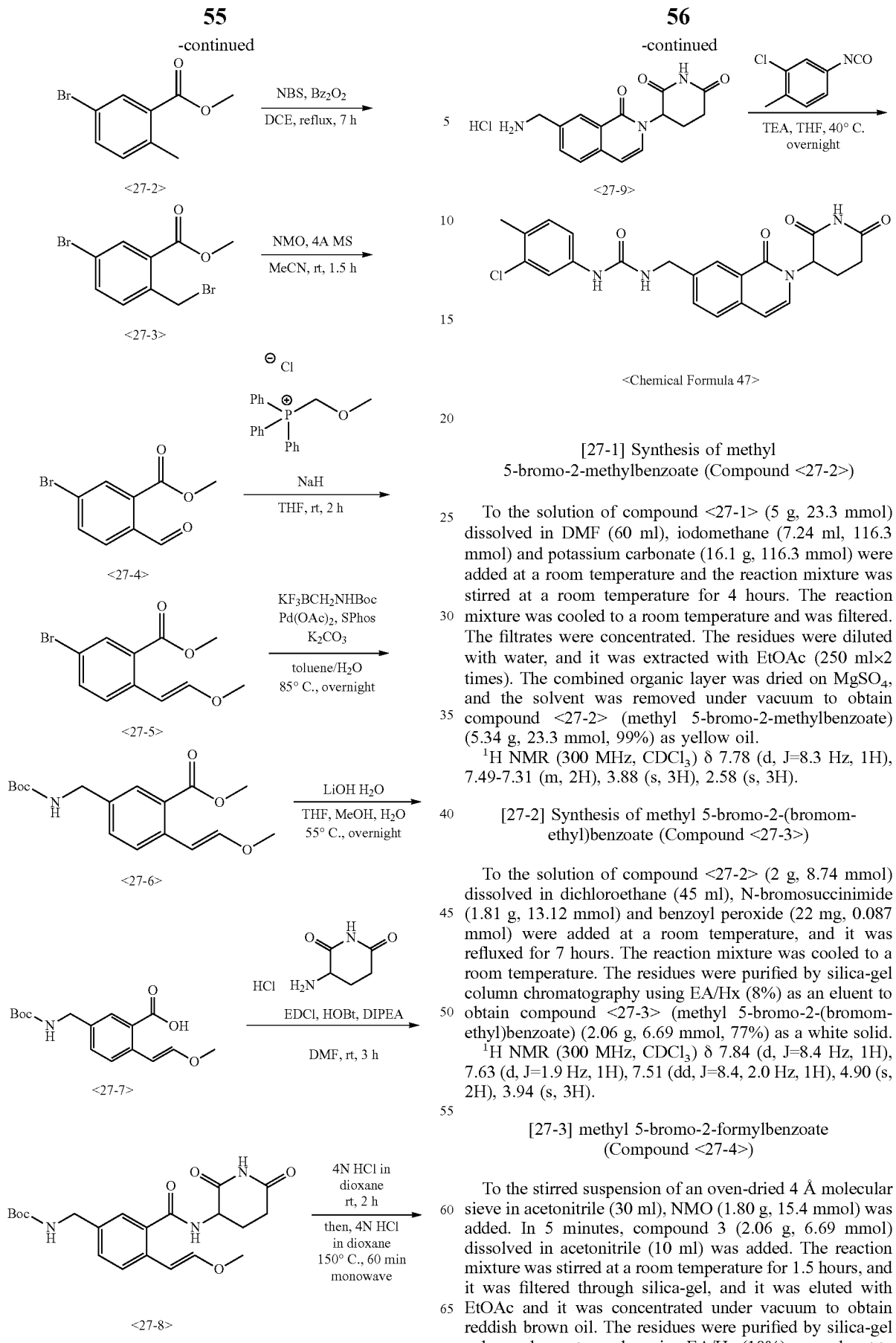

[27-1] Synthesis of methyl 5-bromo-2-methylbenzoate (Compound <27-2>)

To the solution of compound <27-1> (5 g, 23.3 mmol) dissolved in DMF (60 ml), iodomethane (7.24 ml, 116.3 mmol) and potassium carbonate (16.1 g, 116.3 mmol) were added at a room temperature and the reaction mixture was stirred at a room temperature for 4 hours. The reaction mixture was cooled to a room temperature and was filtered. The filtrates were concentrated. The residues were diluted with water, and it was extracted with EtOAc (250 ml×2 times). The combined organic layer was dried on $MgSO_4$, and the solvent was removed under vacuum to obtain compound <27-2> (methyl 5-bromo-2-methylbenzoate) (5.34 g, 23.3 mmol, 99%) as yellow oil.

$^1$H NMR (300 MHz, $CDCl_3$) δ 7.78 (d, J=8.3 Hz, 1H), 7.49-7.31 (m, 2H), 3.88 (s, 3H), 2.58 (s, 3H).

[27-2] Synthesis of methyl 5-bromo-2-(bromomethyl)benzoate (Compound <27-3>)

To the solution of compound <27-2> (2 g, 8.74 mmol) dissolved in dichloroethane (45 ml), N-bromosuccinimide (1.81 g, 13.12 mmol) and benzoyl peroxide (22 mg, 0.087 mmol) were added at a room temperature, and it was refluxed for 7 hours. The reaction mixture was cooled to a room temperature. The residues were purified by silica-gel column chromatography using EA/Hx (8%) as an eluent to obtain compound <27-3> (methyl 5-bromo-2-(bromomethyl)benzoate) (2.06 g, 6.69 mmol, 77%) as a white solid.

$^1$H NMR (300 MHz, $CDCl_3$) δ 7.84 (d, J=8.4 Hz, 1H), 7.63 (d, J=1.9 Hz, 1H), 7.51 (dd, J=8.4, 2.0 Hz, 1H), 4.90 (s, 2H), 3.94 (s, 3H).

[27-3] methyl 5-bromo-2-formylbenzoate (Compound <27-4>)

To the stirred suspension of an oven-dried 4 Å molecular sieve in acetonitrile (30 ml), NMO (1.80 g, 15.4 mmol) was added. In 5 minutes, compound 3 (2.06 g, 6.69 mmol) dissolved in acetonitrile (10 ml) was added. The reaction mixture was stirred at a room temperature for 1.5 hours, and it was filtered through silica-gel, and it was eluted with EtOAc and it was concentrated under vacuum to obtain reddish brown oil. The residues were purified by silica-gel column chromatography using EA/Hx (10%) as an eluent to obtain compound <27-4> (methyl 5-bromo-2-formyl benzoate) (977 mg, 4.02 mmol, 60%) as a white solid.

¹H NMR (300 MHz, CDCl₃) δ 10.61 (s, 1H), 8.06 (d, J=2.1 Hz, 1H), 7.88 (d, J=8.3 Hz, 1H), 7.77 (dd, J=8.3, 2.1 Hz, 1H), 3.98 (s, 3H).

[27-4] Synthesis of methyl (E)-5-bromo-2-(2-methoxyvinyl)benzoate (Compound <27-5>)

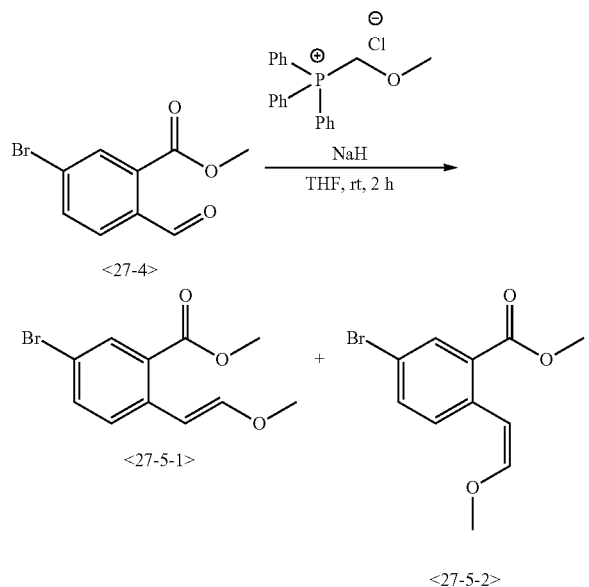

To the stirred suspension of (methoxymethyl)triphenylphosphonium chloride (1.06 g, 3.09 mmol) dissolved in THF (24 ml) under N₂ in an ice container, sodium hydride (165 mg, 4.12 mmol) was added in small portions. The red solution was stirred at a room temperature for 30 minutes, and then compound <27-4> (500 mg, 2.06 mmol) dissolved in THF (6 ml) dropwise. The reactants were stirred at a room temperature for 2 hours. The mixture was diluted with water and it was extracted with EtOAc (50 ml). The combined organic layer was washed with salt water, and it was dried on MgSO₄, and the solvent was removed under vacuum to obtain dark oil. The crude compound was purified by silica-gel column chromatography using EtOAc/Hex (30%) as an eluent to obtain compound <27-5> (methyl (E)-5-bromo-2-(2-methoxyvinyl)benzoate) (348 mg, 1.28 mmol, 61%) as yellow oil (mixture of about 5:1 E/Z isomers).

Compound <27-5-1>: ¹H NMR (300 MHz, CDCl₃) δ 7.76 (d, J=8.5 Hz, 1H), 7.56 (d, J=2.0 Hz, 1H), 7.32 (dd, J=8.5, 2.0 Hz, 1H), 7.00 (d, J=12.9 Hz, 1H), 6.72 (d, J=12.9 Hz, 1H), 3.88 (s, 3H), 3.73 (s, 3H).

Compound <27-5-2>: ¹H NMR (300 MHz, CDCl₃) δ 8.25 (d, J=2.0 Hz, 1H), 7.69 (d, J=8.4 Hz, 1H), 7.30 (dd, J=8.4, 2.0 Hz, 1H), 6.26 (d, J=7.3 Hz, 1H), 6.07 (d, J=7.3 Hz, 1H), 3.87 (s, 3H), 3.80 (s, 3H).

[27-5] Synthesis of methyl (E)-5-(((tert-butoxy carbonyl)amino)methyl)-2-(2-methoxyvinyl)benzoate (Compound <27-6>)

(Tert-butoxy carbonyl)amino)methyl)trifluoro borate (105 mg, 0.443 mmol), compound <27-5> (300 mg, 1.11 mmol), Pd(OAc)2 (12 mg, 0.055 mmol), SPhos (45 mg, 0.111 mmol) and potassium carbonate (459 mg, 3.32 mmol) were filled to a sealed tube. Then, toluene/H₂O was added to the reaction tube, and it was deaerated with N₂ for 30 minutes. The reaction mixture was stirred at 85° C. overnight, and then it was cooled to a room temperature. The produced mixture was extracted with EtOAc, and the organic layer was combined and it was dried with MgSO₄, and it was filtered. The solvent was removed under vacuum, and the mixture was purified by silica-gel column chromatography (MPLC) using EA/Hx (10%) as an eluent to obtain compound <27-6> (methyl (E)-5-(((tert-butoxy carbonyl)amino)methyl)-2-(2-methoxyvinyl)benzoate) (233 mg, 0.725 mmol, 65%) as colorless oil.

¹H NMR (300 MHz, CDCl₃) δ 7.86 (d, J=8.1 Hz, 1H), 7.29 (d, J=1.7 Hz, 1H), 7.10 (dd, J=8.1, 1.7 Hz, 1H), 6.98 (d, J=12.9 Hz, 1H), 6.75 (d, J=12.9 Hz, 1H), 4.93 (s, 1H), 4.31 (d, J=6.1 Hz, 2H), 3.88 (s, 3H), 3.72 (s, 3H), 1.46 (s, 9H); LC/MS (ESI) m/z [M+H]+: 322.0.

[27-6] Synthesis of (E)-5-(((tert-butoxy carbonyl)amino)methyl)-2-(2-methoxyvinyl)benzoic acid (Compound <27-7>)

To the solution of compound <27-6> (233 mg, 0.725 mmol) dissolved in MeOH (1.5 ml), H₂O (1.5 ml) and THF (4.5 ml), lithium hydroxide monohydrate (152 mg, 3.63 mmol) was added at a room temperature and it was stirred at 50° C. overnight. The reaction mixture was concentrated to remove THF and methanol. Subsequently, water (50 mL) was added, and 1N HCl (aqueous) was used to adjust it to pH 3, and it was extracted with EtOAc (50 ml×2 times). The combined organic layer was concentrated under reduced pressure to obtain <27-7> ((E)-5-(((tert-butoxy carbonyl)amino)methyl)-2-(2-methoxyvinyl)benzoic acid) (232 mg, 0.725 mmol, quant.) as yellow gel.

¹H NMR (300 MHz, CDCl₃) δ 7.99 (d, J=8.3 Hz, 1H), 7.31 (s, 1H), 7.14 (d, J=8.0 Hz, 1H), 6.99 (d, J=12.8 Hz, 1H), 6.81 (d, J=12.9 Hz, 1H), 5.00-4.83 (m, 1H), 4.33 (s, 2H), 3.73 (s, 3H), 1.47 (s, 9H); LC/MS (ESI) m/z [M−H]⁻: 306.0.

[27-7] Synthesis of tert-butyl (E)-(3-((2,6-dioxopiperidin-3-yl)carbamoyl)-4-(2-methoxyvinyl)benzyl)carbamate (Compound <27-8>)

To the solution of compound <27-7> (223 mg, 0.798 mmol), 3-aminopiperidine-2,6-dione hydrochloride (239 mg, 1.45 mmol), EDCl HCl (153 mg, 0.798 mmol), and HOBt H₂O (108 mg, 0.798 mmol), dissolved in DMF (10 ml), DIPEA (0.505 ml, 2.90 mmol) was added at a room temperature, and the reaction mixture was stirred at a room temperature for 3 hours. The reaction mixture was diluted with water, and it was extracted with EtOAc (50 ml×2 times). the combined organic layer was dried on MgSO₄, and the solvent was removed under vacuum to obtain yellow oil. The crude compound was purified by silica-gel column chromatography using MeOH/DCM (5%) as an eluent to obtain compound <27-8> (tert-butyl (E)-(3-((2,6-dioxopiperidin-3-yl)carbamoyl)-4-(2-methoxyvinyl)benzyl)carbamate) (124 mg, 0.297 mmol, 41%) as a sky-blue solid.

¹H NMR (300 MHz, DMSO-d₆) δ 10.85 (s, 1H), 8.51 (d, J=8.4 Hz, 1H), 7.47-7.36 (m, 2H), 7.28 (d, J=7.7 Hz, 1H), 7.17 (d, J=12.9 Hz, 1H), 7.05 (d, J=7.9 Hz, 1H), 6.28 (d, J=12.8 Hz, 1H), 4.78-4.68 (m, 1H), 4.11 (d, J=6.3 Hz, 2H), 3.65 (s, 3H), 2.81-2.72 (m, 1H), 2.14-1.92 (m, 3H), 1.40 (s, 9H); LC/MS (ESI) m/z [M+H]+: 417.9, [M−H]−: 416.0.

[27-8] Synthesis of 3-(7-(aminomethyl)-1-oxoisoquinolin-2(1H)-yl)piperidine-2,6-dione hydrochloride (Compound <27-9>)

To the solution of compound <27-8> (30 mg, 0.072 mmol) dissolved in 1,4-dioxane (1 ml), 4N HCl mixed with 1,4-dioxane (0.180 ml, 0.720 mmol) was added, and it was stirred at a room temperature for 2 hours. Then, the reaction mixture was stirred under the monowave-assisted condition at 150° C. for 1 hour. The reactants were evaporated. The residues were purified by silica-gel column chromatography using MeOH/DCM (5%) as an eluent to obtain compound <27-9> (3-(7-(aminomethyl)-1-oxoisoquinolin-2(1H)-yl)piperidine-2,6-dione hydrochloride) (26 mg, 0.072 mmol, quant.) as an ivory solid.

$^1$H NMR (300 MHz, DMSO-$d_6$) δ 11.06 (s, 1H), 8.40 (s, 3H), 8.24 (d, J=8.2 Hz, 1H), 7.74 (s, 1H), 7.61 (d, J=8.3 Hz, 1H), 7.48 (d, J=7.3 Hz, 1H), 6.67 (d, J=7.4 Hz, 1H), 5.62-5.43 (m, 1H), 4.20 (s, 2H), 2.95-2.79 (m, 1H), 2.77-2.58 (m, 2H), 2.13-1.98 (m, 1H);
LC/MS (ESI) m/z [M+H]+: 286.9, [M−H]−: 284.9.

[27-9] Synthesis of 1-(3-chloro-4-methylphenyl)-3-((2-(2,6-dioxopiperidin-3-yl)-1-oxo-1,2-dihydroisoquinolin-7-yl)methyl)urea (Compound <27-10>)

To the solution of compound <27-9> (23 mg, 0.071 mmol) dissolved in THF (0.5 ml), 3-chloro-4-methylphenyl isocyanate (12 mg, 0.071 mmol) and TEA (0.020 ml, 0.142 mmol) were added at a room temperature, and it was stirred at 40° C. overnight. The solvent was removed under vacuum, and the mixture was purified by silica-gel column chromatography (MPLC) using MeOH/DCM (6%) as an eluent to obtain <Chemical formula 47> (1-(3-chloro-4-methylphenyl)-3-((2-(2,6-dioxopiperidin-3-yl)-1-oxo-1,2-dihydroisoquinolin-7-yl)methyl)urea) (18 mg, 0.040 mmol, 56%) as a white solid.

$^1$H NMR (300 MHz, DMSO-$d_6$) δ 11.06 (s, 1H), 8.81 (s, 1H), 8.17 (d, J=8.3 Hz, 1H), 7.68 (s, 1H), 7.55 (s, 1H), 7.49-7.38 (m, 2H), 7.22-7.12 (m, 2H), 6.84 (t, J=5.8 Hz, 1H), 6.67 (d, J=7.4 Hz, 1H), 5.62-5.39 (m, 1H), 4.44 (d, J=5.8 Hz, 2H), 2.90-2.78 (m, 1H), 2.67-2.57 (m, 2H), 2.24 (s, 3H), 2.10-1.98 (m, 1H);
LC/MS (ESI) m/z [M+H]+: 454.9, [M−H]−: 452.8.

Example 28

Synthesis of 1-(4-chloro-3-(trifluoromethyl)phenyl)-3-((2-(2,6-dioxopiperidin-3-yl)-1-oxo-1,2-dihydroisoquinolin-7-yl)methyl)urea (Chemical Formula 48)

The compound of Chemical formula 48 was prepared according to the preparation method of Example 27.
$^1$H NMR (300 MHz, DMSO-$d_6$) δ 11.05 (s, 1H), 9.26 (s, 1H), 8.17 (d, J=8.3 Hz, 1H), 8.10 (s, 1H), 7.63 (d, J=9.1 Hz, 1H), 7.56 (d, J=6.4 Hz, 2H), 7.44 (dd, J=15.5, 7.9 Hz, 2H), 7.04 (s, 1H), 6.67 (d, J=7.4 Hz, 1H), 5.60-5.42 (m, 1H), 4.46 (d, J=5.9 Hz, 2H), 2.88-2.78 (m, 1H), 2.74-2.59 (m, 2H), 2.12-1.94 (m, 1H).

Example 29

Synthesis of 1-(3-chloro-4-methoxyphenyl)-3-((2-(2,6-dioxopiperidin-3-yl)-1-oxo-1,2-dihydroisoquinolin-7-yl)methyl)urea (Chemical Formula 49)

The compound of Chemical formula 49 was prepared according to the preparation method of Example 27.
$^1$H NMR (300 MHz, DMSO-$d_6$) δ 11.05 (s, 1H), 8.70 (s, 1H), 8.17 (d, J=8.6 Hz, 1H), 7.65 (s, 1H), 7.55 (s, 1H), 7.49-7.37 (m, 2H), 7.26-7.18 (m, 1H), 7.04 (d, J=8.7 Hz, 1H), 6.81 (s, 1H), 6.67 (d, J=7.0 Hz, 1H), 5.61-5.40 (m, 1H), 4.44 (s, 2H), 3.79 (s, 3H), 2.93-2.78 (m, 1H), 2.76-2.63 (m, 2H), 2.10-1.93 (m, 1H).

Example 30

Synthesis of 3-(5-hydroxy-4-oxobenzo[d][1,2,3]triazin-3(4H)-yl)piperidine-2,6-dione (Chemical Formula 57)

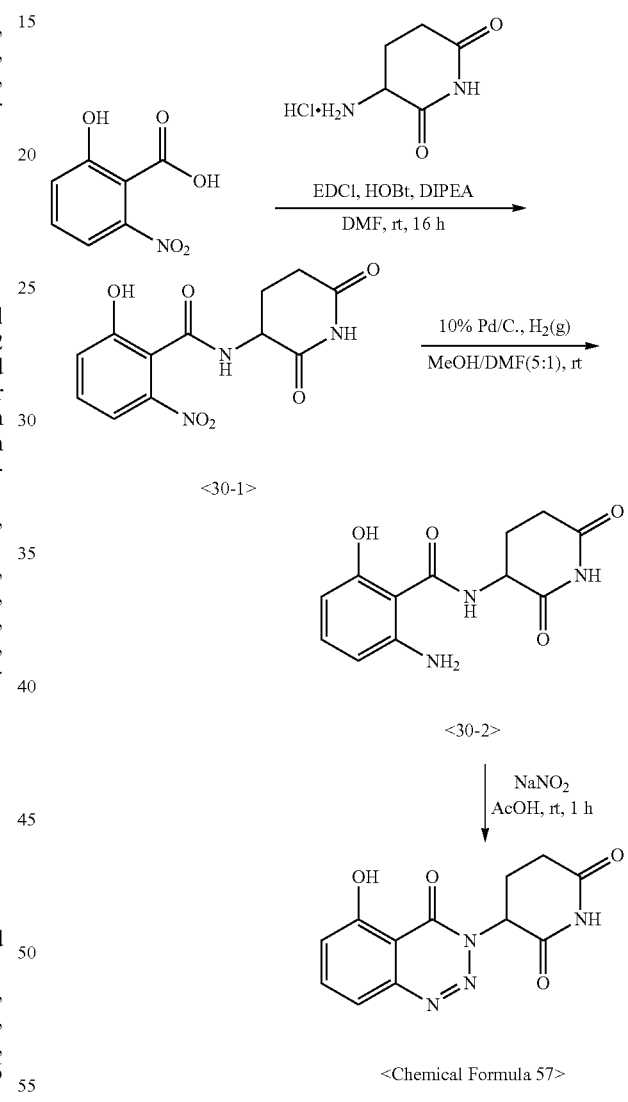

<Chemical Formula 57>

[30-1] Step 1 Reaction

The mixed solution of 2-hydroxy-6-nitrobenzoic acid (100 mg, 0.55 mmol), 2-aminoglutaimide hydrochloride (180 mg, 1.1 mmol), EDCl-HCl (116 mg, 0.605 mmol), HOBt (93 mg, 0.605 mmol), and DIEA (0.4 ml, 2.2 mmol) was stirred at a room temperature for 30 minutes. The reactants were separated through water and ethyl acetate, and then the organic layer was washed with salt water, and the remained water was dried by anhydrous magnesium sulfate and it was concentrated under reduced pressure, and then was separated and purified by column chromatography to obtain compound <30-1> (41 mg, 25%).

$^1$H NMR (300 MHz, DMSO-d$_6$) δ 10.85 (s, 1H), 8.83 (d, J=7.3 Hz, 1H), 7.50-7.41 (m, 2H), 7.23 (dd, J=7.6, 1.6 Hz, 1H), 4.78-4.70 (m, 1H), 2.79-2.68 (m, 1H), 2.59-2.54 (m, 1H), 2.14-2.09 (m, 1H), 1.96-1.85 (m, 1H).

[30-2] Step 2 Reaction

After dissolving compound <30-1> (34 mg) in the mixed solution of methanol/dimethylformamide (5/1) (6 ml), it was reacted under 10% Pd/C (15 mg) and hydrogen at a room temperature for 2 hours. The reactants were filtered by Celite, and then the filtrates were concentrated to obtain desired JYR-17-187 (22 mg, 70%, white solid).

$^1$H NMR (500 MHz, DMSO-d$_6$) δ 10.88 (s, 1H), 10.55 (s, 2H), 8.98 (s, 1H), 6.89 (t, J=8.0 Hz, 1H), 6.62 (s, 2H), 6.17 (d, J=8.1 Hz, 1H), 6.04 (d, J=7.8 Hz, 1H), 4.72-4.67 (m, 2H), 2.79-2.72 (m, 1H), 2.55-2.53 (m, 1H), 2.20-2.15 (m, 1H), 2.03-1.95 (m, 1H).

[30-3] Step 3 Reaction

After dissolving compound <30-2> (20 mg, 0.076 mmol) in acetic acid (2 ml), sodium nitrite (9 mg, 0.13 mmol) was added, and then it was stirred at a room temperature for 1 hour. The reactants were separated through water and ethyl acetate, and then the organic layer was washed with salt water, and the remained water was dried by anhydrous magnesium sulfate and it was concentrated under reduced pressure, and then was separated and purified by column chromatography to obtain the compound of Chemical formula 57 (2.7 mg, 13%, ivory solid).

$^1$H NMR (500 MHz, DMSO-d$_6$) δ 11.24 (s, 1H), 10.85 (s, 1H), 8.00 (t, J=8.2 Hz, 1H), 7.72 (d, J=8.0 Hz, 1H), 7.35 (d, J=8.3 Hz, 1H), 5.99-5.95 (m, 1H), 3.01-2.93 (m, 1H), 2.74-2.65 (m, 2H), 2.33-2.28 (m, 1H).

Example 31

Synthesis of (3-(5-amino-4-oxobenzo[d][1,2,3]triazin-3(4H)-yl)-2,6-dioxopiperidin-1-yl)methyl pivalate (Chemical Formula 58)

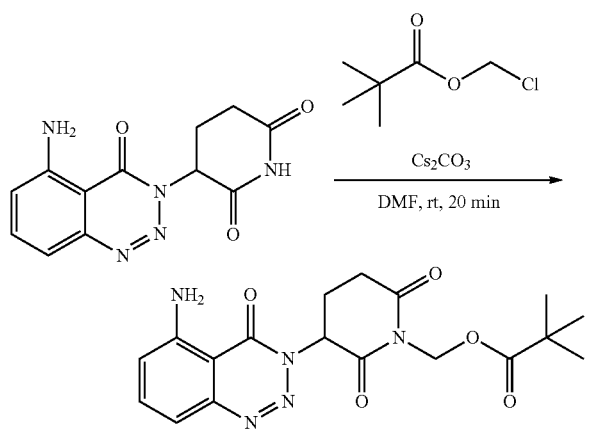

After dissolving 3-(5-amino-4-oxobenzo[d][1,2,3]triazin-3(4H)-yl)piperidine-2,6-dione (20 mg, 0.066 mmol) and cesium carbonate (30 mg, 0.099 mmol) in dimethylformamide, chloromethyl pivalate (0.014 ml, 0.099 mmol) was added, and it was stirred at a room temperature for 20 minutes. The reaction for reactants was completed by adding water, and it was extracted with ethyl acetate. The organic layer was washed with salt water and the remained water was dried by anhydrous magnesium sulfate and it was concentrated under reduced pressure, and then was separated and purified by column chromatography to obtain the targeted compound of Chemical formula 58.

$^1$H NMR (300 MHz, CDCl$_3$) δ 7.65 (t, J=8.0 Hz, 1H), 7.37 (dd, J=7.8, 0.9 Hz, 1H), 6.88 (dd, J=8.3, 0.9 Hz, 1H), 6.14 (s, 2H), 5.88 (s, 2H), 5.82-5.74 (m, 1H), 3.17-2.87 (m, 3H), 2.45-2.32 (m, 1H), 1.21 (s, 9H).

Example 32

Synthesis of (3-(5-amino-4-oxobenzo[d][1,2,3]triazin-3(4H)-yl)-2,6-dioxopiperidin-1-yl)methyl benzoate (Chemical Formula 59)

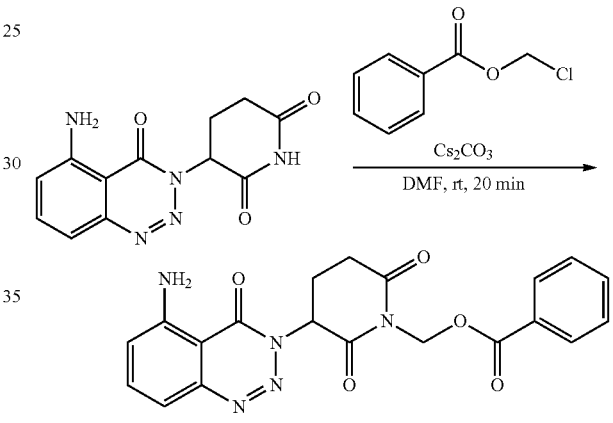

By the same method as the method of Example 31, except for using chloromethyl benzoate instead of chloromethyl pivalate, the compound of Chemical formula 59 was synthesized (17 mg, 63%).

$^1$H NMR (300 MHz, Chloroform-d) δ 8.06-7.99 (m, 2H), 7.62 (t, J=8.0 Hz, 1H), 7.59-7.52 (m, 1H), 7.46-7.39 (m, 2H), 7.34 (dd, J=7.8, 0.9 Hz, 1H), 6.85 (dd, J=8.3, 0.9 Hz, 1H), 6.19-6.03 (m, 4H), 5.83-5.74 (m, 1H), 3.19-2.85 (m, 3H), 2.45-2.33 (m, 1H).

Example 33

Synthesis of (3-(5-amino-4-oxobenzo[d][1,2,3]triazin-3(4H)-yl)-2,6-dioxopiperidin-1-yl)methyl piperidine-4-carboxylate hydrochloride (Chemical Formula 60)

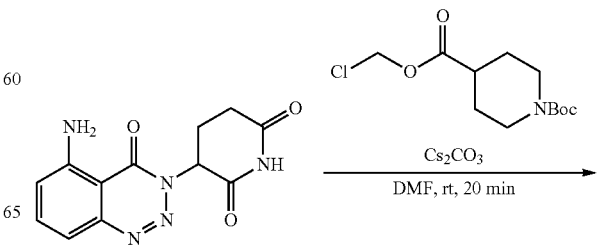

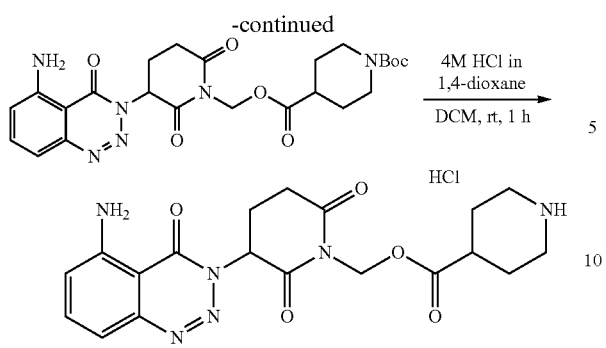

[33-1] Step 1 Reaction

By the same method as the method of Example 31, except for using 1-(tert-butyl)-4-(chloromethyl)piperidine-1,4-dicarboxylate instead of chloromethyl pivalate, the compound was synthesized (16 mg, 51%, yellow solid).

$^1$H NMR (300 MHz, CDCl$_3$) δ 7.65 (t, J=8.0 Hz, 1H), 7.36 (dd, J=7.8, 0.9 Hz, 1H), 6.88 (dd, J=8.3, 0.9 Hz, 1H), 6.17 (s, 2H), 5.90 (s, 2H), 5.79-5.70 (m, 1H), 4.01 (d, J=13.4 Hz, 2H), 3.17-3.06 (m, 1H), 2.93 (d, J=3.6 Hz, 1H), 2.85 (t, J=13.0 Hz, 2H), 2.54-2.35 (m, 2H), 1.88 (d, J=13.0 Hz, 2H), 1.74-1.64 (m, 2H), 1.47 (s, 9H).

[33-2] Step 2 Reaction

After dissolving the compound obtained in Step 1 in dichloromethane, 4N HCl 1,4-dioxene solution was added, and it was stirred at a room temperature for 1 hour. The reactants were concentrated to obtain the targeted compound of Chemical formula 60 (80%).

$^1$H NMR (300 MHz, CDCl$_3$) δ 7.63 (t, J=8.0 Hz, 1H), 7.37-7.33 (m, 1H), 6.89-6.81 (m, 1H), 6.14 (s, 2H), 5.87 (s, 2H), 5.78-5.72 (m, 1H), 3.82-3.58 (m, 1H), 3.19-3.01 (m, 3H), 2.99-2.82 (m, 2H), 2.70-2.57 (m, 2H), 2.55-2.29 (m, 2H), 1.89 (d, J=13.3 Hz, 2H), 1.75-1.55 (m, 2H).

Example 34

Synthesis of (3-(5-amino-4-oxobenzo[d][1,2,3]triazin-3(4H)-yl)-2,6-dioxopiperidin-1-yl)methyl D-prolinate hydrochloride (Chemical Formula 61) and 2-((3-(5-amino-4-oxobenzo[d][1,2,3]triazin-3(4H)-yl)-2,6-dioxopiperidin-1-yl)methyl) 1-(tert-butyl) (2R)-pyrrolidine-1,2-dicarboxylate (Chemical Formula 64)

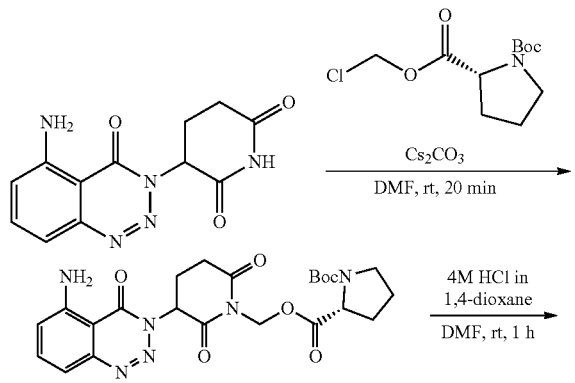

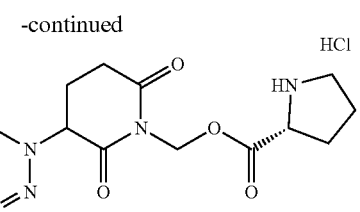

[34-1] Step 1 reaction

By the same method as the method of Example 31, except for using 1-(tert-butyl)2-(chloromethyl)(R)-pyrrolidine-1,2-dicarboxylate instead of chloromethyl pivalate, the compound of Chemical formula 64 was synthesized.

$^1$H NMR (300 MHz, CDCl$_3$) δ 7.66 (t, J=8.0 Hz, 1H), 7.37 (d, J=7.8 Hz, 1H), 6.89 (d, J=8.2 Hz, 1H), 6.15 (s, 2H), 5.93 (s, 1H), 5.80-5.69 (m, 1H), 3.15-2.85 (m, 4H), 2.38 (d, J=6.6 Hz, 1H), 2.23-1.99 (m, 1H), 1.91 (dd, J=13.5, 7.1 Hz, 1H), 1.84-1.78 (m, 3H).

[34-2] Step 2 Reaction

After dissolving the compound obtained in the step 1 in dichloromethane, 4N HCl 1,4-dioxene solution was added, and it was stirred at a room temperature for 1 hour. The reactants were concentrated to obtain the targeted compound of Chemical formula 61.

$^1$H NMR (300 MHz, CDCl$_3$) δ 7.66 (t, J=8.0 Hz, 1H), 7.37 (d, J=7.8 Hz, 1H), 6.89 (d, J=8.2 Hz, 1H), 6.15 (s, 2H), 5.93 (s, 1H), 5.80-5.69 (m, 1H), 3.15-2.85 (m, 4H), 2.38 (d, J=6.6 Hz, 1H), 2.23-1.99 (m, 1H), 1.91 (dd, J=13.5, 7.1 Hz, 1H), 1.84-1.78 (m, 3H).

Example 35

Synthesis of (3-(5-amino-4-oxobenzo[d][1,2,3]triazin-3(4H)-yl)-2,6-dioxopiperidin-1-yl)methyl L-isoleucinate hydrochloride (Chemical Formula 62)

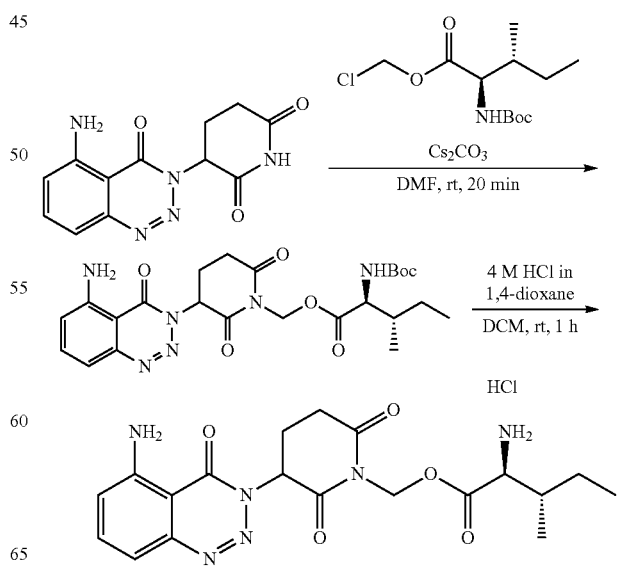

[35-1] Step 1 Reaction

By the same method as the method of Example 31, except for using (tert-butoxy carbonyl)-D-isoleucinate instead of chloromethyl pivalate, the compound was synthesized.

[35-2] Step 2 Reaction

After dissolving the compound obtained in the step 1 in dichloromethane, 4N HCl 1,4-dioxene solution was added, and it was stirred at a room temperature for 1 hour. The reactants were concentrated to obtain the targeted compound of Chemical formula 62.

$^1$H NMR (300 MHz, Chloroform-d) δ 7.69-7.61 (m, 1H), 7.36 (d, J=7.8 Hz, 1H), 6.88 (d, J=8.3 Hz, 1H), 6.16 (s, 2H), 5.92 (s, 2H), 5.83-5.71 (m, 1H), 3.37 (d, J=5.0 Hz, 1H), 3.18-2.82 (m, 3H), 2.48-2.30 (m, 1H), 1.54-1.38 (m, 1H), 1.27-1.08 (m, 2H), 0.95 (d, J=6.8 Hz, 2H), 0.94-0.85 (m, 4H).

Example 36

Synthesis of (3-(5-amino-4-oxobenzo[d][1,2,3]triazin-3(4H)-yl)-2,6-dioxopiperidin-1-yl)methyl butyrate (Chemical Formula 63)

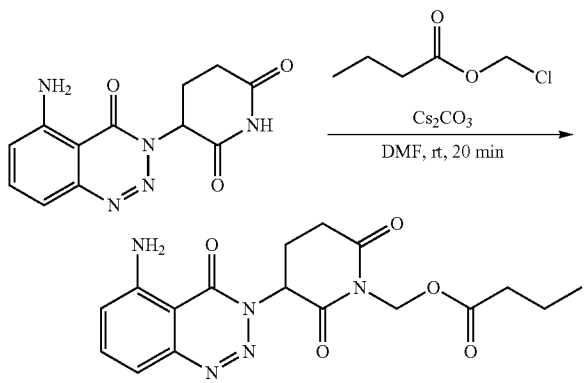

By the same method as the method of Example 31, except for using chloromethyl butyrate instead of chloromethyl pivalate, the compound of Chemical formula 63 was synthesized (44%, yellow solid).

$^1$H NMR (300 MHz, CDCl$_3$) δ 7.62 (t, J=8.1 Hz, 1H), 7.37-7.31 (m, 1H), 6.89-6.82 (m, 1H), 6.14 (s, 2H), 5.86 (d, J=2.2 Hz, 2H), 5.81-5.71 (m, 1H), 3.16-3.03 (m, 1H), 2.98-2.86 (m, 2H), 2.44-2.33 (m, 1H), 2.29 (t, J=7.4 Hz, 2H), 1.71-1.63 (m, 2H), 0.93 (t, J=7.4 Hz, 3H).

Example 37

Synthesis of 3-(6-amino-4-oxobenzo[d][1,2,3]triazin-3(4H)-yl)piperidine-2,6-dione (Chemical Formula 65)

The compound of Chemical formula 65 was prepared according to the preparation method of Example 7.

$^1$H NMR (500 MHz, Methanol-d$_4$) δ 7.88 (d, J=10.0 Hz, 1H), 7.30-7.28 (m, 2H), 5.87 (m, 1H), 3.02-2.79 (m, 3H), 2.39-2.32 (m, 1H).

Test Example 1

Evaluation of Substrate Proteolytic Activity Against CRBN

In order to confirm whether the compound of the present disclosure could inhibit the function of CRBN by specifically binding to CRBN (celebron), the effect of the present compound on the proteolytic activity of Ikaros/Aiolos protein (Nat Struct Mol Biol. 2014 September; 21(9):803-9) or GSPT1 protein (Nature 535, 252257 (14 Jul. 2016)), degraded by CRBN protein when binding to thalidomide and its derivative, was investigated.

Pomalidomide or CC-885 compound which inhibited the function by binding to CRBN was used as a positive control group.

To evaluate the degradative activity of Ikaros/Aiolos protein or GSPT1 protein of the compound according to the present disclosure, an experiment was conducted as follows.

$5 \times 10^5$ OCI-LY3 cells were seeded on a 12-well plate, and then each compound was treated to each well in a defined concentration. In 6 hours or 24 hours, cell lysates were collected using TBSN buffer. The proteolytic activity of Ikaros/Aiolos protein was evaluated using an antibody against Aiolos protein, and the proteolytic activity of GSPT1 was evaluated by western blot using an antibody against GSPT1 protein, and for this, the same amount of protein was loaded on each well of 4-15% gradient gel and then after electrophoresis, the protein was transferred to PVDF membrane, and the primary antibody against each protein was bound. After that, the secondary antibody in which HRP was attached was bound, and it was developed using HRP substrate.

As a result, as shown in FIG. 1, it could be seen that when treating the compound of the present disclosure, Ikaros/Aiolos protein was degraded in a concentration dependent manner, compared to the group treated with the negative control group, DMSO, and it tended to be similar to the positive control group, pomalidomide.

Figure 2:
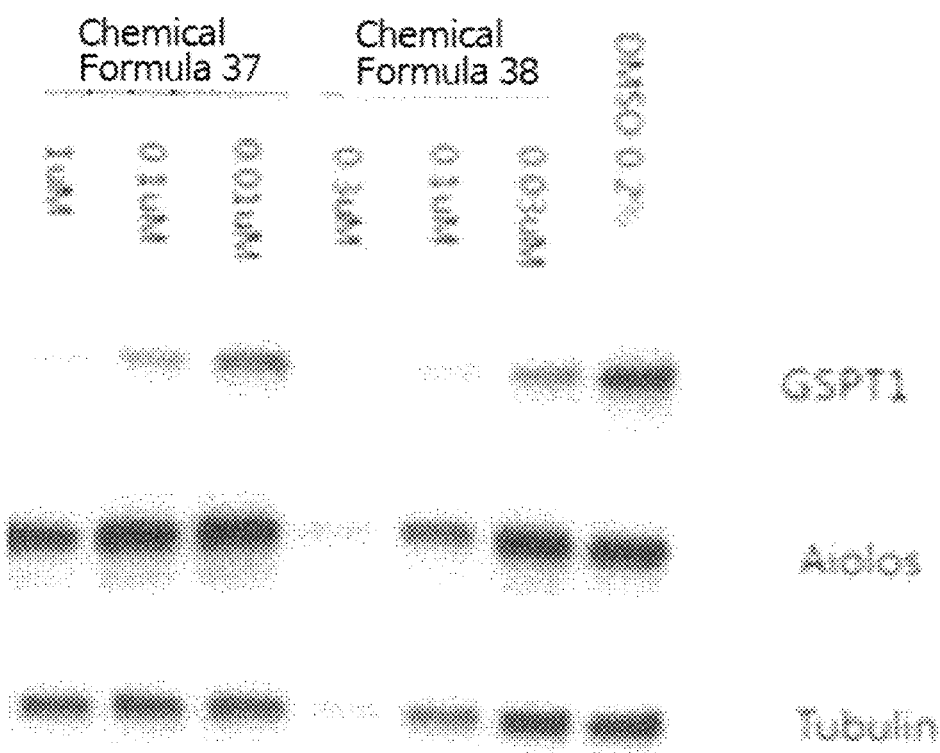
FIG. 2 is the measurement of the degradation activity against GSPT1 and Aiolos when the compound of Chemical formula 37 or 38 of the present disclosure is treated for 6 hours or 24 hours.

In addition, as shown in FIG. 2, as a result of treating for 6 hours or 24 hours, respectively, in the OCI-LY3 cell line, it could be confirmed that the compound of the present disclosure facilitated the degradation of GSPT1 protein and Aiolos protein.

Test Example 2

Cytotoxicity Experiment

In order to confirm the effect of the compound of the present disclosure on cancer cells and normal cells, the cytotoxicity experiment was conducted as follows.

After seeding NCI-H929 cells on a 96-well plate so as to be 10,000 cells per each well, each compound was treated in a predetermined concentration. In 72 hours, WST-1 reagent was added, and in 1 hour, the absorbance was measured at 450 nm using spectramax spectrophotometer to measure the degree of cell death. Using the measured value, IC$_{50}$ was calculated with graphpad prism program, and this was shown in Table 1.

TABLE 1

| Compound number | Cytotoxicity activity |
|---|---|
| Compound of Chemical formula 7 | A |
| Compound of Chemical formula 8 | B |

TABLE 1-continued

| Compound number | Cytotoxicity activity |
|---|---|
| Compound of Chemical formula 9 | C |
| Compound of Chemical formula 11 | B |
| Compound of Chemical formula 12 | C |
| Compound of Chemical formula 19 | C |
| Compound of Chemical formula 20 | C |
| Compound of Chemical formula 21 | C |
| Compound of Chemical formula 23 | C |
| Compound of Chemical formula 24 | C |
| Compound of Chemical formula 25 | B |
| Compound of Chemical formula 26 | C |
| Compound of Chemical formula 27 | C |
| Compound of Chemical formula 29 | C |
| Compound of Chemical formula 30 | C |
| Compound of Chemical formula 31 | C |
| Compound of Chemical formula 37 | A |
| Compound of Chemical formula 38 | A |
| Compound of Chemical formula 56 | C |
| Compound of Chemical formula 57 | A |
| Compound of Chemical formula 58 | A |
| Compound of Chemical formula 59 | A |
| Compound of Chemical formula 60 | A |
| Compound of Chemical formula 61 | A |
| Compound of Chemical formula 62 | A |
| Compound of Chemical formula 63 | A |
| Compound of Chemical formula 65 | C |

* $IC_{50}$ value - A: <1 μM, B: 1-10 μM, C: 10-50 μM, D: >50 μM

As a result, as shown in Table 1, it could be seen that the compounds of the present disclosure had sufficient cytotoxicity in the tumor cell, NCI-H929.

In particular, it could be confirmed that Compounds 7~9, 11, 12, 19~21, 23, 25~27, 29~31, 37, 38, 56~63 and 65 as triazine derivative compounds wherein X is N in the Chemical formula 1 of the present disclosure had the excellent cytotoxicity activity against cancer cells, compared to Compounds 24 and 31 as pyridine derivative compounds wherein X is C.

What is claimed is:

1. A compound represented by the following Chemical formula 1:

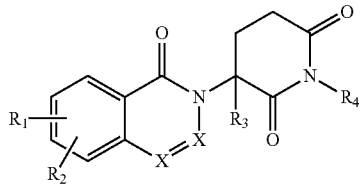

[Chemical formula 1]

or its pharmaceutically acceptable salt,
in the Chemical formula 1,
X is nitrogen (N) and
$R_1$ or $R_2$ is each independently any one selected from the group consisting of hydrogen, hydroxy, halogen, cyano, amino, nitro, —$NR_5R_6$, —$N(SO_2)R_7$, —$CONR_5R_6$, —$OR_5$, —$SR_5$, —$SO_2R_5$, —$SO_2NR_5R_6$, —$CR_5R_6$, —$CR_5NR_6R_7$, —$P(O)(OR_5)R_6$, —$P(O)R_5R_6$, —$OP(O)(OR_5)R_6$, —$OP(O)R_5R_6$, —$CF_3$, —$NR_5SO_2NR_5R_6$, —$CONR_5COR_6$, —$NR_5C(=N—CN)NR_5R_6$, —$C(=N—CN)NR_5R_6$, —$NR_5C(=N—CN)R_6$, —$NR_5C(=C—NO_2)NR_5R_6$, —$SO_2NR_5COR_6$, —$CO_2R_5$, —$C(C=N—OR_5)R_6$, —$CR_5=CR_5R_6$, —$CCR_5$, —$S(C=O)(C=N—R_5)R_6$, —$SF_5$, —$OCF_3$, —$NHCOR_5$, $C_1$-$C_{10}$ linear or branched alkyl, $C_2$-$C_{10}$ linear or branched alkenyl, $C_2$-$C_{10}$ linear or branched alkynyl, $C_1$-$C_{10}$ linear or branched alkoxy, $C_3$-$C_{10}$ cycloalkyl, $C_3$-$C_{10}$ heterocycloalkyl comprising one or more heteroatoms selected from the group consisting of N, O and S, $C_3$-$C_{10}$ cycloalkenyl, $C_3$-$C_{10}$ heterocycloalkenyl comprising one or more heteroatoms selected from the group consisting of N, O and S, $C_6$-$C_{14}$ aryl, $C_6$-$C_{24}$ arylalkyl, and $C_6$-$C_{14}$ heteroaryl comprising one or more heteroatoms selected from the group consisting of N, O and S, and $R_3$ is any one selected from the group consisting of hydrogen, deuterium and $C_1$-$C_{10}$ linear or branched alkyl, and $R_4$ is any one selected from the group consisting of hydrogen, —$(CH_2)_nOCOR_8$ and $C_1$-$C_{10}$ linear or branched alkyl, and $R_5$ to $R_7$ are each independently any one selected from the group consisting of hydrogen, amino, $C_1$-$C_{10}$ linear or branched alkyl, $C_2$-$C_{10}$ linear or branched alkenyl, $C_2$-$C_{10}$ linear or branched alkynyl, $C_3$-$C_{10}$ cycloalkyl, $C_3$-$C_{10}$ heterocycloalkyl comprising one or more heteroatoms selected from the group consisting of N, O and S, $C_6$-$C_{14}$ aryl and $C_6$-$C_{14}$ heteroaryl comprising one or more heteroatoms selected from the group consisting of N, O and S, $R_8$ is any one selected from the group consisting of hydrogen, unsubstituted or substituted amino, unsubstituted or substituted $C_1$-$C_{10}$ linear or branched alkyl, unsubstituted or substituted $C_2$-$C_{10}$ linear or branched alkenyl, unsubstituted or substituted $C_2$-$C_{10}$ linear or branched alkynyl, unsubstituted or substituted $C_3$-$C_{10}$ cycloalkyl, unsubstituted or substituted $C_3$-$C_{10}$ heterocycloalkyl comprising one or more heteroatoms selected from the group consisting of N, O and S, unsubstituted or substituted $C_6$-$C_{14}$ aryl or unsubstituted or substituted $C_6$-$C_{14}$ heteroaryl comprising one or more heteroatoms selected from the group consisting of N, O and S, wherein said substituted amino, substituted $C_1$-$C_{10}$ alkyl, substituted $C_2$-$C_{10}$ alkenyl, substituted $C_2$-$C_{10}$ alkynyl, substituted $C_3$-$C_{10}$ cycloalkyl, substituted $C_3$-$C_{10}$ heterocycloalkyl, substituted $C_6$-$C_{14}$ aryl, and substituted $C_6$-$C_{14}$ heteroaryl wherein the substituted $R_8$ are substituted with one or more substituents selected from the group consisting of halogen atom, nitro, hydroxy, cyano, amino, thiol, carboxyl, amide, nitrile, sulfide, disulfide, sulphenyl, formyl, formyloxy, formylamino, $C_6$-$C_{14}$ aryl, and tert-butyloxycarbonyl (BOC), and n is an integer of 1 to 5.

2. The compound or its pharmaceutically acceptable salt according to claim 1,
wherein in the Chemical formula 1,
$R_1$ or $R_2$ is each independently any one selected from the group consisting of hydrogen, hydroxy, halogen, cyano, amino, nitro, —$CH_3$, —$OCF_3$, —$OCH_3$, —$NHCOCH_3$, —COOH, —$CONH_2$, —$CONHCH_3$ and —$NHCOC_6H_5$, and
$R_4$ is any one selected from the group consisting of

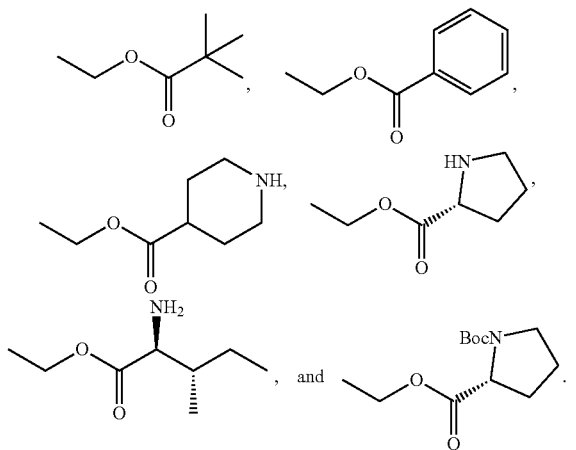

3. The compound or its pharmaceutically acceptable salt according to claim 1,
wherein the compound of Chemical formula 1 is selected from the group consisting of
3-(5-amino-4-oxobenzo[d][1,2,3]triazin-3(4H)-yl)piperidine-2,6-dione,
3-(5-fluoro-4-oxobenzo[d][1,2,3]triazin-3(4H)-yl)piperidine-2,6-dione,
3-(5-nitro-4-oxobenzo[d][1,2,3]triazin-3(4H)-yl)piperidine-2,6-dione,
3-(5-chloro-4-oxobenzo[d][1,2,3]triazin-3(4H)-yl)piperidine-2,6-dione,
3-(5-methyl-4-oxobenzo[d][1,2,3]triazin-3(4H)-yl)piperidine-2,6-dione,
3-(6-chloro-4-oxobenzo[d][1,2,3]triazin-3(4H)-yl)piperidine-2,6-dione,
3-(6-bromo-4-oxobenzo[d][1,2,3]triazin-3(4H)-yl)piperidine-2,6-dione,
3-(6-iodo-4-oxobenzo[d][1,2,3]triazin-3(4H)-yl)piperidine-2,6-dione,
3-(8-bromo-6-methyl-4-oxobenzo[d][1,2,3]triazin-3(4H)-yl)piperidine-2,6-dione,
3-(2,6-dioxopiperidin-3-yl)-4-oxo-3,4-dihydrobenzo[d][1,2,3]triazin-6-carbonitrile,
3-(5-iodo-4-oxobenzo[d][1,2,3]triazin-3(4H)-yl)piperidine-2,6-dione,
3-(4-oxo-6-(trifluoromethoxy)benzo[d][1,2,3]triazin-3(4H)-yl)piperidine-2,6-dione,
3-(6-methoxy-4-oxobenzo[d][1,2,3]triazin-3(4H)-yl)piperidine-2,6-dione,
N-(3-(2,6-dioxopiperidin-3-yl)-4-oxo-3,4-dihydrobenzo[d][1,2,3]triazin-5-yl)acetamide,
3-(8-nitro-4-oxobenzo[d][1,2,3]triazin-3(4H)-yl)piperidine-2,6-dione,
3-(8-amino-4-oxobenzo[d][1,2,3]triazin-3(4H)-yl)piperidine-2,6-dione,
N-(3-(2,6-dioxopiperidin-3-yl)-4-oxo-3,4-dihydrobenzo[d][1,2,3]triazin-6-yl)acetamide,
3-(4-oxobenzo[d][1,2,3]triazin-3(4H)-yl)piperidine-2,6-dione,
3-(7-nitro-4-oxobenzo[d][1,2,3]triazin-3(4H)-yl)piperidine-2,6-dione,
3-(6-nitro-4-oxobenzo[d][1,2,3]triazin-3(4H)-yl)piperidine-2,6-dione,
3-(7-amino-4-oxobenzo[d][1,2,3]triazin-3(4H)-yl)piperidine-2,6-dione,
3-(2,6-dioxopiperidin-3-yl)-4-oxo-3,4-dihydrobenzo[d][1,2,3]triazin-5-carboxylic acid,
3-(5-amino-4-oxobenzo[d][1,2,3]triazin-3(4H)-yl)-3-methylpiperidine-2,6-dione,
3-(2,6-dioxopiperidin-3-yl)-4-oxo-3,4-dihydrobenzo[d][1,2,3]triazin-5-carboxamide,
3-(2,6-dioxopiperidin-3-yl)-N-methyl-4-oxo-3,4-dihydrobenzo[d][1,2,3]triazin-5-carboxamide,
N-(3-(2,6-dioxopiperidin-3-yl)-4-oxo-3,4-dihydrobenzo[d][1,2,3]triazin-5-yl)benzamide,
3-(5-hydroxy-4-oxobenzo[d][1,2,3]triazin-3(4H)-yl)piperidine-2,6-dione,
(3-(5-amino-4-oxobenzo[d][1,2,3]triazin-3(4H)-yl)-2,6-dioxopiperidin-1-yl)methyl pivalate,
(3-(5-amino-4-oxobenzo[d][1,2,3]triazin-3(4H)-yl)-2,6-dioxopiperidin-1-yl)methyl benzoate,
(3-(5-amino-4-oxobenzo[d][1,2,3]triazin-3(4H)-yl)-2,6-dioxopiperidin-1-yl)methyl piperidine-4-carboxylate hydrochloride,
(3-(5-amino-4-oxobenzo[d][1,2,3]triazin-3(4H)-yl)-2,6-dioxopiperidin-1-yl)methyl D-prolinate hydrochloride,
(3-(5-amino-4-oxobenzo[d][1,2,3]triazin-3(4H)-yl)-2,6-dioxopiperidin-1-yl)methyl L-isoleucinate hydrochloride,
(3-(5-amino-4-oxobenzo[d][1,2,3]triazin-3(4H)-yl)-2,6-dioxopiperidin-1-yl)methyl butyrate,
2-((3-(5-amino-4-oxobenzo[d][1,2,3]triazin-3(4H)-yl)-2,6-dioxopiperidin-1-yl)methyl) 1-(tert-butyl) (2R)-pyrrolidine-1,2-dicarboxylate and
3-(6-amino-4-oxobenzo[d][1,2,3]triazin-3(4H)-yl)piperidine-2,6-dione.

4. A method comprising
(a) reacting the compound represented by the following Chemical formula 2 with the compound represented by the following Chemical formula 3 to prepare a compound represented by the following Chemical formula 4; and
(b) reacting the compound represented by the following Chemical formula 4 with $NaNO_2$ to prepare the compound represented by the following Chemical formula 5,

[Chemical formula 2]

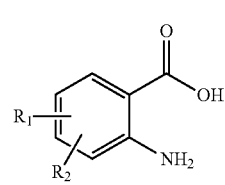

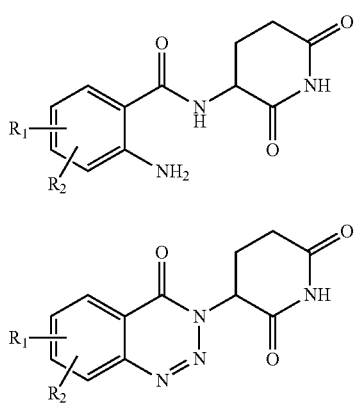

[Chemical formula 3]

[Chemical formula 4]

[Chemical formula 5]

in the Chemical formula 2,
$R_1$ or $R_2$ are each independently any one selected from the group consisting of hydrogen, hydroxy, halogen, cyano, amino, nitro, —$CH_3$, —$OCF_3$, —$OCH_3$, —$NHCOCH_3$, —COOH, —$CONH_2$, —$CONHCH_3$ and —$NHCOC_6H_5$.

5. A method for treating leprosy, chronic graft versus host disease, or cancer, comprising:

administering to a subject in need thereof a therapeutically effective amount of the compound or its pharmaceutically acceptable salt of claim 1, wherein the cancer is selected from the group consisting of breast cancer, colorectal cancer, lung cancer, small cell lung cancer, gastric cancer, liver cancer, blood cancer, bone cancer, pancreatic cancer, skin cancer, head or neck cancer, skin or intraocular melanoma, uterine cancer, ovarian cancer, rectal cancer, anal region cancer, colon cancer, breast cancer, fallopian tube carcinoma, endometrial cancer, cervical cancer, vaginal cancer, vulva cancer, Hodgkin disease, esophageal cancer, small intestine cancer, endocrine gland cancer, thyroid cancer, parathyroid cancer, adrenal cancer, soft tissue sarcoma, urethral cancer, penile cancer, prostate cancer, chronic or acute leukemia, lymphocytic lymphoma, bladder cancer, kidney or ureteral cancer, renal cell carcinoma, renal pelvic carcinoma, CNS tumor, primary CNS lymphoma, spinal cord tumor, brainstem glioma and pituitary adenoma.

\* \* \* \* \*